United States Patent
Ledbetter, Jr. et al.

(10) Patent No.: US 8,812,421 B1
(45) Date of Patent: Aug. 19, 2014

(54) METHOD AND APPARATUS FOR AUTONOMOUS SYNCHRONOUS COMPUTING

(75) Inventors: Carl Scotius Ledbetter, Jr., Denver, CO (US); Evar Dare Nering, Jr., Scottsdale, AZ (US)

(73) Assignee: Euler Optimization, Inc., Denver, CO (US)

( * ) Notice: Subject to any disclaimer, the term of this patent is extended or adjusted under 35 U.S.C. 154(b) by 0 days.

(21) Appl. No.: 13/532,216

(22) Filed: Jun. 25, 2012

Related U.S. Application Data

(63) Continuation-in-part of application No. 12/481,424, filed on Jun. 9, 2009.

(60) Provisional application No. 61/059,971, filed on Jun. 9, 2008, provisional application No. 61/592,416, filed on Jan. 30, 2012, provisional application No. 61/592,411, filed on Jan. 30, 2012, provisional application No. 61/592,422, filed on Jan. 30, 2012, provisional application No. 61/662,608, filed on Jun. 21, 2012.

(51) Int. Cl.

| | | |
|---|---|---|
| *G06F 17/00* | (2006.01) | |
| *G06N 5/02* | (2006.01) | |
| *G06N 5/00* | (2006.01) | |
| *G01J 3/28* | (2006.01) | |
| *G01N 21/64* | (2006.01) | |
| *G01N 21/27* | (2006.01) | |
| *G06F 17/50* | (2006.01) | |

(52) U.S. Cl.
CPC ............... *G06N 5/003* (2013.01); *G06F 17/00* (2013.01); *G06N 5/02* (2013.01); *G01J 2003/2866* (2013.01); *G01N 2021/6417* (2013.01); *G01N 21/274* (2013.01); *G01N 21/6428* (2013.01); *G06F 17/5072* (2013.01)
USPC .......................................................... 706/46

(58) Field of Classification Search
CPC ................ G01J 2003/2866; G01N 2021/6417; G06N 5/003
USPC .......................................................... 706/46
See application file for complete search history.

(56) References Cited

U.S. PATENT DOCUMENTS

| | | |
|---|---|---|
| 4,744,028 A | 5/1988 | Karmarkar |
| 5,136,538 A | 8/1992 | Karmarkar et al. |

(Continued)

OTHER PUBLICATIONS

'Linear programming and extensions': Dantzig, 1998, Princeton University Press, pp. 210-227.*
"Strategyproof Mechanisms for Scheduling Divisible Loads in Linear Networks" : Carroll, 2006, ACM.*
Dantzig, 1998, Princeton University Press, p. 216-217, "Linear Programming and Extensions".

(Continued)

*Primary Examiner* — Kakali Chaki
*Assistant Examiner* — Peter Coughlan
(74) *Attorney, Agent, or Firm* — HolzerIPLaw, PC

(57) ABSTRACT

In accordance with one embodiment, a special purpose computer can be implemented for processing a linear optimization problem capable of being represented in the form [A][X]+[I][Y]=[B] and wherein the linear optimization problem can also be represented in the form [E][A][X]+[E][I][Y]=[E][B]. The computer may comprise a first processor; a plurality of row processors each configured to store a row of the matrix [E]; a computer memory in communication with the first processor and in communication with each row processor so that each row processor can read from the computer memory and write to the computer memory; wherein the first processor is configured to signal all of the row processors to process data related to the linear optimization problem.

22 Claims, 27 Drawing Sheets

(56) References Cited

U.S. PATENT DOCUMENTS

| | | |
|---|---|---|
| 6,078,938 A | 6/2000 | Pan et al. |
| 6,694,343 B2 | 2/2004 | Forrest et al. |
| 6,950,844 B2 | 9/2005 | Walster et al. |
| 7,065,545 B2 | 6/2006 | Quintero-de-la-Garza |
| 7,877,286 B1 | 1/2011 | Neal et al. |
| 2002/0087823 A1 | 7/2002 | Chow et al. |
| 2004/0034556 A1 | 2/2004 | Matheson et al. |
| 2004/0107012 A1* | 6/2004 | Das et al. .................. 700/53 |
| 2006/0101050 A1* | 5/2006 | Choy et al. ................ 707/101 |
| 2006/0291693 A1* | 12/2006 | Olson et al. ................ 382/103 |
| 2007/0192406 A1 | 8/2007 | Frietsch et al. |
| 2007/0239966 A1* | 10/2007 | Georgiou et al. ............ 712/28 |
| 2008/0147473 A1 | 6/2008 | Zhong et al. |

OTHER PUBLICATIONS

Nering et al., 1993, Academic Press, Inc., "Linear Programs and Related Problems".

Cook, 2012, Princeton University Press, "In Pursuit of the Traveling Salesman: Mathematics at the Limits of Computation".

U.S. Appl. No. 13/532,201, filed Jun. 25, 2012, entitled "Method, Apparatus, and Article of Manufacture for Solving Linear Optimization Problems".

U.S. Appl. No. 13/532,208, filed Jun. 25, 2012, entitled "Method, Apparatus, and Article of Manufacture for Performing a Pivot-in-Place Operation for a Linear Programming Problem".

RueB, Harald et al, "Solving Linear Arithmetic Constraints," CSL Technical Report CSL-SRI-04-01, dated Jan. 15, 2004, 25 pages.

\* cited by examiner

METHOD AND APPARATUS FOR AUTONOMOUS SYNCHRONOUS COMPUTING

RELATED APPLICATIONS

This application is a continuation-in-part and claims the benefit under 35 U.S.C. §120 of U.S. patent application Ser. No. 12/481,424 filed on Jun. 9, 2009, which claims the benefit under 35 U.S.C. §119 of U.S. Patent Application No. 61/059,971 filed on Jun. 9, 2008, which are hereby incorporated by reference in their entirety and for all purposes. This application also claims the benefit of United States Provisional Patent Applications:

61/592,411 filed on Jan. 30, 2012 entitled "Overview of the Virtual Simplex Method";
61/592,416 filed on Jan. 30, 2012 entitled "A Tour Guide to Vsm, a Program to Run the Virtual Simplex Method";
61/592,422 filed on Jan. 30, 2012 entitled "Method, Apparatus, and Article of Manufacture for Solving Linear Optimization Problems Including Linear Programming Problems and Systems of Linear Equations"; and
61/662,608 filed on Jun. 21, 2012 and entitled "Methods and Apparatus Relating to Advances in Virtual Simplex Method."

Commonly-owned utility applications entitled "Method, Apparatus, and Article of Manufacture for Solving Linear Optimization Problems" and "Method, Apparatus, and Article of Manufacture for Performing a Pivot-in-Place Operation for a Linear Programming Problem" are concurrently filed herewith.

BACKGROUND

Former IBM Chief Scientist Ralph Gomory estimated in the mid-1980s that roughly half of all scientific and technical computing cycles ever expended to that time had been used to solve the class of linear optimization problems called Linear Programming problems (LP problems).

This is a staggering statistic given that this area of industry is not a household phrase. However, linear programming applies to many of the important industrial and economic operations that are performed in the world today. From distributing resources throughout the world, to operating power grids, to trading securities, linear programming techniques can be used to find optimum solutions under specified constraints. Thus, linear programming problems are extremely important to the efficient operation of the modem world. Indeed, the first patent ever granted that was associated with software is believed to be Great Britain patent number 1,039,141 titled "A Computer Arranged for the Automatic Solution of Linear Programming Problems" and granted in 1966.

As another example of the importance of linear programming, noted mathematician Martin Grötschel commented in 2006 that: "The development of linear programming is—in my opinion—the most important contribution of the mathematics of the $20^{th}$ century to the solution of practical problems arising in industry and commerce."

An example of the use of linear programming can be seen with respect to an industrial plant that has limited resources of equipment, labor, and raw materials. Each of these variables plays a role in how much of each product the plant can produce—(they constrain what is possible). Furthermore, each resource has an associated cost. The profit of such an industrial plant can be modeled through the use of a linear programming problem. And, solving that linear programming problem will amount to optimizing (maximizing) the profit that can be achieved while staying within the constraints of the resources available, and specifying how much of each resource (equipment, labor, and raw materials) should be used to attain the greatest profit for the plant.

As a more detailed example, suppose that in producing two types of containers K and L one uses two machines $M_1$ and $M_2$. To produce a container K, one needs $M_1$ for two minutes and $M_2$ for four minutes. Similarly, production of the L container requires use of $M_1$ for eight minutes and $M_2$ for four minutes. The net profit for L is $45 and the net profit for K is $29. What is the production plan that maximizes the net profit? Linear programming can be utilized to solve this problem by optimizing the amount of profit possible by deciding how many L and how many K containers to build, subject to the constraints of time available on the two machines $M_1$ and $M_2$.

For example, if we produce $x_1$ containers K and $x_2$ containers L per hour, the profit per hour is:

$$f(x_1,x_2)=29x_1+45x_2.$$

The constraints are:

$$2x_1+8x_2 \leq 60 \text{(resulting from machine } M_1\text{)}$$

$$4x_1+4x_2 \leq 60 \text{(resulting from machine } M_2\text{)}$$

$$x_1 \geq 0$$

$$x_2 \geq 0.$$

Having set up the problem, one can then go on to find the values of $x_1$ and $x_2$ that will produce the greatest profit "f" using linear programming techniques.

Through the years, people have tried to employ computers to solve linear programming problems. This has met with mixed success. For example, in the rather slow world of optimizing a process for an industrial plant, an optimum solution can eventually be obtained heuristically over time, e.g., by trial and error. Depending on the linear objective equation and the linear constraints, the computer optimization process might have to be re-run several times to handle difficulties that might occur initially because of the use of the computer. This will produce results of calculations on the way to a solution that are almost always inexact because of the way computers store numbers. Computers necessarily have to truncate and round numbers off when there are not enough bits available in the representation to give an exact answer. Other difficulties include having the problem cycle, arriving at a clearly incorrect answer, or encountering changing conditions.

These and other difficulties with the use of a computer to do the calculations can lead to arriving at incorrect answers, presenting a proposed solution that is actually infeasible, and incorrectly indicating that there is no feasible solution when there is one that the computer misses because of the accumulated arithmetical errors. Other difficulties may arise from such situations as we will discuss later, including encountering changing conditions (changes, for instance, in prices or constraints) or technical problems in the convergence of the method on a solution that are exacerbated by the arithmetic errors the computer introduces.

Nevertheless, given the relatively slow nature of some industrial plant processes, such a delay did not cause any real practical difficulty since the best solution could be found quickly enough to be economically practical. However, in faster processes that operate in "real time" it becomes much more important to have a reliable method that is not subject to error and that is potentially fast.

Several different methods have been used in the past to approach the solving of linear programs. The more popular of these are known as the Simplex Algorithm, the Revised Simplex Algorithm, the Stored Inverse form of the Revised Simplex Algorithm (SIRSA), and the Implied Inverse form of the Revised Simplex Algorithm (IIRSA).

Algebraic methods for solving linear programs, including all previous versions of methods that are based on the Simplex Algorithm, involve constructing a sequence of equivalent representations of the original problem until a representation is obtained for which the solution is obvious. If the original linear programming problem is of the form Ax=B these methods proceed by attempting to generate a sequence of equivalent systems $A_1x=b_1, A_2x=b_2, A_3x=b_3, \ldots, A_k x=b_k$ until the solution can be read off in an obvious way from the final system. If the calculations that are performed to generate such a sequence of equivalent systems are exact, this technique produces an exactly correct solution.

However, when implemented on digital computers, the calculations are almost never exact in problems that occur in the real world because of errors inherent in the way computers do these calculations. Therefore, while theoretically sound, these traditional algebraic methods fail to produce precisely equivalent representations of the original system Ax=B in actual computer implementations due to the computer error. As a result, all previous versions of simplex-like methods implemented by computer produce results which are (usually) not actually solutions to the original problem. The results they achieve are (usually) fairly close to an exact solution, but they contain errors which are hard to quantify. In certain badly behaved problems that are difficult for computers to handle, called ill-conditioned problems, the answer the computer produces may even be completely unacceptable because these methods may produce, because of the accumulation of computer errors, an answer that presents an optimal solution when there is not one. Or these methods may fail to find an optimal solution when there is one. Moreover, it can be difficult to tell when the answers that these methods produce are defective in one of these ways.

The accumulation of computer errors can be envisioned from the sequence $A_1x=b_1, A_2x=b_2, A_3x=b_3, \ldots, A_k x=b_k$. This sequence should lead to the optimization of the linear equation system to attain a proposed solution. With the error introduced in each subsequent calculation of $A_i$/due to computer round-off error, one can appreciate that there will be an accumulation of computer error as the processing proceeds to the proposed solution $A_k x=b_k$. For example, the computer error in $A_2$ would be propagated to $A_3$ and the computer error in $A_3$ would be propagated to $A_4$. Thus, while an algebraic technique may work exactly when implemented by hand, the introduction of a computer to perform the calculations leads to unavoidable computer errors. The proposed solution to such computer errors in the past has been to use numerical analysis techniques to analyze the solution steps and then try to re-implement the path to the solution that had been arrived at using fewer steps—so as to reduce the accumulated computer error caused by any additional steps. Essentially, this has been a post-hoc attempt to reduce the accumulated error after a proposed solution is achieved—and it requires reattempting a solution. Obviously, such a process of re-attempting a solution introduces a delay in arriving at the solution.

Another type of difficulty is encountered when dealing with linear programming problems whose constraints or other data change during the process of trying to optimize the problem, or after an optimal solution has been obtained. For example, one could envision that during the trading of mortgage backed securities that the price of the security could change quickly, which would affect the optimal solution to the problem. Thus, one would be required to start over from the beginning with the new value for the price. There are many such problems in industry. These problems are known as being "inherently dynamic."

In addition to the existing simplex-like methods, some alternative methods known as interior point methods have evolved that have gained some attention since the publication of the Simplex Algorithm by George Dantzig in 1947. For example, Leonid G. Khachiyan in 1979 proposed an ellipsoidal method. And, in 1984, Narendra Karmarkar introduced an interior point method for solving linear equations. See, for example, U.S. Pat. No. 4,744,028 issued to AT&T in the name of Narendra Karmarkar.

Other patents related to linear programming include for example, U.S. Pat. No. 5,136,538 to Karmarkar et al. titled "Preconditioned Conjugate Gradient System"; U.S. Pat. No. 6,078,938 to Pan et al. titled "Method and System for Solving Linear Systems"; U.S. Pat. No. 6,694,343 to Forrest et al. titled "Method for Solving a Large Sparse Triangular System of Linear Equations"; U.S. Pat. No. 6,950,844 to Walster et al. titled "Method and Apparatus for Solving Systems of Linear Inequalities"; and U.S. Pat. No. 7,065,545 to Quintero-de-la-Garza titled "Computer Methods of Vector Operation for Reducing Computation Time."

Nevertheless, difficulties involved with computer implementations of methods for solving linear programming problems remain. For example, as outlined above, the accumulation of computer errors causes a problem. As another example, changing conditions in dynamic problems also cause difficulties.

Thus, there is a need for improvement in the current state of affairs.

SUMMARY

In accordance with one embodiment, a special purpose computer can be implemented for processing a linear optimization problem capable of being represented in the form [A][X]+[I][Y]=[B] and wherein the linear optimization problem can also be represented in the form [E][A][X]+[E][I][Y]=[E][B]. The computer may comprise a first processor; a plurality of row processors each configured to store a row of the matrix [E]; a computer memory in communication with the first processor and in communication with each row processor so that each row processor can read from the computer memory and write to the computer memory; wherein the first processor is configured to signal all of the row processors to process data related to the linear optimization problem.

Further embodiments will be apparent to those of ordinary skill in the art from a consideration of the following description taken in conjunction with the accompanying drawings, wherein certain methods, apparatuses, and articles of manufacture are illustrated. This summary is provided merely to introduce certain concepts rather than to identify any key or essential features of the claimed subject matter.

DETAILED DESCRIPTION

I. Overview

Figure 1A:
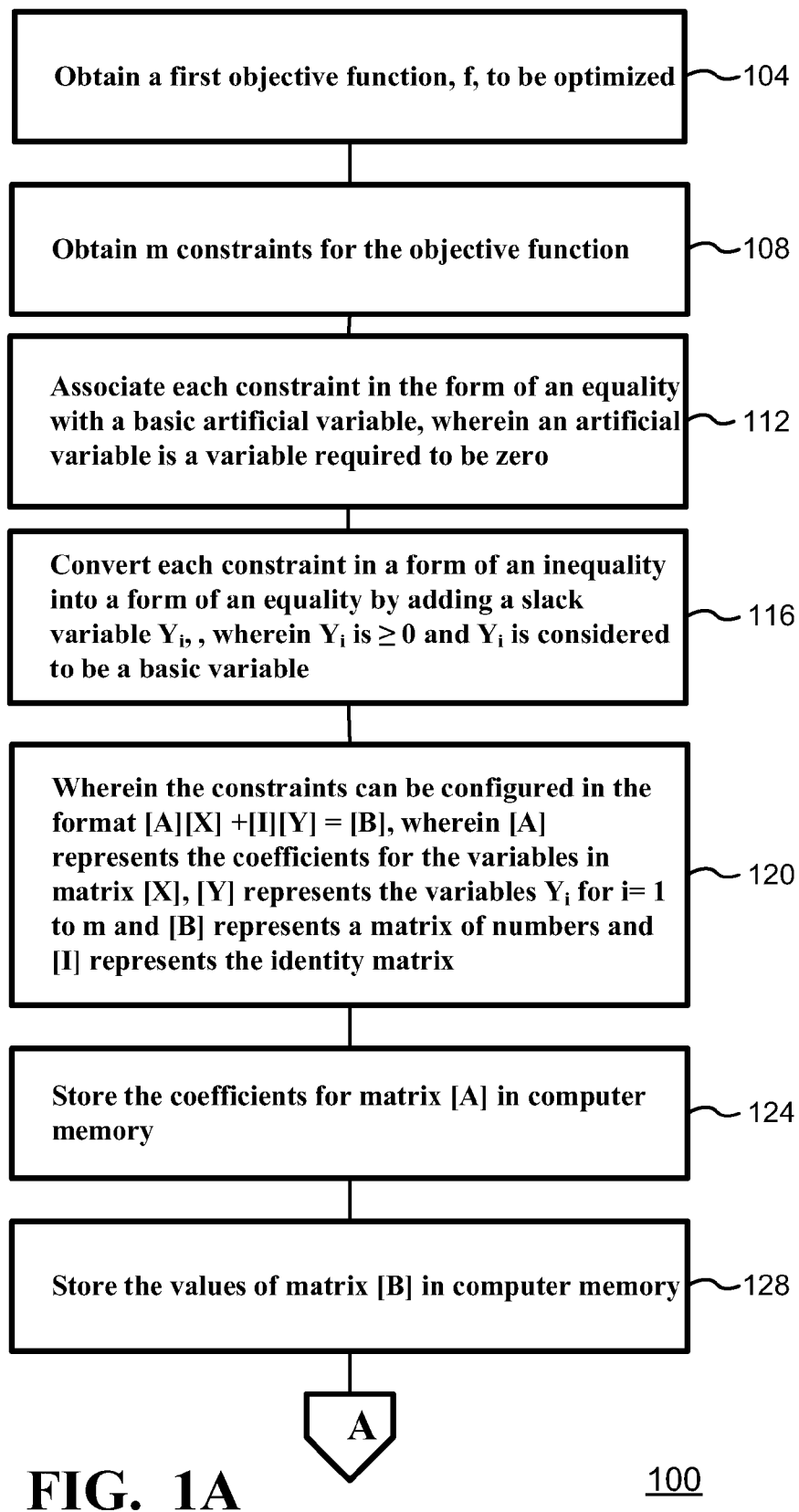
FIGS. 1A, 1B, and 1C are a flowchart illustrating a method of solving a linear programming problem on a computer in a manner that reduces error introduced by the computer processing, in accordance with one embodiment of the invention.

This specification presents solutions we have developed to address some of the problems that presently occur when a computer is used to attempt to solve a linear programming problem. For example, we present a solution herein to control the problem of incorrect results caused by the accumulation of computer error during a run of a computationally intensive simplex-like method for solving linear programming problems. Also, a solution is presented herein to solve the problem of one having to restart from the beginning in an attempt at solving a linear programming problem when one encounters changing constraints for the problem.

In accordance with one embodiment, a method referred to herein as the Virtual Simplex Method (VSM) is introduced. The VSM embeds the given linear programming problem to be solved within a larger linear programming problem we call the virtual problem or "h-problem" and produces a sequence of systems we call virtual problems that contain the original problem and are driven to have the same solution as the original system—even in the presence of computer errors in the computer computations. And VSM proceeds by pushing the virtual systems in a suitable direction (in a sense we'll discuss later) until we find an equivalent system for which the solution to both the virtual problem and the original problem are the same and are made with minimal error.

The value of the h-problem is that VSM is able to carry out its computation in a stable way: it will not fail. Simplex-based methods fail when the set of basic variables in hand does not support a basic feasible solution because of computer error. In contrast to prior methods, when VSM is faced with such a "fail" situation, the VSM introduces a new basic virtual variable to provide a set of basic variables that does support a basic feasible solution.

As long as the h-problem offers sets of basic variables that include virtual variables, VSM does not offer a solution for the optimality problem, let alone a feasible solution. It drives toward finding a basic set of variables that includes no virtual variables. When that is achieved the basic solution offered for the enlarged problem is also a basic solution for the optimality problem. VSM is designed to drive toward finding such a basic solution or determining that such a solution does not exist.

VSM is not guaranteed to find an optimal solution that is more accurate than can be obtained by computationally sound numerical methods. A difficulty with versions of the simplex method currently in use is that decisions made by those methods are often in conflict with sound numerical practice. In contrast, VSM introduces virtual variables whenever a decision might be made or has been made that would compromise feasibility.

The VSM uses a sequence, $E_1, E_2, E_3, \ldots, E_k$, of what we call E matrices such that $E_i A x = E_i B$. In the VSM, any imprecision in computing an E matrix that comes from computer errors will still produce an invertible factor matrix (the E matrix) that is acceptable in the VSM. That is, the invertibility of the E matrix is all that is required to assure that the original system and the virtual system have the same solution. The VSM can devote its attention to getting a better choice for the E matrix. The choice may be better in either the sense that the E matrix is more nearly an inverse matrix for a sub matrix of A or that the value of the objective function is more nearly optimal. As we have implemented VSM, these two types of improvements are interspersed. The VSM proceeds, then, by creating a sequence of these invertible factor matrices, $E_1, E_2, E_3, \ldots, E_k$. Each of these matrices $E_i$ could be used to create a problem $E_i A x = E_i B$ which is equivalent to the original problem $Ax=B$; that is, the systems $E_i A = E_i B$ have identically the same solutions as $Ax=B$; however, the VSM never need actually calculate any of the systems $E_i A x = E_i B$, but, instead need only hold the factor matrix $E_i$ in registers.

The approach of the VSM is to improve the matrices $E_i$ until the system $E_i A x = E_i B$ can be solved in a straightforward manner by producing a final representation that allows the solution to be read off in an obvious way. When that happens we also have a solution to the original system $Ax=B$. The measure of the error, as we define error, still inherent at any point in this process is the measure of the difference between the $E_i$ we have and an exact inverse for A; it is the difference $\Delta = EA - I$ which can always be calculated in principle. We will discuss this further below. As disclosed herein, $\Delta$ can be reduced until the error is as small as the condition of the vertex allows.

With this observation the distinction between the VSM and existing versions of simplex-like methods can be made clear: the strategy of the VSM is to create a sequence of factor matrices $E_i$ which come ever-closer, in the sense of minimizing the size of $\Delta = E_i A - I$, to producing an answer which is as close as is possible to the exact solution to the original problem $Ax=B$ by being able to read off the solution of $E_i A x = E_i B$. The (imperfectly-achieved) strategy of existing simplex-like methods is to compute a sequence of systems $A_i x = b_i$ which give approximately-equivalent representations of the original problem throughout the run. Because of the inevitable computer errors in the calculations of the coefficient matrices $A_i$ of these systems, these existing simplex-like methods are always inexact and the errors accumulate in the computer as these methods proceed. These existing methods create new systems that are not exactly equivalent to the original problem and for which the errors that are introduced by the computer processing propagate and typically become larger as the run proceeds. The errors in the answers these existing methods produce are of unknown size, and may even be large enough to invalidate the solution. Furthermore, although these errors can be estimated, they are not reduced during the run of the method. Further background on existing simplex-like methods can be found in *Linear Programs and Related Problems* by Evar D. Nering and Albert W. Tucker, Academic Press, Inc. 1993 which is hereby incorporated by reference in its entirety and for all purposes.

The Stored Inverse form of the Revised Simplex Algorithm (SIRSA) (and the related Implied Inverse form of the Revised Simplex Algorithm (IIRSA) in which the sequence of pivot operations required to compute E, rather than E itself are stored) has a technique which is superficially similar to the representation of the problem by the VSM in that the SIRSA holds a factor matrix E in memory and calculates only the parts of EA it needs to make a decision at any point in the method. In that sense, the SIRSA has a virtual copy of the system EAx=EB in the same way that the VSM does. But there is an important difference in the way SIRSA and the VSM exploit this virtual representation: VSM continually attempts to improve the accuracy of the matrices $E_i$ to create a system $E_iAx=E_iB$ for which $\Delta=E_i-I$ is reduced by the technique called the Pivot-in-Place (PIP) (see below); the SIRSA does not, and as a result the systems the SIRSA (and other simplex-like methods) are working on (whether virtually or not) may drift away from being completely accurate because of accumulated computer error.

A. Terminology

The following brief explanations of some of the terms used in the specification may be helpful for the reader:

*A*—the italicized version of a variable is typically used herein to designate a matrix, as will be readily understood by one of ordinary skill in the art.

Artificial variable—a variable is said to be artificial if it is required to be zero.

Auxiliary problem—the problem constructed in Phase I of the simplex algorithm.

Basic column—The basic columns are the columns that are associated with basic variables—collectively the list of basic columns or basic variables is called a basis. A basic column should be a unit column, a column that is all zeros except for a 1 in the row with which the basic variable is associated. In practice columns corresponding to basic slack variables and basic virtual variables, variables created by VSM during a run, are exact unit columns Columns of decision variables, variables given in the original data, are computed and are usually only approximately unit columns because of computer error. VSM tries to make these columns as near to unit columns as computer error allows. We also keep a list of the basis, that is, the basic variables (and therefore the basic columns are known at all times).

Basic feasible form—the form to which an h-problem is initialized at the beginning of a run. The h-problem is maintained in this form throughout a run. A linear programming problem is in Basic Feasible Form, for example, when all of the following conditions apply:

1. Each constraint is associated with a variable, which is called a basic variable. Initially, the slack variables are basic and each slack variable is associated with the row and column of its index.
2. The columns associated with basic slack variables and basic virtual variables are unit columns. All entries in the columns are zeros except for a 1 in the row with which it is associated. VSM attempts to make the columns associated with basic decision variables as close to being unit columns as computer error allows.
3. The entries in the b column associated with canonical basic variables are non negative.
4. There are no basic artificial variables.

Basic set—the set of basic variables.

Basic solution—a solution obtained by assigning zeros to the non-basic variables.

Basic variables—a variable associated with a constraint. There is one basic variable associated with each constraint. In turn, basic columns are those columns associated with basic variables.

Canonical linear program—a formulation of a linear programming problem in the form Ax+y=b which is also subject to the conditions that y≥0 and x≥0.

Canonical variables—variables required to be non negative.

Computer error—A computer can easily represent the number 1 exactly using its registers—it simply puts in a single 1 bit in the appropriate register and zeros elsewhere—there is no discrepancy between the number 1 and the number that the computer stores. But it cannot represent the number ⅓ exactly; it can put the equivalent of 0.333333333333333 in its memory (for some number of the digits '3', depending on format of the computer registers, which determines the precision that's possible), but that is not exactly ⅓. In fact, this particular example would be off by (⅓)(E-15), a very small number, to be sure, and one we usually ignore safely, but in linear programming problems this slightly incorrect value will probably be used again in other calculations later, and in some cases it may be used thousands or even millions of times in the solution of a linear programming problem, and this "computer error", which was once small, may, under some circumstances, propagate and grow, what we call the accumulation of computer error, to the point that it actually contaminates and invalidates the solution the computer produces—it can actually cause the computer to give an erroneous result or to be unable to get to a result. The standard by which computers hold and represent floating point numbers (like ⅓) is called the IEEE-754-2008 Floating Point Standard. IEEE-754-2008 is the standard by which nearly all computers represent numbers.

Decision variables—Decision variables are the variables that occur in the linear objective function equality and also the variables that appear in any of the initial constraints.

Duality equation—the duality equation shows the relationship between the variables of the primal problem (the f problem) and the variables of its dual, the g-problem, and shows that if they are both feasible they have the same optimum, one a maximum and the other a minimum. There is a correspondence between the basic variables of one and the non basic variables of the other: in each pair, one variable is basic for its problem and its dual is non basic for its problem.

Dual problem—is the dual of the optimality problem (the f-problem). It is often referred to as the g-problem, herein. The g-problem and f-problems are duals of one another.

E Matrix—An invertible matrix that connects the given constraints, Ax=B with the equivalent constraints EAx=EB. In this context the computations are assumed to be exact and the two sets of constraints have the same solution set.

EMatrix (without a space)—The EMatrix is an embodiment of the E matrix in hardware and software. It is subject to computer errors. It is designed to improve computational speed, efficiency, and accuracy.

Feasible; feasible solution—A problem has a feasible solution (or is said to be "feasible") when a solution to the problem y=Ax+b also satisfies the feasibility conditions. Namely, canonical variables satisfy the conditions x≥0 and y≥0; and all artificial variables are zero. The h-problem is feasible by construction—and is continuously maintained and updated by VSM so that its basic solution is feasible. A system of equations is said to be feasible if the system of equations has a feasible solution. If either the f-problem or the h-problem fails to have a feasible solution neither problem has an optimal solution.

Feasibility Specifications—In addition to satisfying the constraints imposed by equations or inequalities, variables may be required to satisfy feasibility specifications. If they are required to be non negative they are said to be canonical. If they are required to be zero they are said to be artificial. If there are no additional conditions imposed they are free. The constraints will typically have solutions that do not satisfy the feasibility specifications.

Free variables—a variable is said to be free if no constraint is placed on it.

Invertible matrix—an n×n matrix A is called invertible if there exists an n×n matrix B such that AB=BA=I wherein I is the identity matrix. An invertible matrix is also called a non-singular matrix.

IIRSA—is the acronym for the Implied Inverse form of the Revised Simplex Algorithm.

Non basic variables—a variable is non basic if it is not a basic variable.

Objective function—a linear function defined in the optimization problem to be maximized or minimized, usually called f for the primal problem, g for the dual problem, and h for the virtual problem.

Optimal solution to a linear programming problem—this is what we call a solution to the linear programming problem; it is a feasible solution that is also optimal.

Optimality problem—sometimes referred to as the original problem or f-problem or its dual the g-problem, it is the problem that is being optimized.

Pivot column—the pivot column is the column that contains the selected pivot element.

Pivot exchange—a step in a simplex-like algorithm in which one variable is deleted from the set of basic variables and is replaced by another variable. In VSM the rules for selecting the variables to be exchanged are quite different from those used in versions of simplex-like methods.

Pivot row—the row chosen for performing a pivot operation.

Pivot operation (pivot exchange)—simplex-like methods proceed by a sequence of stages each of which is characterized by a set of basic variables. For example, in a succession of steps from one stage to the next the method may select a variable that will enter the set of basic variables and a variable that will leave the basic set. This is the sense in which a pivot exchange is an 'exchange'. The method may use rules to select the entering variable and the leaving variable. The associated pivot operation is the set of arithmetic calculations that are used to cast the representation of the problem in a form in which the columns associated with the basic variables are unit columns or nearly unit columns.

Selectors—Arrays used in the selection of a pivot column. The numbers playing this role in versions of simplex-like methods are often called prices. Those other simplex-like methods use a single array. VSM uses two arrays, one an array of coefficients of the h-problem and the other an array of coefficients of the f-problem. For this reason VSM works on both-problems and chooses a pivot column depending on which array provides the decision data.

Selector Processors—the processors that handle the −1 and 0 rows of the Ematrix wherein the −1 and 0 rows hold the h-problem objective and the f-problem objective, can be specially designated (as opposed to the other EMatrix rows, which are not necessarily addressable) in one embodiment of the invention, so that the −1 and 0 rows can be accessible to the Conductor processor in order for it to be able to work on finding an eligible column in the A Matrix while it is waiting for the EMatrix to complete its methods; this can result in a speed-up of the solution method.

SIRSA—is the acronym for the Stored Inverse form of the Revised Simplex Algorithm. The revised simplex algorithm is a version of the simplex algorithm designed to reduce the demand on computer resources.

Solving a Linear Programming Problem—By "solving a linear programming problem" we mean "finding an optimum value for a (single) linear equation called the objective function, subject to having to meet a set of linear constraints (which are not necessarily equations but in many cases—actually most cases in practice—are given by inequalities) on the values of the variables that achieve that optimum (these variables are called the decision variables of the problem).

Unbounded linear programming problem—when the primal problem is feasible but is unbounded there is no optimal solution. If the primal problem is feasible, a necessary and sufficient condition for the problem to be unbounded is for the dual problem to be infeasible (see *Linear Programs and Related Problems* by Evar D. Nering and Albert W. Tucker, Academic Press, Inc. 1993, the section on The Theorem of the Four Alternatives), and we say that the primal problem is "unbounded". This is a theoretical concept that is not likely to occur in practice. If a corporation is trying to maximize its profits it is unlikely that they are unbounded. If a corporation is trying to minimize its costs it is unlikely that they can make their costs negative.

Virtual variable—virtual variable is a decision variable of the (virtual) h-problem which is not a decision variable of the primal f problem.

B. The Virtual Problem

In accordance with one embodiment of the invention, a problem is constructed as the Virtual Problem or h-problem, at the start of a run. The virtual problem (also referred to herein as the h-problem) resembles superficially the auxiliary problem constructed in two-phase versions of the simplex algorithm, but it plays a significantly different role. The Virtual Simplex Method or VSM is a single phase method and, once created, the virtual problem exists throughout a run of VSM.

Other simplex-like methods run into problems when they obtain a set of basic variables for which the basic solution is not feasible. The basic set does not support a feasible solution. Furthermore, these versions have no way of detecting when this occurs (the data they see do not reveal the problem) nor can they take any corrective action other than to start from the beginning taking care to use a different sequence of pivot exchanges. By analogy, when these methods stray off the path that leads to an optimal solution they do not realize that they are off the path and they have no way of finding their way back. By contrast, when VSM takes a step that might stray off the path it creates a basic virtual variable that allows VSM to find its way back to the path.

To enable an effective and simple implementation VSM casts the objective function for the virtual problem (or h-problem) as an additional row in the matrix representing the original linear programming problem, and adds additional virtual columns for virtual variables that VSM creates at intervals during a run. As a metaphor the virtual problem contains, or encapsulates, the given optimization problem. Because the calculations involving these extra variables are virtual there are no computational errors involving them. They pose no danger to the integrity of the run. VSM uses the virtual problem as a safety net that prevents failure when such a possibility might occur.

Like all versions of the simplex algorithm, during a run of VSM the presentation of the optimization problem will be expressed in terms of basic sets and associated basic solutions. A difference is that in VSM the basic sets may include basic virtual variables. In these situations VSM does not offer a basic solution for the optimization problem. The selection rules for VSM are designed to perform pivot exchanges that make basic virtual variables non basic. During a run there will be occasions where the basic set includes basic virtual variables and occasions where the basic set includes no basic virtual variables. When the basic set includes no basic virtual variables, the basic solution for the virtual problem and the basic solution for the optimization problem are identical.

The virtual problem (also known as the h-problem) is always feasible and always has an optimal solution by construction. If the optimal solution for the virtual problem includes basic virtual variable(s) the optimization problem is infeasible. If the optimal solution for the virtual problem includes no basic virtual variables, the optimal solution for the virtual problem is identical to the optimal solution for the optimization problem.

C. Error Control

Numerical analysis methods for dealing with computer error are sophisticated and extensively tested. The difficulty in applying these methods to linear programming problems is that the selection rules for simplex-like methods are not consistent with the recommended numerical methods. One method for compensating for that difference is to note the set of basic variables obtained as the solution and to restart the calculations from the beginning using sound numerical methods to obtain the same basic set. This is an expensive use of computer resources and requires beginning again from the starting point.

Simplex-like methods, as well as VSM, obtain an approximate answer by equating each basic variable with the entry in the b column of its constraint. Other simplex-like methods call this offered answer a basic solution. The problem is that the b column is not a solution. It is the right hand side (RHS) of a system of equations and the true basic solution for this set of basic variables is the solution obtained by setting the non basic variables equal to zero and solving for the basic variables. The term "basic solution" is so deeply embedded in the literature on linear programming that we do not propose trying to change the meaning of the term. But VSM realizes that the term refers to an approximation to the solution, not to a solution.

1. New Measure of Error

Numerical methods try to control computer error by minimizing the sizes of these errors as they occur in the sequence of calculations. In contrast, VSM takes a remedial approach to controlling computer error. In other simplex-like methods error is the difference between an offered answer and the exact solution. However, when solving a problem, the exact solution is not known so the error can only be estimated. VSM introduces a new measure of error. Though indirect, this measure of error can, in principle, be computed and it provides an estimate of the traditional error. Furthermore, VSM provides methods embedded in its implementation that control the size of this new measure of error by controlling the size of any specific norm of $\Delta$.

VSM computes the difference $\Delta = EC - I$ where C is the sub matrix of A consisting of the basic columns and E is an approximate inverse of C. Since EC can be computed and I is exact $\Delta$ can, in principle, be computed. $\Delta$ is not in itself the error incurred in accepting the b column as an approximate solution but, if $\bar{b}$ is the exact basic solution and b' is the offered answer, $\bar{b} - b' = \Delta \bar{b}$. The smaller the entries in $\Delta \bar{b}$ (i.e., $\Delta$) the better b' is as an approximation of $\bar{b}$. The entries in $\Delta$ cannot be computed exactly. The smaller the entries in $\Delta$ are the fewer non zero significant digits the entries have that can be represented in a computer. If E were computed exactly the entries in $\Delta$ would be zeros. Thus, the leading zeros are significant digits and the entries give an upper bound estimate of the order of magnitudes correctly. The value of this approach lies in the fact that VSM provides a practical method for doing the computations in such a way that the $\Delta$s will be as small as the condition of C allows. VSM can use $\Delta$ as a measure of error.

Ideally, E is the inverse of the sub matrix C made up of the basic columns of A. That is, let $EC = I + \Delta$. If E is close to being an inverse the entries in $\Delta$ will be small. VSM tries to keep the entries in $\Delta$ small. Since the entries in $\Delta^2$ are even smaller it is inviting to replace E by $E' = (I - \Delta)E$ to obtain $E'C = (I - \Delta)EC = I - \Delta^2$. This does not work because the entries in $\Delta$ have few significant digits when they are small. The associative law of matrix multiplication breaks down and $E'C = ((I - \Delta)E)C$ is not equal to $(I - \Delta)(EC) = I - \Delta^2$.

Let $\Delta_k$ be a matrix all of whose entries are zeros except for those in column k. Column k is identical to column k of $\Delta$. Then $\Delta = \Sigma_k \Delta_k$. Since the entries in $\Delta_k$ are small $(I - \Delta) \cong \Pi_k(I - \Delta_k)$. Instead of computing $(I - \Delta)E$ we compute $\Pi_k(I - \Delta_k)E$. One advantage is that the leading factors can be multiplied in any order or one can even use just some of the factors. The big advantage is that multiplying by $(I - \Delta_k)$ is almost the same as performing a pivot exchange with column k of $I - \Delta_k$ as the pivot column and the row containing $1 - \delta_{kk}$ as the pivot row. The only difference is that in computing $(I - \Delta_k)E$ row k is multiplied by $1 - \delta_{kk}$ and in the pivot exchange row k is divided by $1 + \delta_{kk}$. For small $\delta_{kk}$ the result is almost the same.

2. Pivot-in-Place, PIP

Pivot operations are well understood by those of ordinary skill in the art. For example, pivot operations are discussed in the text *Linear Programs and Related Problems* by Evar D. Nering and Albert W. Tucker, Academic Press, Inc. 1993 as shown on pages 51, 86 and 146. In accordance with one embodiment of the invention, a new operation which we refer to as the Pivot-in-Place is introduced.

If $A_k$ is the kth column of A and a basic column it is one of the columns of C and $EA_k$ should produce a unit column $EA_k$ is the non zero column of $\Delta_k$. If VSM chooses this column as a pivot column in an effort to process the h-problem so as to obtain an optimal solution, the associated basic row is likely to be selected as the pivot row since the entry in that row, $1 + \delta_{kk}$, is the largest entry in the column. However, if the errors are large or if the column has been edited due to new conditioning the basic row might not be selected. That is, the basic set may not support a basic feasible solution. If that were to occur, completing the pivot exchange would produce two rows associated with the same basic variable.

To avoid this possibility, VSM performs a ForceNonBasic method (explained in more detail below) before using the $EA_k$ column as a potential pivot column. That is, whenever VSM scans a basic column it performs a ForceNonBasic method and then treats the resulting non basic column as a potential pivot column We call this operation, a ForceNonBasic followed by a pivot operation on the column, i.e., a Pivot-in-Place (PIP).

As implemented in VSM a PIP is optional in that it does not have to be used continuously throughout a run. A PIP can be disabled or enabled at any time during a run. If the problem is dynamic with changing coefficients, PIP is preferably enabled at all times. If the problem is static, a possibility is to complete the run with PIP disabled and then to implement PIP during the final circuit.

PIP is approximately as effective as reinverting that is used in the older technique of the Simplex Algorithm (i.e., starting anew and making fewer pivots once you know the end result and by virtue of doing fewer calculations hoping to have less error) and approximately as costly in use of computer resources. It has the advantage in that it does not require interrupting the flow of the run to start anew. It can be seamlessly embedded in VSM. It has the effect of severing the accumulation of computer error. Whatever errors have been incurred earlier become irrelevant and the only computer error present is the error involved in the arithmetic in the execution of PIP such as that due to round-off error.

3. bUpdate, ForceFeasible

Starting with the original system of constraints $Ax=b$ a simplex-like method produces a sequence of systems that would be equivalent to the original system if the computations were carried out exactly. However, a system in the form $EAx=b'$ obtained during the run will not be exactly equivalent to the original system. The system could be restored to equivalence by replacing $b'$ by $EB$ to obtain $EAx=EB$. While this would be equivalent to the original system the entries in $EB$ might fail to be non negative. When this occurs the run is said to have gone infeasible; the run fails.

After replacing $b'$ by $EB$ VSM examines the entries in $EB$ to determine if any are negative. If there are negative entries VSM executes a ForceFeasible. This restores the virtual problem to basic feasible form at the expense of introducing a virtual variable. The run can proceed. We refer to this method as a "bUpdate."

PIP and bUpdate have the advantage that they are special forms of a pivot operation and they can be embedded seamlessly in VSM. bUpdate ensures that the current representation of the problem is equivalent to the original representation. PIP, the method used to control the sizes of the entries in $\Delta$, can also be invoked at any time during a run. The only errors are those that occur in carrying out bUpdate and PIP.

D. Dynamic Data Changes

VSM was designed to monitor, for example, a dynamically changing problem such as a financial portfolio or an electric power grid. PIP and bUpdate were discussed above as responses to computer error. If EA or EB is not what is expected it does not matter whether that difference is due to computer error or deliberately changing data. That is, there is no conceptual difference between computer error and changing data. If the data in a column are changed it will be handled the next time the column is scanned if it is non basic, and it will be corrected by a PIP if the column is basic. If the data in B is changed it will be handled the next time a bUpdate takes place.

There have been many proposals for dealing with changed data in methods based on the Simplex Algorithm after a solution has been obtained. This is called post-optimal analysis or sensitivity analysis. Techniques for doing this are invariably ad hoc with the analysis depending subjectively on the actual numbers encountered and the form of the solution. To do more than this involves, in essence, restarting the method again from the beginning after the new data have been inserted.

By contrast, the Virtual Simplex Method can handle dynamic changes in the data. That means it can not only handle changes in the data after a solution has been found (without restarting the solution process from the beginning), but it can also contend with changes in the data for the problem during the course of the run of the solution process (without restarting the solution process from the beginning).

In effect, the same ideas that make the Virtual Simplex Method robust with respect to error control permit the VSM to handle changes in the data during the actual run of the method—any differences between the original and subsequent values for the data are treated as if the new data has caused an "error" in the E matrix (the data are different from what they would have been if the new value(s) had been there from the beginning), but the "error" is managed by the same error-correcting provisions of VSM that control the error $\Delta=EA-I$, so it handles the changing values in A or b without difficulty.

This is a major innovation, particularly when you consider that in some problems the data that are in the original system $Ax=b$ represent a particular state at one instant, only, of a system that is intrinsically dynamic—it might, for instance, represent unstable prices or availability of commodities (e.g., stock prices) that may change very frequently. In other methods, the only real attack that would work in those situations would be to re-run the problem again from the beginning using the new data—so if the solution cannot be found before the data changes, the run is probably worthless. But the VSM can simply modify the data in the original presentation and continue running—this will frequently result in the VSM finding the solution in many fewer steps and in a shorter time than required by traditional methods.

The ability to handle dynamically-changing data is believed to be an entirely new idea for this class of methods. No other method we know of appears to even attempt to handle this situation, which is significant because many of the actual problems they are asked to solve are inherently dynamic. This leads to a completely new concept of how to use VSM: the method can continue to run even after it has achieved a solution to the original problem; as soon as a price (or other data element) changes, the new data can be entered in the original matrix and the VSM will solve the new problem by continuing after a solution of the original problem has been obtained, a technique that is believed to usually produce a solution to the new problem in significantly fewer steps and in a much shorter time than would be required by using traditional methods. In contrast, previous methods input the changed condition into the original problem and try to solve the revised problem from the beginning.

Ii. Mathematical Foundations

The mathematical foundation will now be discussed in more detail.

A. Linear Programs

We want to maximize (or minimize) the objective function $$f=cx+d \qquad (1)$$

where $$Ax \leq b \qquad (2)$$

subject to the condition that $x \geq 0$.

We convert this formulation to a system of equations in the form $$Ax+y=b \qquad (3)$$

by introducing the slack variables y and imposing the condition that $y \geq 0$. This form, with $x \geq 0$ and $y \geq 0$, we call a "canonical linear program." We say that the variables x and y satisfying these inequalities are "canonical variables." We divide consideration of solving this problem into two logical steps. We can assign any values we please to x and solve for y=−Ax+b. Among the possible solutions a solution that also satisfies the conditions x≥0 and y≥0 is called a "feasible solution." We try to find a solution that is feasible. If the system of equations has a feasible solution the system is said to be "feasible." If the problem is feasible we then try to find a feasible solution that maximizes f. The linear program can fail to have an optimal solution in two ways: 1) the equations may have no feasible solution or 2) the system may be feasible but the set of feasible values off is unbounded. See *Linear Programming and Related Problems*, Theorem 5.38 at page 183.

B. The Dual Problem

For every linear program in this form there is a closely associated linear programming problem called the dual problem (that is, dual to the original problem, which is called the primal problem or f-problem), which is to minimize the linear objective function g, where $$g = vb + d \quad (4)$$

subject to the condition $$vA - u = c \quad (5)$$

where u≥0 and v≥0.
The relation $$g - f = vb - cx = v(Ax+y) - (vA-u)x = ux + vy \quad (6)$$

is called the "duality equation." Since ux+vy≥0 for canonical variables this implies that $$f \leq g \quad (7)$$

and that max f≤min g.

If both solutions are feasible a sufficient condition for optimality is that ux+vy=0. That is, for every pair of dual variables one or the other is zero. A pair of dual solution that satisfy this property, whether feasible or infeasible, is said to be complementary. If both-problems have optimal solutions their optimal solutions will necessarily be complementary.

The formulation of the duality equation and its consequences are given in detail in *Linear Programs and Related Problems* by Evar D. Nering and Albert W. Tucker, Academic Press, Inc. 1993. The theorems and facts quoted in the following exposition are explained and proved there.

If a linear program and its dual problem are both feasible then both problems have optimal solutions and their optimal values are equal. If one problem is feasible and the other is not, the feasible problem is unbounded. The duality equation is true under all conditions but the conclusions about optimality depend on the inequality ux+vy≥0.

This suggests that we can preserve the conclusions about optimality by relaxing the feasibility constraints as long as we preserve the inequality. We define a variable to be free if no constraint is placed on it. That is, it is free to take on any value and is not constrained (required) to be canonical (a canonical variable is one that is required to be ≥0). And we define a variable to be artificial if it is required to be zero. We say that two variables paired in the duality equation satisfy dual feasibility specifications if both are canonical, or that if one is free its dual is artificial. In this way we generalize the statements about optimality to any pair of dual problems for which dual variables satisfy dual feasibility specifications. With this more general definition of feasibility it is still true that if both-problems are feasible they both have optimal solutions and the optimal solutions are complementary.

The relation between a dual pair of linear programming problems is symmetric. Either can be taken as the primal problem and the other as its dual. The method we describe may terminate with an optimal solution for both the primal problem and the dual problem, or with a determination that the problem is infeasible, or with a determination that the problem is feasible and unbounded.

Considerations Concerning Systems of Linear Equations as a Special Case of Linear Programming An ordinary system of linear equations can be cast in this form by taking f=c=0 and requiring y to be artificial and letting x be free. In the terminology of linear programming such a system of linear equations always has a solution if it is feasible because the dual feasibility specifications would require that u be artificial and v be free. The dual system vA=u is always feasible since we can take v=0 no matter what the feasibility specifications are, so the dual problem has a solution (which may be unbounded). The question is whether the system of linear equations has a feasible solution. The system of linear equations Ax=b for x free has a solution if and only if the system vA=0 and g=vb is bounded. In traditional linear algebra we show that a system of linear equations fails to have a solution by using a method that fails to find a solution. But in our context in the subject of linear programming we can show that the system of linear equations fails to have a solution by showing that the dual system is unbounded. But since the duality equation would imply that f=g for dual optimal solutions and f=0 it is sufficient to show that g>0 for a feasible solution of the dual problem. This gives us a positive criterion for a negative conclusion.

C. Linear Systems

To provide the notation and terminology for the method we will cast the linear program in the form of a single system of equations which we call a "linear system." Write the equation f=cx+d in the form $$(-d)(-1) + (-f) + 0y + cx = 0 \quad (8)$$

and the equation Ax+y=b in the form $$b(-1) + 0(-f) + Iy + Ax = 0 \quad (9)$$

We can now combine all this into a single matrix equation with the coefficient matrix $$\begin{array}{cccc} -1 & -f & y & x \end{array} \quad (10)$$
$$\begin{pmatrix} -d & 1 & 0 & c \\ b & 0 & I & A \end{pmatrix} = 0$$

The equations (8) and (9) are implied by retaining the matrix in (10) and remembering the entries that are on the top border. The notation can be further simplified by combining the first column containing −d and b into a single column that we denote by B, combining the next two columns into a single column that we denote by I and combining the last column into a single column we denote by A. In that notation equation (10) takes the form $$\begin{array}{cc} -1 & yx \end{array}$$

$$(B I A) = 0 \quad (11)$$

If the original matrix had m rows indexed from 1 to m the matrix we now have has m+1 rows indexed from 0 to m. We merely have to remember that row 0 represents the objective function and that f=−y$_0$=0. For that reason we call that row the "objective row."

D. Basic Solutions

Since each $y_i$ appears in only one equation with the coefficient 1 it is easy to find solutions. Assign any values you wish to the $x_j$'s and compute the $y_i$'s. Among such solutions the easiest to obtain is to assign $x=0$. In that case each $y_i=b_i$ and $f=d$. This solution is called a basic solution. If the computation is exact it is a solution. If the computation has errors it is merely the right hand side (RHS) of a system of equations and setting $y_i=b_i$ yields only an approximate solution.

It is not difficult to find other solutions. In any column not a basic column look for an entry $a_{rs}a_{ij}$ that is non zero in that column (where "r" and "I" represent rows and "s" and "j" represent columns) Divide that row by $a_{rs}a_{ij}$ to make that entry 1. Then subtract multiples of that row from the other rows to make the other entries in that column zero. That is, $$a'_{ij}=a_{ij}-a_{rj}a'_{is}, i \neq r$$

That column will become a unit column and the column that had a 1 in that row will no longer be a unit column. These operations carry out the arithmetic associated with a pivot exchange. The selected column is the pivot column and the selected row is the pivot row. The important observation here is that the calculations made in the first step can be carried out simultaneously, and the calculations made in the second step can be carried out simultaneously. This is the basis for the design of the massively parallel design obtained in VSM.

We can again assign 0 to all the variables corresponding to columns other than the unit columns and compute the values of the variables corresponding to the unit columns.

The columns associated with basic variables are basic columns. If the arithmetic involved in the pivot exchanges is exact the basic columns would be unit columns A solution obtained by assigning zeros to the non basic variables is called a basic solution. When a pivot operation is performed one variable that was non basic becomes basic and one variable that was basic becomes non basic. For this reason a pivot operation is also called a pivot exchange.

The importance of this concept is contained in the following three theorems.

- If a linear system has a feasible solution it has a basic feasible solution.
- If a linear system has an optimal solution it has a basic solution that is optimal.
- We can get from one basic solution to any other basic solution by a sequence of pivot exchanges.

Thus, it is possible to design a method to find feasible solutions and to find optimal solutions by sorting through the basic solutions.

We have chosen to represent a linear system with a matrix in expression (11) because it is best for the computations we will describe but it does not show the symmetry between the primal and dual problems. The Tucker tableau, described in *Linear Programs and Related Problems* by Evar D. Nering and Albert W. Tucker, Academic Press, Inc. 1993 displays the symmetry effectively. Here, we will be content to describe how to find the basic and non basic variables and their values from the representation (11).

The duality equation combines pairs of variables from the primal and dual problems. In each pair one variable is basic for its problem and its dual is non basic for its problem. The variables for the dual problem are not displayed. They are implied. The basic variables of the dual problem are the non-basic variables of the primal problem; so the basic variables of the dual problem will be 0 for the optimal solution of the primal problem. The variable of the primal problem associated with a basic column is basic for the primal problem. Its implied dual variable is non basic in the dual problem. A variable of the primal problem associated with a non basic column is non basic and its implied dual variable is basic. For a basic solution we assign zero to all non basic variables for both the primal problem and the dual problem. Thus the two dual basic solutions are complementary. For a maximization problem the coefficients in the objective row in basic columns are the negatives of the values of the corresponding dual basic variables. For a minimization problem the coefficients in the objective row in basic columns are equal to the values of the corresponding dual basic variables. Thus for a maximization problem optimality for both-problems is achieved when all entries in the objective row are non positive, i.e., less than or equal to zero. For a minimization optimality is achieved when all entries in the objective row are non negative, i.e., greater than or equal to zero.

Let us illustrate this with an example. Consider the linear program: Maximize $$f=10x_1+5x_2+5.5x_3+20 \tag{12}$$

where $$30x_1+10x_2+50x_3 \leq 1500$$

$$5x_1+3x_3 \leq 200$$

$$2x_1+x_2+3x_3 \leq 12 \tag{13}$$

When cast as a linear system it is represented by the matrix from equation (11)

$$\begin{bmatrix} -20 & 1 & 0 & 0 & 0 & 10 & 5 & 5.5 \\ 1500 & 0 & 1 & 0 & 0 & 30 & 10 & 50 \\ 200 & 0 & 0 & 1 & 0 & 5 & 0 & 3 \\ 12 & 0 & 0 & 0 & 1 & 2 & 1 & 3 \end{bmatrix} \tag{14}$$

which could also be represented with column and row labeling as:

|       | b    | −1 | $y_1$ | $y_2$ | $y_3$ | $x_1$ | $x_2$ | $x_3$ |
|-------|------|----|-------|-------|-------|-------|-------|-------|
| f = g | −20  | 1  | 0     | 0     | 0     | 10    | 5     | 5.5   |
| $y_1=$ | 1500 | 0  | 1     | 0     | 0     | 30    | 10    | 50    |
| $y_2=$ | 200  | 0  | 0     | 1     | 0     | 5     | 0     | 3     |
| $y_3=$ | 12   | 0  | 0     | 0     | 1     | 2     | 1     | 3     |

After several pivot exchanges we might obtain $$\begin{bmatrix} -620 & 1 & 0 & 0 & -5 & 0 & 0 & -19.5 \\ 60 & 0 & -0.2 & 0 & 3 & 0 & 1 & 5 \\ 30 & 0 & 0.1 & 0 & -1 & 1 & 0 & 0 \\ 50 & 0 & -0.5 & 1 & 5 & 0 & 0 & 3 \end{bmatrix}$$

(15) which could also be represented with column and row labeling as:

|       | b    | −1 | $y_1$ | $y_2$ | $y_3$ | $x_1$ | $x_2$ | $x_3$ |
|-------|------|----|-------|-------|-------|-------|-------|-------|
| f = g | −620 | 1  | 0     | 0     | −5    | 0     | 50    | −19.5 |
| $x_2=$ | 60   | 0  | −0.2  | 0     | 3     | 0     | 1     | 5     |
| $x_1=$ | 30   | 0  | 0.1   | 0     | −1    | 1     | 0     | 0     |
| $y_2=$ | 50   | 0  | −0.5  | 1     | 5     | 0     | 0     | 3     |

The basic columns determine the values of their basic variables. We get $x_2=60$, $x_1=30$, and $y_2=50$. The basic columns are the columns of $x_2$, $x_1$, and $y_2$. The other columns are, therefore, non basic for the primal problem, so $y_1$, $y_3$, and $x_3$ are non basic.

Each non basic variable for the primal problem is associated with a non basic column. As noted above, for a maximization problem, the coefficients in the objective row in basic columns are the negatives of the values of the corresponding dual basic variables. By implication, the basic variable of the dual problem is also associated with that column Its value is the negative of the entry in the objective row of that column. This gives the variable dual to $y_1$ the value 0, the variable dual to $y_3$ the value 5, and the variable dual to $x_3$ the value 19.5. Since both basic solutions are feasible they are both optimal.

We will display these results in a table of the form $$f=gy1y2y3x1x2x3$$

primal 620 50 30 60 dual 620 0 5 19.5 (16)

which with column and row labeling could also be represented as:

|  | f = g | $y_1$ | $y_2$ | $y_3$ | $x_1$ | $x_2$ | $x_3$ |
|---|---|---|---|---|---|---|---|
| primal | 620 |  | 50 |  | 30 | 60 |  |
| dual | 620 | 0 |  | 5 |  |  | −19.5 |

From the duality equation we see that g−f=ux+vy=0 since one or the other of each dual pair is non basic and, therefore, zero. In this case we have f=g=620.

E. Virtual Linear Systems

Consider the linear system $$-B+Iy+Ax=0 \quad (17)$$

If this problem has in constraints, the matrix A has m+1 rows, including the objective row indexed from 0 through m. We adjoin an additional row, indexed −1, which we call the virtual row. This row is initially all zeros so that the new representation still represents the given optimality problem. This is the nucleus of the virtual problem. From time to time in a run, the Virtual Simplex Method (VSM) will add columns, referred to as virtual columns, and their associated canonical virtual variables. When a new virtual column is created as a non basic column it will have a 1 in the virtual row. Thus, the virtual row represents a function that is the sum of the virtual variables.

We introduce an (m+2)×(m+2) matrix E. Initially, this matrix is an identity matrix. If we multiply equation (17) on the left by E we obtain the linear system $$(-E)B+Ey+EAx=0 \quad (18)$$

The additional row represents the virtual objective function in the same sense that the top row of the system (17) represents the objective function of the given optimization problem. When VSM initializes the imported problem it constructs the E matrix and introduces virtual variables and appropriate virtual columns to make the virtual problem feasible.

Because of the way the virtual objective function is constructed, the virtual objective function is always the negative of the sum of the virtual variables. Since the virtual variables are canonical the virtual objective function is always non negative. VSM treats the virtual objective function as a minimization problem that will always have an optimal solution. Alternatively, the virtual objective function could be treated as a maximization problem. If at any point in a run the basic solution of the virtual problem includes no basic virtual variables the virtual objective function will be identically zero and the basic solution of the virtual problem will also yield a basic solution of the optimization problem. If that occurs the optimization problem will be feasible because the virtual problem is feasible. If the optimal solution of the virtual problem contains no basic virtual variables the optimal solution of the virtual problem will also be an optimal solution of the optimization problem. The advantage in working the virtual problem instead of working the optimization problem is that the virtual problem is feasible immediately after initialization so there is no initialization phase or what is often referred to as "Phase I" in the use of the Simplex Algorithm. Rather, VSM is a single phase method.

1. ForceFeasible

In accordance with one embodiment, virtual variables and virtual columns are created when needed to maintain the representation of the virtual problem in a form that is stable and robust. No other linear programming method, such as the Simplex Algorithm, operates this way. When VSM detects negative entries in the b column it can initiate a ForceFeasible operation. VSM creates a new column with all zero entries except for a 1 in the virtual row and −1's in the rows with negative entries in the b column. This new column is selected as a pivot column VSM selects as a pivot row the row in which the negative entry is smallest in accordance with one embodiment. When the pivot exchange is performed the entries in the b columns will all be non negative and the virtual problem will have a new basic virtual variable. When a new problem is imported VSM looks for negative entries in the b column and executes a ForceFeasible if it finds any. This assures that the initial basic solution for the virtual problem is feasible.

2. bUpdate

A problem that occurs in other simplex-like methods is that the computation can go infeasible. This is the result of the accumulation of computer error to the point when it thinks the basic solutions are feasible while they are, in fact, infeasible. This means that the problem that is being worked is not equivalent to the original problem. In accordance with one embodiment, VSM copes with this possibility by occasionally replacing the b column by EB. Before this replacement VSM is working the problem EAx=b where the entries in the b column are non negative. After the replacement VSM is working the problem EAx=EB. The problem is now equivalent to the original problem. If any entries in EB are negative VSM executes a ForceFeasible to restore the representation to feasible form. This operation, which we call bUpdate, prevents the failure that would otherwise be the result of the computer error. A bUpdate can be performed as often as desired.

3. ForceNonBasic

In accordance with one embodiment, if there are any equality constraints artificial slack variables will be created when the problem is imported. These are made non basic. VSM can create a column with a 1 in the virtual row and a 1 in the row of the basic artificial variable. All other entries in the column are zeros. VSM selects the column as a pivot column and the row of the artificial variable as the pivot row. VSM then executes a pivot exchange. After the pivot exchange the artificial variable is non basic and there is a new basic canonical virtual variable in its stead. This pivot exchange can be executed very efficiently. Just subtract the row of the basic variable from the virtual row. This operation is called ForceNonBasic. There are other reasons for using ForceNonBasic. Errors or changes in the data in non basic columns do not affect the basic solution since these variables are assigned zeros in a basic solution. If a basic column has errors or dynamic changes it can be converted to a non basic column with ForceNonBasic and then handled safely as a non basic column.

4. Pivot-in-Place (PIP)

When a basic column is scanned (e.g., read in) the entries in the column would be a unit column if all arithmetic were always exact; but, because of round-off errors, the column may no longer be an exact unit column And, if it has been edited (e.g., modified dynamically) it may not even be approximately a unit column. VSM uses ForceNonBasic to convert the column to a non basic column. If it still qualifies as a pivot column VSM will select a pivot row. If the errors in the column are small, or if the data in the column has not been changed, VSM might select the same row as the pivot row.

Most algebraic methods for solving linear equations start with a system in the form Ax=B and generate a sequence of equivalent systems $A_1 x=b_1, A_2 x=b_2, \ldots, A_k x=b_k$ until a system is obtained for which the solution is obvious. When these calculations are done by hand using rational arithmetic it is conceptually possible to keep these systems equivalent so that the solution of the last system is also a solution of the initial system. When these calculations are performed on a computer, however, slight round off errors occur so that the systems are no longer exactly equivalent. An extensive literature exists dealing with these errors and many methods are available for minimizing the effects of these errors and estimating their size. We will take a very different approach. The embodiment of the invention we describe here includes a way to transform the calculations on the computer, which are subject to computer error and its accumulation, into a more robust computation that is not subject to the accumulation of computer errors. We will store the initial coefficient matrix A and generate a sequence of factor matrices, $I, E_1, E_2, \ldots, E_k$. In accordance with one embodiment, we will store only the initial A and b column and the current $E_k$. At any time we can use equation (18) to generate the equivalent system or any part of it that we wish. The system (18) need exist only virtually—i.e., it can be computed from stored values of $E_k$, A, and B.

The matrix for the initial system (17) has an embedded identity matrix. Its columns are unit columns, a column of zeros with one entry equal to 1. Each pivot exchange selects a non basic column for a new basic column and replaces a column that was previously basic. After each pivot exchange we again have m+1 unit columns (assuming no computer round-off error). They can be rearranged to constitute an identity matrix. If the same columns of the original matrix are selected and rearranged in the same way they would constitute a sub matrix C for which E would be its inverse. Traditional implementations of the simplex algorithm take b'=Eb as the basic solution under the assumption that EC=I.

When the operations in (18) are carried out on a computer, however, the two linear systems are often not exactly equivalent. That is, they often do not have exactly identical solution sets due to computer round-off errors. But as long as the implied arithmetic operations are not carried out and the matrix E is invertible, the two linear systems have identical solution sets. Round off errors can accumulate in E. But as long as E is invertible we may not have the best possible E; but we do not have errors. The E matrix we do have is entirely suitable in the sense that it defines an exactly equivalent problem with an exactly identical solution as long as E is invertible, and our VSM method is designed to get better and better versions of E, that is, ones that are closer and closer to an actual inverse of A.

The questions are: how do we measure how close the current E is to being correct, that is, to being an inverse of A, and how do we find a better choice for E if we do not have the correct one?

To answer this question we look for a way to measure how far off our choice is. After each pivot exchange we have basic columns equal in number to the number of rows. By rearranging the order of the columns, the matrix contains a unit matrix. By rearranging the columns of the original representation of the linear system, we can identify a submatrix B for which EB=I. If we have a close candidate for the inverse of B this calculation will give us something in the form of $$EB = I + \Delta \quad (19)$$

where $\Delta$ is a matrix with small entries. We use the size of the entries in $\Delta$ as a measure of how good E is as a choice. How can this choice be improved? Calculate $$(I-\Delta)(EB) = I - \Delta^2 \quad (20)$$

If the entries in $\Delta$ are small the entries in $\Delta^2$ are even smaller. That is, $(I-\Delta)E$ is a better choice for an E.

There are several objections to taking this route. The calculation of $EB = I + \Delta$ is a matrix multiplication that requires approximately $m^3$ arithmetic multiplications. Then the calculation of $(I-\Delta)E$ requires $m^3$ more. This compares unfavorably with the $m^3/3$ multiplications required to do Gaussian elimination. Also, the process requires that we compute both EB and $(I-\Delta)E$. That is, even if a small improvement is desired, once started the whole process must be completed. Furthermore, for computer calculations matrix multiplications are not associative and the accuracy of $I-\Delta^2$ is achievable as $(I-\Delta)(EB)$ but not as $((I-\Delta)E)B$. These operations do not fit comfortably into the embodiment we propose. Fortunately, there are satisfactory answers to these concerns.

There is a better way. Let $\Delta_k$ be an m×m matrix with all zeros except that column k of $\Delta_k$ is column k of $\Delta$. Then $$\sum_{k=1}^{m} \Delta_k = \Delta \quad (21)$$

and $$\prod_{k=1}^{m} (I - \Delta_k) \approx I - \Delta \quad (22)$$

If we compute the product $(I-\Delta_k)E$ we obtain the new column j of E, $$c_{kj}^1 = (1-\delta_{kk}) e_{kj} \quad (23)$$

and $$c_{ij}^1 = e_{ij} - \delta_{ik} e_{kj}, i \neq k \quad (24)$$

Now let us compute column j of E after a Pivot-in-Place. The pivot column is identical to column k of $I+\Delta_k$. That is, $p_k = 1+\delta_{kk}$ and $p_i = \delta_{ik}$ for $i \neq k$. When we do a Pivot-in-Place the new column j is $$e''_{kj} = e_{kj}/(1+\delta_{kk}) \approx e_{kj}(1-\delta_{kk}) = c'_{kj} \quad (25)$$

$$e''_{ij} = e_{ij} - \delta_{ik} e_{kj}/(1+\delta_{kk}) \approx e_{ij} - \delta_{ik} e_{kj}(1-\delta_{kk}) = c'_{ij} - e_{kj} \delta_{kj} \delta_{ik} \delta_{kk}, i \neq k \quad (26)$$

This shows that multiplication by $(I-\Delta_k)$ and doing a Pivot-in-Place produce approximately the same results.

We can make an estimate for the error in the solution. If $\bar{E}$ is the exact inverse of A and $\bar{b}=\bar{E}b$, then $A\bar{b}=b$ and $\bar{b}$ is an exact solution. If E' is an approximate inverse and b'=E'b then $$b'-\bar{b}=E'b-\bar{E}b=(E'-\bar{E})b=(E'-\bar{E})A\bar{b}=\Delta\bar{b} \qquad (27)$$

This gives a theoretical bound for the accuracy of the solution. The usefulness of this estimate is limited by the precision with which the $\Delta$ is computed

III. Computer Implementation of the Virtual Simplex Method

The purpose of this section is to describe an embodiment of the Virtual Simplex Method such as could be implemented by a computer operating a software program. One example is available in U.S. provisional patent application No. 61/662,608, filed on Jun. 21, 2012 and titled "Methods and Apparatus Relating to Advances in Virtual Simplex Method" which is hereby incorporated by reference in its entirety and for all purposes.

A. Initialization

When VSM imports a problem it should store the data in a configuration that VSM expects. VSM introduces a slack variable for each constraint so that the problem is in the form Ax+y=B where the slack variable is artificial if its associated constraint that is an equality and it is canonical if its associated constraint is a less-than-or-equal inequality. If there are in constraints the rows of A are indexed from 1 through m. The objective function, or f-function, is adjoined as a row indexed 0. For simplicity, we continue to use the same notation, that is, the relation Ax+y=B has m+1 rows indexed from 0 through m. The slack variable for the objective row is the free objective variable.

The coefficient matrix A is stored as a list of columns with the first column following the last column. The A matrix has no pre-determined limit to the number of columns that it may contain. With each column is stored the decision variable name associated with the column. The right hand side (RHS), or B column, is stored in a cache memory. These data will remain static throughout a run unless they are edited.

B. The Virtual Problem (or h-Problem)

VSM can create a virtual problem by creating a matrix, the E matrix, with m+2 rows and m+1 columns. The columns are indexed from 0 through m and the rows are indexed from −1 through m. Initially, this matrix is all zeros except for 1's in the entries with equal row and column indices. That is, row −1 is a row of zeros and the other rows form an identity matrix. The virtual problem is implied by the relation EAx+Ey=EB. The column EB is stored with the E matrix as an added column so that it will be subject to the same computations as will the rest of the E matrix. We denote this column by b (lower case). Special computer hardware, described later, can be used to store the entries in the E matrix. This special device is called the Ematrix (without a space) or E matrix storage device. Its embodiment is designed to optimize its role in the VSM. Few entries in the implied EA matrix are computed: only those that are needed to provide information used by VSM to make decisions.

C. Basic Feasible Form

The variables given in the original data are called decision variables. During a run VSM introduces other variables called slack variables and virtual variables. VSM initializes the problem to be represented in basic feasible form. The representation is in basic feasible form if in the E matrix and b column:

1. Each constraint row is associated with a variable, which is called a basic variable. Initially, the slack variables are basic and each slack variable is associated with the row and column with its index.
2. Initially, the columns associated with basic slack variables and basic virtual variables are unit columns. All entries in the columns are zeros except for a 1 in the row with which it is associated. Initially, the columns of basic slack variables and basic virtual variables are exact unit columns VSM attempts to make the columns associated with basic decision variables as close to being unit columns as computer error allows.
3. The entries in the b column associated with canonical basic variables are non negative.
4. There are no basic artificial variables.

A basic column in the implied EA matrix will be computed and its entries will often only approximate these values. The deviation from the ideal values are the deltas that are measures of the accuracy of the representation. At this point in the initialization VSM has taken steps to ensure that conditions 1 and 2 are satisfied.

D. Basic Solutions

A basic solution is the solution obtained by setting all non basic variables in the system of equations equal to zero and solving for the basic variables. In most implementations of a simplex-like method the b column is identified with the basic solution. But the b column is not the basic solution in the sense defined here. If there are computer errors it is not even a solution. It is the right hand side (RHS) of a system of equations. If the columns associated with basic variables are nearly unit columns the RHS is nearly a basic solution. Throughout a run the ideal values of basic columns in the E matrix and the basic columns of virtual variables, the variables introduced by VSM, will, in fact, be zeros and ones. A basic column associated with decision variables will be computed and its entries will only approximate these values. The deviation from the ideal values are the deltas that are measures of the accuracy of the representation.

E. ForceFeasible

VSM examines the entries in the b column to determine if there are any negative entries. If there are negative entries in the b column, VSM initiates a ForceFeasible operation. VSM creates a new canonical virtual variable and creates a column for it in the E matrix. VSM creates a pivot column consisting of all zeros with the following exceptions. In a row with a negative entry in the b column the entry for that row in the pivot column is −1. In the virtual row (sometimes referred to as the h-function row) the entry is 1. VSM then selects the row with the most negative entry as the pivot row. A pivot exchange is performed. When this is completed the problem satisfies condition 3. The pivot row is now associated with a new basic virtual variable. After this step the requirement 3 for basic feasible form is satisfied.

F. ForceNonBasic

VSM examines the variables associated with the rows to determine if any are artificial. If there are artificial variables, VSM initiates a ForceNonBasic operation for each artificial variable. The entries in the row of the artificial variable are subtracted from the h-row. This has the same effect as would be obtained by performing a pivot exchange in a column of zeros except for a 1 in the row, the pivot row, of the artificial variable and a 1 in the h-row. The artificial variable becomes (is forced) non basic and a new basic virtual variable is introduced. When this step is performed for every artificial variable and all four conditions noted above have been satisfied, the problem is in basic feasible form.

ForceFeasible and ForceNonBasic resemble operations used in versions of the simplex algorithm to create an auxiliary problem for phase one of a two-phase simplex method. In two phase versions of the simplex algorithm these operations appear only in phase I and only initially. In VSM, however, these operations may be used throughout a run and the virtual problem exists throughout a run. These operations play a new and different role. They serve to make a run stable and robust and allow VSM to handle dynamic problems whose data can be changed during a run.

The 1 in the virtual row (or h-function row) means that the h-function is the sum of the virtual variables. This means that the virtual function (or h-function) is always non negative. VSM treats the virtual problem as a minimization problem. Since the virtual problem is a linear program and the h-function is bounded below by zero, the h-function always has an optimal solution.

When initialization is complete the virtual problem is in basic feasible form. VSM maintains basic feasible form throughout a run. VSM monitors the number of basic virtual variables and whenever the count becomes zero VSM writes zeros in the virtual row of the E matrix. Thus, errors in computing this row are not persistent and they play no role in a basic solution of the optimality problem.

G. Pivot Selection Rules

1. Column Selection Rules

In accordance with one embodiment, before termination VSM must examine all columns of the E matrix. The information needed to select or reject a column of the E matrix as a candidate for selection as a pivot column is contained in the rows of the column under consideration for the rows containing the h-function and the f-function. Additional information utilized in the selection/rejection process is the information as to whether the variable is free, artificial or basic, and whether the problem is a minimization or maximization problem. We refer to these numbers from the h-function row and the f-function row as the column selectors. The column selectors associated with the columns of the E matrix are calculated and available after each pivot exchange. For that reason the columns of the E matrix are scanned after each pivot exchange. The −1 index (virtual) row in the E matrix is the computed portion of the coefficients of the h-problem and the 0 index (objective) row in the E matrix is the computed portion of the coefficients of the f problem.

The rules for selecting a column of the E matrix in accordance with one embodiment are the following.

1. If the variable associated with a column is artificial or basic the column is skipped.
2. If the entry in the virtual row is positive the column is skipped.
3. If the entry in the virtual row is negative the column is selected as a pivot column
4. If the entry in the virtual row is zero the decision is passed to the entry in the objective row. If the optimality problem is a minimization problem and the entry in the objective row is positive or zero the column is skipped. If the optimality problem is a maximization problem and the entry in the objective row is negative or zero the column is skipped.
5. If the optimality problem is a minimization problem and the entry in the objective row is negative the column is selected. If the optimality problem is a maximization problem and the entry in the objective row is positive the column is selected.

After a column is selected as a pivot candidate, a pivot exchange is performed. Immediately after each pivot exchange VSM looks for an eligible pivot column in E. This priority pivot column selection process is based on the fact that the numbers needed to select a pivot column in E are computed in the computation involved in performing the pivot exchange and no additional computing is required. Thus, VSM repeatedly looks for a pivot column in E until after scanning all of the columns it is unable to find another pivot column. This may require multiple scans of E.

VSM then turns its attention to finding an eligible pivot column in EA. However, nothing in EA has yet been computed. VSM needs the entries in the virtual and objective rows, the columns selectors for EA. These numbers are in a matrix that is the product of the matrix S formed by the computed and available portions of these rows in the E matrix and A. It is desirable to compute these simultaneously in parallel. VSM assembles as large a sub matrix $\overline{A}$ of A for which there are enough processors available to compute the entries in $S\overline{A}$ as can be computed in parallel.

The following are the rules for selecting a pivot column in EA in accordance with one embodiment.

1. If the PIP operation is enabled and the variable associated with the $EA_k$ column is basic a Conductor processor performs a ForceNonBasic operation. The rationale for this rule will be discussed later. It has the effect that every column in the EA matrix is treated as a non basic column, to which the following rules apply.
2. If the variable associated with the $EA_k$ column is free the column is selected as a pivot column.
3. If the entry in the virtual row is positive the $EA_k$ column is skipped.
4. If the entry in the virtual row is negative the $EA_k$ column is selected as a pivot column
5. If the entry in the virtual row is zero the decision is passed to the entry in the objective row. If the optimality problem is a minimization problem and the entry in the objective row is positive or zero the $EA_k$ column is skipped. If the optimality problem is a maximization problem and the entry in the objective row is negative or zero the $EA_k$ column is skipped.
6. If the optimality problem is a minimization problem and the entry in the objective row is negative the $EA_k$ column is selected. If the optimality problem is a maximization problem and the entry in the objective row is positive the $EA_k$ column is selected.

2. Row Selection Rules

When a column $A_i$ is selected VSM computes the pivot column, $p=EA_i$. Then for each positive entry $p_j$ in the pivot column VSM computes the ratio $r_j=b_j/p_j$. For non positive entries in the pivot column VSM sets $r_j=-1$. For rows associated with free variables VSM overwrites the ratios with −1. The following rules are used to select the pivot row in accordance with one embodiment.

1. VSM selects a row for which the ratio is least non negative. The effect of writing −1's into the ratio column is to make rows with non positive entries in the pivot column and rows associated with free variables ineligible for selection.
2. If there is a tie, VSM gives priority to a row associated with a virtual variable.
3. If there is still a tie. VSM gives priority to the row with the smallest index.

Though the virtual problem is a minimization problem the goal is not to force it to zero. The goal is to make all virtual variables non basic. When there are no basic virtual variables all basic variables are variables of the optimality problem and the basic solution of the virtual problem is also a basic solution of the optimality problem. Rule 2 means that if a virtual variable is associated with an eligible row, a row with the least non negative value for the ratio, a row of a virtual variable will be selected.

3. Termination

In accordance with one embodiment, the user must initially assign a value to a parameter, Epsilon, that the user accepts as essentially zero. In selecting a pivot column VSM interprets >0 as >Epsilon and ≥0 as >−Epsilon. When working a minimization problem VSM terminates when it cannot find a column with a negative selector. That is, all selectors are >−Epsilon. For each non basic variable its selector in the objective row is the value of its dual basic variable. Thus, the basic solution for the dual problem is also feasible. This is a sufficient condition for optimality for both-problems.

If there are basic virtual variables at termination the optimization problem is infeasible.

H. Bookkeeping

In addition to the data available in the E matrix VSM needs other information to keep track of its progress in a run, in accordance with one embodiment. When a column is imported the name of the variable associated with the column is saved in association with the column Flags to determine whether the variable is free or canonical and whether it is basic or non basic are provided. If the variable is basic, then the index of the row associated with the basic variable is also saved. One can save the information either with a flag or with a list.

Upon import, an array of slack variables, each associated with a column of the E matrix, is created. In addition to the variable name each element of the array contains flags to determine whether the variable is artificial or canonical and whether the variable is basic or non basic.

VSM creates an array of basic variables, each associated with rows indexed from 1 through m. Each element of the array contains the name of the basic variable associated with the row. It contains a flag to determine whether the variable is free or canonical. It also contains information as to whether the variable is a variable in the A matrix, the E matrix, or is virtual. If the variable is in the E matrix, the element also contains the index of the column in the E matrix. If the variable is in the A matrix, the element also contains a pointer to the column in the A matrix.

The information in these arrays must be updated with each pivot exchange. The flag values are used in the rules to select a pivot column or a pivot row. If a column in the EA matrix is selected and ForceNonBasic is enabled, VSM uses the index of the associated basic row when it executes a ForceNonBasic. When a pivot row is selected VSM must do the following. If the variable associated with the row is a variable in the E matrix VSM must use the index of the column to set the basic flag for that column false. If the variable associated with the row is a variable in the A matrix VSM must use the pointer to the column to set the basic flag for that column false. The variable name of the pivot column becomes the variable associated with the row. If the pivot column is in the E matrix, the index of the column and the fact that that column is in the E matrix is written into the element of the basic array. If the pivot column is in the E matrix, the pointer to the pivot column and the fact that that column is in the A matrix is written into the element. If the variable associated with the pivot column is free, that flag must be set.

I. VSM is a Single Phase Method

1. Scanning and Pivoting, Termination

One approach to minimizing the time it takes for a simplex-like algorithm to reach an optimal solution is to minimize the number of steps it takes to reach optimality. Another is to perform the operations that are required more quickly. The second approach will be discussed in the section on the EMatrix.

Strategies to reduce the number of steps include strategies to reduce the number of pivot exchanges and to reduce the number of columns that have to be scanned. VSM reduces the amount of data that has to be scanned. VSM works on the virtual problem and the optimality problem at the same time.

In accordance with one embodiment, to determine that VSM has reached an optimal solution it is necessary to establish that all columns have been scanned without finding a column eligible for a new pivot exchange. By scanning the columns in sequential order this is easy to determine Every time VSM performs a pivot exchange on a column in the A matrix it sets a pointer to that column. This column is now the column of a basic variable. Whenever VSM scans a basic column it checks to see if the column being scanned is the column involved in the last previous pivot exchange. If it is, the run terminates. If there are no basic virtual variables at termination, the basic solution is also a solution of the optimality problem and an optimal solution has been attained.

There is the logical possibility that the run terminates for other reasons. If VSM completes a circuit without finding a new pivot column and there remains a basic virtual variable the problem is infeasible. If the constraints describe a business enterprise that would mean the enterprise cannot conduct its business at all. In that event it is likely that the constraints are improperly formulated. If there are no basic virtual variables and VSM finds an eligible pivot column and fails to find an eligible pivot row, the objective function is unbounded. If the objective function is the profit that the enterprise can make it is unlikely that it can make an infinite profit. Again, it is likely that the constraints are improperly formulated.

It is possible to ascribe significance to these possibilities in many situations. For example, if the constraints describe how an airline should schedule its resources to minimize its costs, infeasibility would mean that the proposed schedule cannot be met with the resources available.

One set of pivot selection rules is used from initialization through termination. VSM is a single phase method. VSM never has to be restarted. Rather, it can simply input new data and implement the operation of its rules.

2. Cycling

Cycling, endlessly repeating a sequence of pivot exchanges, is mostly a theoretical problem for simplex-like algorithms. There are examples of problems that cycle, but these are contrived examples that cycle because of their exploitation of a particular set of selection rules. The existence of the Bland anti cycling rule shows that there are no problems that intrinsically cycle. VSM provides no built-in method for preventing cycling because we have not been able to produce an example that cycles under VSM.

If an example is produced that cycles under VSM there are several readily available methods for breaking a cycle. Cycling occurs when there are ties for selecting a pivot row. If there is never a tie for selecting the pivot row the run will not cycle. A tie will produce at least one zero in the b column of the subsequent representation of the problem. These zeros will produce more ties and methods used to prevent cycling rely on methods for breaking ties.

If zeros appear in the b column, the editing capability of VSM can be used to produce a slightly different B column that will produce a b column with no zeros. If these changes are small, the run will produce basic solutions that approximate the desired basic solutions. At an appropriate point the original B column can be restored and the run will continue with the ties broken.

It is also possible to break a cycle by using an operation like ForceFeasible and ForceNonBasic to perturb the entries in the b column so that ties would not occur. This method has the advantage that the first time that a bUpdate occurs these perturbations would disappear.

3. Termination Mode

Complications can arise in some instances from determining termination. Currently, one can enable or disable ForceNonBasic (FNB). To determine termination, VSM in accordance with one embodiment determines when all columns have been scanned without finding a pivot column (or a pivot row, but that is not the issue here). This requires two pointers, one to the column where the last pivot exchange was performed and one to the last column where FNB was performed. If only a last pivot pointer (LPP) were maintained scanning would start there repeatedly and VSM would always find the same basic column for its FNB. If only a last action pointer (LAP) were maintained VSM would run forever.

In accordance with one embodiment, there is a different dichotomy: Termination Mode vs. Endless Mode. Endless Mode would be simple because there would be no need to determine when a circuit had been completed without finding a pivot column FNB would be enabled by default in Endless Mode. FNB would be disabled by default in Termination Mode.

It has already been mentioned that one could leave FNB disabled until optimality is reached and think of PIP as playing a role similar to re-inversion. Termination Mode would be configured to work that way. That is, FNB would be enabled after termination was reached.

This results in a simplification. With FNB disabled VSM needs only an LPP. It uses the E selectors (ES) to look for a pivot column in the E matrix and it uses the A selectors (AS={ES} A) to look for a pivot column in the EA matrix. LPP is not moved by a pivot exchange in the E matrix. When it cannot find a pivot column in the E matrix VSM uses the AS to look for a pivot column in the EA matrix. If it finds one it does the pivot exchange and resets LPP. It can determine when it does not find a new pivot column when it has scanned the entire AS without finding one. As long as VSM runs with FNB disabled it does not need to maintain an LAP.

At this point VSM knows that it has reached termination. It then enables FNB for the final circuit. At first it sounds as though VSM faces the same problem it does now. The simplification comes from the fact that VSM knows where termination comes before it enables FNB. It does not have to keep testing for termination. It uses the LAP only to determine where to start scanning but LAP need not play a role in termination.

When FNB is enabled VSM can perform FNB at each basic column. If the basic variable is restored the operation is a PIP and it does not count as a pivot exchange. If the operation results in a new basic variable the operation is counted as a pivot exchange. In that case LPP is reset, FNB is disabled and the run continues.

Editing would take place during a pause or at termination. Editing would automatically enable FNB until a pivot exchange takes place or until a circuit is completed.

J. Computational Accuracy

VSM looks at computational accuracy differently and handles it differently from versions of the simplex algorithm. Computer errors cause difficulty in finding an accurate solution primarily in two ways. Errors can make the computed representation of the problem inequivalent to the original problem. Errors can make the computed E matrix far from being the inverse of a sub matrix of the original A matrix. VSM can address the first difficulty by periodically restoring the equivalence of the representation and the original problem. VSM can address the second difficulty by its Pivot-in-Place operation 1. Force Feasible, bUpdate After a problem is imported, E and b undergo the same sequence of pivot operations. Because of computer error the current representation of the problem, EAx=b, will soon fail to be equivalent to the initial problem. Since B is saved and remains static it can be used to restore equivalence by replacing b by EB. When that action is taken the problem is represented in the form EAx=EB. We refer to this operation as bUpdate. The only requirement for equivalence is that E be invertible. Even with large computer error the probability that E will not be invertible is almost zero. Regardless of the errors that have occurred in computing E the only errors that appear in the representation EAx=EB are those that occur in computing EA and EB. Versions of the simplex algorithm could restore equivalence in the same way, but they would do so at the risk that EB might contain a negative entry. This would mean that the run has gone infeasible and the run would fail. There is no restriction as to when in a run a bUpdate can be performed. One embodiment performs a bUpdate once in a circuit.

VSM has available the operation ForceFeasible. VSM can update the b column at any time by writing EB over b. Whenever it takes this step VSM inspects the new b column and, if there are any negative entries, it performs a ForceFeasible. An update to the b column might be required due to a change in constraint(s).

2. ForceNonBasic, Pivot-in-Place

The columns associated with basic variables in the E matrix are always initially exact unit columns Columns associated with basic variables in the A matrix should be unit columns but computer errors in computing E and in computing EA make this unlikely. E should be the inverse of the matrix C made up of the columns of 4 associated with basic variables. That is, EC=I−Δ where the entries in Δ measure the deviation of E from being an exact inverse of C. Since the basic solution is the solution of the constraints Ax=B when the non basic variables are assigned zeros, the basic solution obtained from the current representation of the problem is the solution of ECx=EB. That is, if $\bar{b}$ is the basic solution then EC $\bar{b}$=(I+Δ)$\bar{b}$=EB, or $\bar{b}$−EB=Δ$\bar{b}$. If Δ is small then EB is a good approximation of the basic solution b.

Other simplex-like methods refer to b as the basic solution. It is not a solution, it is the RHS of a system of equations for which the solution is, if the system of equations is equivalent to the original system, the basic solution. VSM takes a two-track approach to computer accuracy. It periodically updates the b column by invoking bUpdate. This assures that the current representation of the constraints is equivalent to the original system. Then it uses Pivot-in-Place (PIP) to make Δ small so that the b column is a good approximation of the basic solution.

The rationale behind PIP is this. If $A_i$ is a column associated with a basic variable then $EA_i$ is a column of I+Δ. If this column, $EA_i$, is converted to a non basic column by ForceNonBasic, it can be handled by VSM the way VSM handles any other non basic column. If the column is eligible for selection as a pivot column VSM will perform a pivot exchange and try to make the column a basic column. It will try to make the entries in that column a unit column.

The PIP operation will not necessarily make the column an exact unit column. It will make it as close to being a unit column as the set of basic columns will allow. Most importantly, computer errors that have occurred previously in the run will be irrelevant. There will be no accumulated error. The computer error that occurs is the computer error of this particular pivot exchange only.

If PIP is enabled and a circuit is completed without finding a new pivot column, PIP will have been performed on every basic column. This is equivalent to re-inversion in the revised simplex algorithm and it will do as well as a re-inversion in reducing the size of the entries in $\Delta$.

Pivot-in-Place has the advantage over reinverting in that it employs the same arithmetic steps as those employed in a pivot exchange. It can be enabled or disabled at any time during a run. One possible option is to run to optimization with PIP disabled and then enable PIP for a last circuit. Another possible option is the run to optimization with low precision arithmetic, which will take less time than would be required with high precision, and then enable PIP for the last circuit.

K. Edited Data and Dynamic Problems

VSM was designed to run continuously while monitoring an enterprise described by the constraints. One example would be an electric power grid in which the demand fluctuates with time. Another would be a financial portfolio in which the values of the stocks change periodically. It could be any enterprise in which a resource changes either unexpectedly or by plan. To simplify the discussion we consider how a single editing change is handled.

1. Edited b Column, bupdate, ForceFeasible

When the problem is imported the RHS, the B column, is saved and is retained to be available to refresh the computed b column. When first imported the given problem is in the form Ax=B. In the course of a run the representation has the form EAx=b where the pivot operations that are applied to E are also applied to b. If the column stored in B is changed (edited), VSM is unaware of the change and it continues to work on the data associated with the data describing the problem before the change. VSM is configured to perform a bUpdate periodically. It replaces b by EB so that the new presentation is EAx=EB. When the update occurs, the representation will be equivalent to the new problem. If the change is small the entries in the new b column are likely to be still non negative and the run can continue without difficulty. If the change produces a negative entry in the new b column, VSM will perform a ForceFeasible. This will restore basic feasible form at the expense of introducing a new basic virtual variable.

VSM will proceed normally and try to make the virtual variable non basic. If it does not succeed the change was so great that the new problem is infeasible. If it does succeed the new problem is feasible and VSM will proceed to find a new optimal solution.

2. Edited A Column, ForceNonBasic, Pivot-in-Place

If a column is non basic at the time it is edited there is no need for VSM to do anything immediately. When the column is scanned it will be treated as any other non basic column would be treated.

If the column is basic, VSM performs a ForceNonBasic. When this action is taken the column becomes a non basic column. If the change is small it is likely that the row associated with the new basic virtual variable will be selected as the pivot row. In that case the old basic variable is basic again and the virtual basic variable becomes non basic and can be dropped. However, if the change is large the selection rules may not select the column again or they may not select the same row. In that case the new virtual variable will remain basic and VSM will try to make it non basic. If it does not succeed the change was so large that it produced an infeasible problem. If it succeeds the new problem is feasible and VSM will find a new optimal solution.

When VSM encounters data that it does not expect, it does not know when the anomaly is the result of computer error or the result of editing. VSM handles both cases in the same way.

VSM can optionally stop when an optimal solution is reached, or it can continue indefinitely. When changes in the problem data occur (i.e., changes to A or B) these changes will be picked up and a new optimal solution will be produced, or the change will cause the problem to become infeasible. Even in the infeasible case the virtual problem is in basic feasible form and the run can continue. If subsequent changes produce a problem that is feasible, VSM will recognize feasibility. The run does not have to be restarted.

Because of VSM's robustness with infeasibility and its ability to avoid accumulation of computer error, VSM can run indefinitely without failing.

3. Inserting or Removing a Variable

A non-basic variable and its associated column can be introduced at any time. It will be non basic and when VSM scans the new column it will be treated as any other non basic column would be treated. A non basic column can be removed at any time. A non basic variable is assigned a zero value in the current basic solution. If it is removed the current basic set will remain basic and the run can continue.

If the variable is basic it can be made non basic with a ForceNonBasic. As soon as it becomes non basic it can be removed. This operation will introduce a basic virtual variable and VSM will attempt to convert it to non basic status. If it cannot convert the basic virtual variable to non basic status the altered problem is infeasible. If it can be removed the run will continue without difficulty.

J. The EMatrix

VSM is designed to concentrate the numerical computation in one part and the decision making in another part. This allows each to be optimized for its task. The part that does the computation is designed to allow extensive parallelization. It relies heavily on special hardware. We refer to this implementation as the Ematrix. This unit will be described first.

The most frequently occurring computation that is performed in a simplex-like algorithm is the pivot exchange. Though it is not the only operation performed in the Ematrix it will serve to define its features.

If $E=[e_{ij}]$ is the E matrix and $p=[p_i]$ is the pivot column and $p_r$ is the pivot entry selected in the pivot column, VSM first updates the pivot row by computing $e'_{rj}=e_{rj}/p_r$. These computations can be performed in any order and even simultaneously. After the pivot row is updated the entries in E that are not in the pivot row are updated by computing $e'_{ij}=e_{ij}-p_i*e'_{rj}$. These computations can also be performed in any order and even simultaneously. This observation invites parallelization.

The Ematrix is structured as a collection of objects, in the sense used in object oriented programming Each object is associated with one row of the E matrix. Each object, referred to as an ERow, has the following fields.
ID:integer;
Row:array of real;
bbb:real;
ppp:real;
rrr:real:

The ID field is an index that associates the object with a row of the E matrix. The Row field contains the entries in the row of the E matrix associated with this object. The bbb field is the RHS term in the constraint represented by this ERow. For computational efficiency this term is stored as the $e_{-1}$ entry of the Row field. The ppp field is the entry in the pivot column associated with the row, and the rrr field is a ratio associated with the row.

There is just one procedure associated with each ERow. It is listed in full below.

```
procedure TERow.Action;
var
    i : integer;
begin
    case ECache.MethodID of
        1: begin // InitializeE
            for i := 0 to MaxRow do
                Row[i] := 0;
            if ID >= 0 then
                Row[ID] := 1;
        end;
        2: begin // GetPivotColumn
            ppp := ECache.EColumn[ID];
        end;
        3: begin // GetPivotColumnInE
            ppp := Row[ECache.PivColumnInE];
            if (ppp > ECache.Epsilon) and (ID > 0) then
                rrr := Row[-1]/ppp
            else rrr := -1;
            ECache.RColumn[ID] := rrr;
        end;
        4: begin // doBUpdate
            Row [-1] := 0; // Row[-1] is the bbb field.
            for i := 0 to MaxRow do
                Row[-1] := Row [-1] + ECache.BColumn[i]*Row[i];
        end;
        5: begin // Computeppp
            ppp := 0;
            for i := 0 to MaxRow do
                ppp := ppp + ECache.AColumn[i]*Row[i];
            if (ppp > ECache.Epsilon) and (ID > 0) then
                rrr := Row[-1]/ppp // rrr := bbb.ppp
            else rrr := -1;
            ECache.RColumn[ID] := rrr;
        end;
        6: begin // NewPivotRow;
            with ECache do
                if ID = RowID then
                begin
                    for i := -1 to MaxRow do
                        Row[i] := Row[i]/ppp;
                    PRow := Row;
                end;
        end;
        7: begin // NewOtherRow;
            with ECache do
                if ID <>RowID then
                    for i := -1 to MaxRow do
                    begin
                        Row[i] := Row[i] - ppp*ECache. PRow [i];
                        if isZero(Row[i], Epsilon)
                            then Row[i] := 0;
                    end;
                if ID = -1 then ECache.VirtualRow := Row;
                if ID = 0 then ECache.ObjectiveRow := Row;
        end;
        8: begin // ComputeNegativerrr
            if (ppp < 0) and (ID > 0) then rrr := -Row[-1]/ppp
                else rrr := -1;
            ECache.RColumn[ID] := rrr;
        end;
        9: begin // Put BColumn
            ECache.EColumn[ID] := Row[-1];
        end;
        10: begin // SubtractFromVirtualRow
            if ID = -1 then
            begin
                for i := -1 to MaxRow do
                    Row[i] := Row[i] - ECache. PRow [i];
                ECache.VirtualRow := Row;
```
```
            end;
        end;
        11: begin // PutPositiveERow
            with ECache do
                if ID = ECache.RowID then
                begin
                    if Row[-1] < 0 then
                        for i := -1 to MaxRow do
                            Row[i] := -Row[i];
                    ERow := Row;
                end;
        end;
        12: begin // NullVirtualRow
            if ID = -1 then
                for i := -1 to MaxRow do
                    Row[i] := 0;
            end;
        end;
    end;
```

The following example illustrates how VSM can be implemented.

Figure 7A:
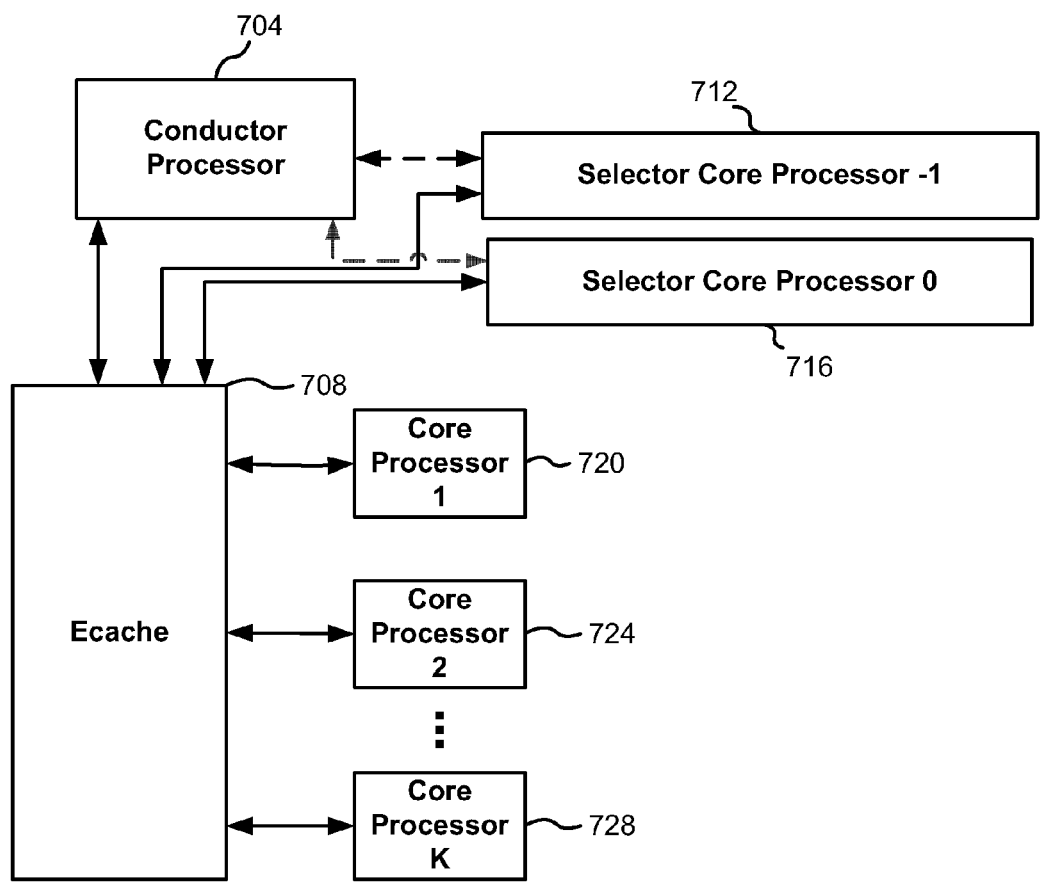
FIG. 7A illustrates a computer comprised of multiple processors for processing a linear programming problem, in accordance with one embodiment of the invention.
Figure 7B:
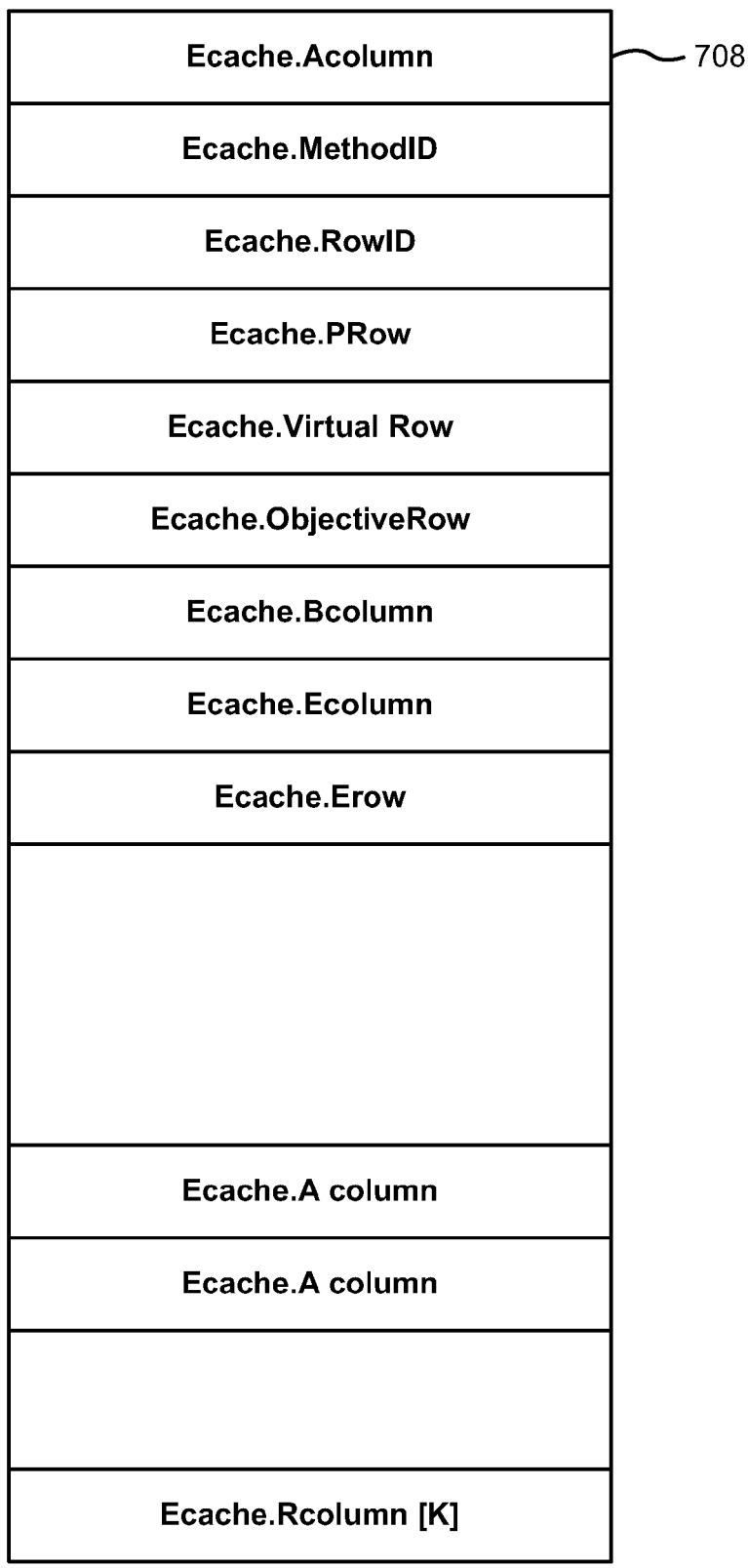
FIG. 7B illustrates a cache memory illustrating storage space for a variety of variables used to process a linear programming problem, in accordance with one embodiment of the invention.
Figure 7C:
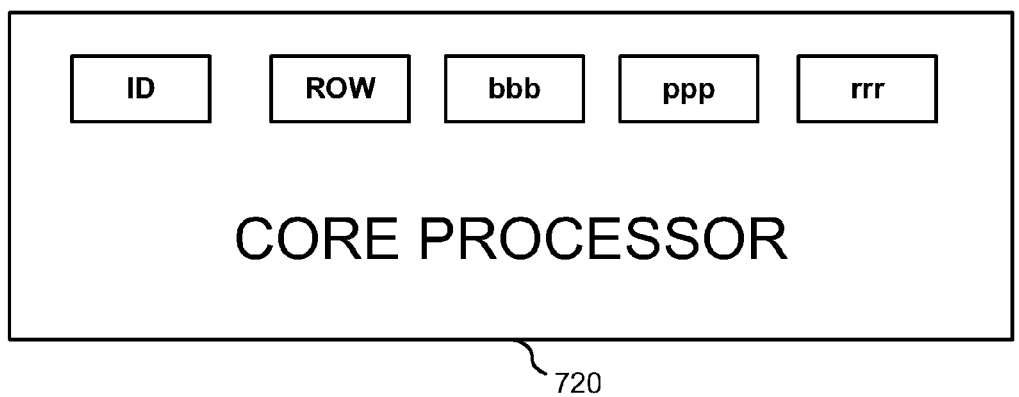
FIG. 7C illustrates an example of register assignments that can be used in the implementation of the core processors shown in FIG. 7A, in accordance with one embodiment of the invention.

The VSM can utilize special purpose hardware in accordance with one embodiment—a computing configuration we call the Autonomous Synchronous Computer (ASC). One example of an autonomous synchronous computer is shown by FIGS. 7A, 7B, and 7C. In the embodiment shown in FIGS. 7A, 7B, and 7C a multi-core processor arrangement is illustrated where a single integrated circuit can comprise multiple processors. Of course, separate integrated circuits could be used for each processor in alternative embodiments.

The computer shown in FIG. 7A is designed to have processors that we sometimes refer to as ERows with self-indexed registers that do not need to be addressed and do not need any RAM. The ERow processors are shown in FIG. 7A as Selector Core processors 712 and 716 and Core Processors 720, 724, and 728. The ellipsis between Core Processors 724 and 728 illustrate that additional core processors could be included as well. FIG. 7C illustrates an example of one such core processor that has individual registers assigned to store values described below.

These processors are autonomous in the sense that they contain their own instructions and their own data. The ERow processors are synchronous in the sense that they operate at the same time, one method at a time, and typically the same method for all.

In the embodiment shown in FIG. 7A, Selector Processors take the place of regular core processors for the rows in the problem that correspond to the objective function f and the halo objective function h. All of the ERows and Selector Processors may communicate with the outside world by reading from and writing to a small amount of commonly available memory which we call a Cache memory. The Selector Processors are shown as being different from the regular core processors (720, 724, and 728) in that they can be in direct communication with the Conductor processor 704 (as illustrated by the dashed lines indicating communication lines for address, data, and control signals).

The controlling program, which we call the Conductor program, is implemented on a processor, which we call the Conductor processor 704, and passes the constraint coefficients to the registers of the E-Processors (and Selector Processors when utilized) until each processor contains constraint values for an entire row. The Conductor processor receives in return just enough information to apply VSM's selection rules for pivot exchanges.

Although one embodiment of the ASC may comprise many processors computing simultaneously, it is not required to be a traditional parallel computer. A metaphor for a parallel computer is to think of a sales office in which the manager gives the salesmen instructions for the day, after which they go about their business independently of each other and report back to the manager at the end of the day. By contrast, a metaphor that is appropriate for the ASC is that of a symphony orchestra in which each player has his own music and the musicians play synchronously under the direction of the conductor. Each component carries out certain tasks on timing cues that it gets from the Conductor processor. In one embodiment of the ASC, the data of the E matrix is contained in a series of processors having indexed registers. Each register is responsible for one row of the matrix. At each timing beat every register is simultaneously updated for the row it is responsible for; this is sometimes called data parallelism (as opposed to task parallelism) in the literature of parallel processing.

In such an embodiment, at no time does any Erow processor need to know what is in any of the registers of the other processors. The Erow processors are, in this sense, autonomous. The ASC may comprise an array of processors which have a very small instruction set and operate entirely out of registers associated with the processors. The processors need not be considered computers; they need not be addressable; and, they need not have any memory beyond the registers. The outside world need not know where the processors are located. The processors can run on their own, even seeking out on their own the information about which of their limited number of instructions they should carry out at any given time. An important factor to the processors' autonomy in this embodiment is that they may be self indexed; they do not have to be addressed. The Conductor processor does not have to know where the processors are. Each processor has an ID field that it uses to identity itself. The Conductor processor may put information into a cache and each processor compares its ID with a RowID in the cache to determine what actions it should take.

The Conductor processor and the Erows processors do not need to communicate directly with one another. They can use a small shared computer memory area that can be referred to as the ECache. This is shown as computer memory 708 in FIG. 7A. FIG. 7B shows various data described below that can be stored in the cache memory 708. The Ecache memory functions like a drop box used by espionage agents. When VSM has selected a column of the A matrix for use in a pivot operation it writes the contents of that column to ECache.AColumn. It then writes Computeppp=5 to ECache.MethodID and triggers the ERows to action. The trigger can be as rudimentary as an electronic pulse. The ERows run their shared procedure, a case statement, and execute Computeppp. They each compute their ppp field. They then compute rrr=bbb/ppp if ppp>0, else they set rrr=−1. Each Erow copies its rrr field to ECache.RColumn[ID]. VSM uses these ratios to select a pivot row.

VSM writes the index of the selected row to ECache.RowID, NewPivotRow=6 into ECache.MethodID and triggers the ERows. When the Erows perform their procedure the selected ERow updates the data in its Row field. It replaces $e_j$ with $e'_j/ppp$. It then writes its Row field to ECache.PRow.

With the pivot row index still in ECache.RowID VSM writes NewOtherRow=7 into ECache.MethodID and triggers the ERows. Every ERow except the selected pivot row updates its Row field. It replaces $e_j$ with $e'_j=e_j-ppp*ECache.PRow[j]$. Finally, the ERow processor with index −1 writes its Row field to ECache.VirtualRow and the ERow with index 0 writes is Row field to ECache.ObjectiveRow. These two fields are used by VSM to select the next pivot column.

Though the code listed above was used to implement the EMatrix, the code is merely a suggestion. There are many ways to implement the EMatrix. The EMatrix need only be able to respond to the trigger, read and write to the ECache, and implement the twelve methods described.

Note that the ERows do not need to read from or write to one another. They are structurally parallel. They use no RAM. The memory they use is either their own fields or the ECache. They are simple enough that they could be implemented in hardware on a chip or circuit board. They would take very little space and many could be implemented to function in parallel.

Though the code above suggests that an ERow writes to ECache.EColumn[ID], in fact the ERow is not aware that the memory location is part of an array. It owns the location and no other ERow is aware of it. The connection can be hard wired. Also, when an ERow writes to ECache.PRow in shared memory, the location is shared only with the other ERows. The ECache.Prow could be on a bus that is invisible to VSM.

The decision making part of VSM can be implemented using a widely supported language like C and the ERows can be implemented in a different language on a different platform.

Any available technology, such as taking advantage of the sparseness of the A matrix, can be utilized.

In one embodiment, a Conductor processor does the decision making. The Conductor processor need not address or see any of the fields of the procedure in any of the Erows processors. Communication can be carried out, as noted above, by using a small amount of shared memory, the ECache.

When the Conductor processor wants the ERows to run its procedure it writes a MethodID into the ECache. If there is any other data that the EMatrix needs, those data are also written into the ECache. The Conductor does not address the ERows individually. It merely triggers the Erows processors to run. This trigger could be as primitive as an electric pulse. Upon being triggered to act, each ERow runs its procedure. This procedure looks into the ECache to determine which case statement, which we call a method, in the procedure to run. All ERows run the same method. When the procedure is completed each ERow will have written into the ECache any data that must be returned to the Conductor processor.

The ERows can run entirely in parallel because they can have the following properties.

1. The ERows are self indexing. Each contains an ID field that is unique to each ERow. In some cases the method run by all ERows results in exactly the same action in each ERow, or one ERow takes action and the other ERows do nothing, or one ERow takes no action and all other ERows take the same action. For this reason the ERows do not have to be addressed by the Conductor. Each ERow can compare its ID field with the RowID field in the cache to determine whether it takes action or takes no action.
2. They are autonomous. Each contains its own copy of the code it runs. It does not have to be handed any instructions by the Conductor.
3. The Rows are entirely independent. No ERow reads from or writes into the fields of any other ERow.
4. In a multi-processor arrangement, if there are enough processor cores to provide one core for each Erow, the cores can run in parallel. If there are not enough cores to provide one core for each ERow, they can be divided into groups of approximately equal size and each group can be assigned to a core. They can be run serially on each core. Since the Conductor processor does not have to address the ERows individually, they can be allocated in any way that the available hardware will support. The only requirement is that each ERow must be able to read from the ECache and write to the ECache.
5. With that overview of the EMatrix, we can now focus on some of the more particular features, in accordance with one embodiment. As noted earlier, the EMatrix is organized into a collection of rows, each referred to as an ERow. Each ERow is conceptually an object in the sense that this term is used in object oriented programming Each ERow contains the data for which it is responsible and it contains all the methods needed to manipulate its data. It is encapsulated. Massive parallelism is attainable when each ERow is implemented as a hardware processor.
6. The fields in each ERow are implemented as registers, not in RAM. To achieve speed their contents do not have to be moved from RAM to a processor for manipulation. The fields of each ERow are
TERow=class (TObject)
ID:integer;
Row:TRow;
ppp:extended; // we use multiple character names for variables
rrr:extended;
procedure Action;
end;
The ID field is an integer that identifies the row of the E matrix that each ERow represents. The Row field contains the entries in the row of the E matrix that each ERow is responsible for.

VSM can be divided functionally into two parts. The host, which we call the Conductor processor, can be implemented in computer code by a processor and can perform all the decision making. The device, which we call the EMatrix, can be implemented in hardware (or emulated in software) and can perform all the computation. The Conductor processor and the EMatrix communicate by writing to and reading from a small shared memory called the ECache. They can read information from the ECache or they can write information into the ECache. Neither one can see or address the other directly. The fields of the ECache are
  TECache=record
  RowID:integer;
  MethodID:integer;
  AColumn:TAColumn;
  BColumn:TEColumn;
  EColumn:TEColumn;
  RColumn:TEColumn;
  ERow:TRow;
  PivColumnInE:integer;
  VirtualERow:TRow;
  ObjectiveERow:TRow;
  end;
Note that each ERow has one procedure, Action. This procedure is the same for all ERows. It is a case statement (in Pascal) or a switch (in C) for example. Each case is a method. These will be described where we discuss their implementation.
1. InitializeE
Immediately after a new problem is imported it must be initialized. The Conductor processor writes MethodID=InitializeE=1 into ECache.MethodID and triggers the ERows to action.

```
1: begin // InitializeE
    for i:=0 to MaxRow do
        Row[i]:=0;
        if ID>=0 then
            Row[ID]:=1;
    end;
```

Each ERow writes into the entries in its Row field, as specified in the Action procedure. The result is that, collectively, the ERows constitute a matrix in which the row with index −1 is all zeros and the remaining rows form an identity matrix. The InitializateE method illustrates the first type.
2. doBUpdate
When a problem is imported the RHS is written into ECache.BColumn. This column remains unchanged throughout a run unless it is changed by deliberate editing. The Conductor writes doBUpdate=5 into ECache.MethodID and triggers the ERows to action.

```
5: begin // doBUpdate
    Row[−1] := 0;
    for i := 0 to MaxRow do
        Row [−1] := Row[−1] + ECache.BColumn[i]*Row[i];
    ECache.EColumn[ID] := Row[−1];
    end;
```

Each ERow computes the inner product of its Row and ECache.BColumn and enters the result in its b field. (This field does not explicitly appear in the structure of the ERow. It is the −1 entry in its Row field.) Each ERow writes its b entry into its entry in ECache.EColumn. Since at this beginning of a VSM run the E matrix is an identity matrix the same end could have been achieved by copying ECache.BColumn. However, this operation is needed later in a run when the E matrix is no longer an identity matrix.

The Conductor examines ECache.EColumn to see if any of the entries are negative. If at least one is negative the Conductor executes a ForceFeasible. It does this by constructing a pivot column in ECache.EColumn. The entries in this column are all zeros except for a 1 in the Virtual row and a −1 in each row with a negative entry in ECache.EColumn. The Conductor chooses as the pivot row the row with the most negative entry. The Conductor then writes the index of the pivot row into ECache.RowID and GetPivotColumn=3 into ECache.MethodID and triggers the ERows.

```
3: begin // GetPivotColumn
    ppp:=ECache.EColumn[ID];
    end;
```

The entries in ppp constitute a pivot column. The Conductor then triggers the ERows to perform a pivot exchange. We will explain the details of this operation later.
3. ForceNonBasic
The Conductor processor then examines the basic variables to see if any are artificial. A variable can be designated as artificial, for example, when it corresponds to a constraint of the original problem and the constraint is an equality rather than an inequality. For each basic artificial variables the Conductor processor writes the row index into ECache.RowID and PutERow=2 into ECache.MethodID and triggers the ERows.

```
2:begin // PutERow
    if ID=ECache.RowID then
        ECache.ERow:=Row;
    end;
```

The ERow identified as the pivot writes its Row field into ECache.ERow. The Conductor processor then writes ForceNonBasic=11 into ECache.MethodID and triggers the ERows.

```
11: begin //ForceNonBasic
      if ID = −1 then
        begin
          for i := −1 to MaxRow do
            Row[i] := Row[i] − ECache.ERow[i];
          ECache.VirtualRow := Row;
        end;
    end;
```

This operation is actually equivalent to a pivot exchange using a pivot column with zeros except for 1's in the virtual row and the basic row. The ForceNonBasic operation is slightly simpler and performs the same task. The operation makes the artificial variable non basic and creates a virtual variable that is not associated with the row. When this operation is performed for each artificial variable the problem is initialized.

As noted earlier, the status of variables can be maintained as arrays. Thus, for example, one can keep track of which variables are basic, virtual, free, artificial, and canonical.

4. Pivot Exchange in the E Matrix

At the completion of a pivot exchange the last method to run copies the Row field of the virtual ERow to ECache.VirtualERow and the Row field of the optimization ERow to ECache.ObjectiveERow. They serve as selectors used by the Conductor processor to select a pivot column in the E Matrix. It writes the index of this column into ECache.PivotColumnInE, GetPivotColumnInE=4 into ECache.PivotColumnInE and triggers the ERows.

```
4: begin // GetPivotColumnInE
     ppp := Row[ECache.PivColumnInE];
     if (ppp > ECache.Epsilon) and (ID > 0) then
       rrr := Row[−1]/ppp
     else rrr := −1;
     ECache.RColumn[ID] := rrr;
   end;
```

Each ERow copies the entry in Row[PivotColumnInE] into its ppp field. This creates a pivot column that is a copy of the selected column Each ERow for which its ppp>0 writes the ratio Row[PivotColumnInE]/ppp into its rrr field. Otherwise, each ERow writes −1 into its rrr field. The rrr field is then written to ECache.RColumn[ID].

The Conductor processor uses the entries in ECache.RColumn to select a pivot row. For each row associated with a free variable the Conductor processor overwrites the RColumn entry for that row with −1. This makes the rows associated with free variables ineligible for selection. The Conductor processor selects the row with the smallest positive RColumn entry as the pivot row.

With the entries in the pivot column in place in the ppp fields of the ERows and the pivot row selected the Conductor processor takes steps to perform the pivot exchange. The Conductor processor writes the index of the selected pivot row into ECache.RowID, NewPivotRow=7 into ECache.MethodID and triggers the ERows.

```
7: begin // NewPivotRow;
     with ECache do
       if ID = RowID then
         begin
           ppp := 1/ppp;
           for i := −1 to MaxRow do
             Row[i] := Row[i]*ppp;
           ERow := Row;
         end;
     end;
```

The only ERow that takes action is the ERow whose ID field matches ECache.RowID. That ERow multiplies the entries in its Row field by the reciprocal of its ppp field. It then writes the entries in its Row field into ECache.ERow. The Conductor processor then writes NewOtherRow=8 into ECache.MethodED and triggers the ERows.

```
8: begin // NewOtherRow;
     with ECache do
       if ID <> RowID then
         for i := −1 to MaxRow do
           begin
             Row[i] := Row[i] − ppp*ECache.ERow[i];
             if isZero(Row[i], Epsilon)
               then Row[i] := 0;
           end;
       if ID = −1 then ECache.VirtualRow := Row;
       if ID = 0 then ECache.ObjectiveRow := Row;
     end;
```

This operation subtracts ppp times the ECache.ERow, which is the new pivot row, from its Row. This completes the arithmetic for the pivot exchange. The ERows with indices −1 and 0 copy their Row fields in ECache.VirtualRow and ECache.ObjectiveRow. These rows are the column selectors for the next iteration. When this method is completed the pivot exchange is completed.

Because the selectors for a column in the E matrix are always computed and available after every pivot, exchange priority is given to finding a pivot column in the E matrix. VSM repeats looking for a pivot column in the E matrix until it cannot find one. When an eligible pivot column cannot be found in the E matrix VSM turns its attention to trying to find a pivot column in the EA matrix.

5. Pivot Exchange in the EA Matrix

When looking for a pivot column in the EA matrix, the Conductor assembles a collection of candidate columns by multiplying the A matrix by the E matrix. These columns are formed into a matrix which we denote by A' (sometimes referred to herein as the EA matrix). Let S denote the two-row matrix formed by the selectors for the E columns. The matrix product SA' constitutes a two-row matrix whose entries are used as the selectors for the A columns. How the columns that make up A' are chosen is optional, but the default used by VSM is to choose the columns following the column used for the last previous pivot exchange and including as many columns as will allow the entries in SA' to be computed in parallel. If a pivot column cannot be found another collection of candidates is selected. When every column has been scanned without finding a pivot column the run is terminated.

If the Conductor processor finds a pivot column it writes the entries in that column into ECache.AColumn. It then writes Computeppp=6 into ECache.MethodID and triggers the ERows.

```
6: begin // Computeppp
     ppp := 0;
     for i := 0 to MaxRow do
       ppp := ppp + ECache.AColumn[i]*Row[i];
```

-continued

```
        if ID = -1 then
           if isZero(ppp) then
              ECache.HSelector := 0
           else ECache.HSelector := ppp;
           if (ppp > ECache.Epsilon) and (ID > 0) then
              rrr := Row [-1]/ppp
           else rrr := -1;
           ECache.RColumn[ID] := rrr;
        end;
```

The ERows compute their ppp fields, their rrr fields, and write the results into ECache.RColumn. At this point a pivot row is selected and a pivot exchange will be carried out just as has been described for a pivot exchange in the E matrix.

6. bUpdate, ForceFeasible

Computer error compromises the accuracy of the offered answer primarily in two ways. If the original constraints are in the form Ax=b a later representation will be in the form A'x=b' where both A' and b' are produced by the calculations. Because of computer error the representation A'x=b' will not be equivalent to the original representation. They will not have the same solution sets. The revised simplex method will produce the representation EAx=b' where both E and b' are produced by the calculations. This representation suffers the same criticism.

VSM uses bUpdate to replace b' by EB. The constraints are then represented by EAx=EB which is equivalent to the original constraints. This operation is available for any version of the simplex algorithm. However, there is danger that the errors might be large enough that EB will have negative entries. When that happens the run has gone infeasible and the run fails. VSM has ForceFeasible available. ForceFeasible restores feasibility at the expense of introducing a basic virtual variable. However, the problem is still in basic feasible form and the run can continue. VSM will attempt to make a pivot exchange that will make the virtual variable non basic. If the problem was feasible before the update VSM will succeed in restoring basic feasible form.

The way VSM carries this out has been described where it was used in the initialization stop. The operation can be performed optionally at any time.

7. ForceNonBasic, Pivot-in-Place

To carry out a Pivot-in-Place the Conductor processor first executes a ForceNonBasic. A ForceNonBasic is equivalent to a pivot exchange in which the pivot column entries are all zeros except for a 1 in the virtual row and a 1 in the basic row. Since this is always the pivot column it is slightly simpler to subtract the basic row from the virtual row. To do this the Conductor writes PutERow into ECache.MethodID=2, the index of the basic row into ECache.ERow and triggers the ERows. The selected ERow write its Row into ECache.ERow. The Conductor then writes ForceNonBasic=11 into ECache.MethodID and triggers the ERows.

When this operation is completed the column that was basic becomes non basic and VSM scans the columns exactly as it would any other non basic column. If the same column is selected as a pivot column and the same row is selected as a pivot row the result is that there is no exchange. The basic set obtained is the same as it was before the ForceNonBasisc. We call the result a Pivot-in-Place (PIP). If there are errors or edits sufficient to select a different pivot column or pivot row the introduced virtual variable will remain basic and VSM will try to make the virtual variable non basic. In this way the integrity of the run is maintained. In other simplex-like methods the selection of a different pivot element would cause the run to fail.

8. Null Virtual Row

Computer error can occur in calculating the entries in the virtual row. The virtual objective function is the sum of the virtual variables. Thus, the virtual row can be restored at any time by replacing it by the negative of the sum of the rows of the E matrix associated with basic virtual variables. This operation is not required in VSM though it could be implemented if experience indicates a need for such a remedy.

This operation could be done intermittently, such as once a circuit. Computer errors may have accumulated in the rows of the basic virtual variables. That means that basic virtual variables are not exactly what they were when they were first introduced. It is the existence of virtual variables that is important, not their values.

VSM tracks the number of basic virtual variables. It needs this information to determine whether the optimization problem is feasible at termination. VSM takes advantage of this count to take corrective action whenever the number of basic virtual variables goes to zero. When that happens the Conductor processor writes NullVirtualRow=13 into ECache.MathodID and triggers the ERows.

```
        13: begin // NullVirtualRow
           if ID = -1 then
              for i := 0 to MaxRow do
                 Row[i] := 0;
           end;
```

The virtual ERow nulls all its entries. That is the correct set of values when the number of basic virtual variables is zero.

9. Free Variables

Free variables must be handled differently from canonical variables. The first difference is that a non basic free column qualifies for a pivot column regardless of the values of its selectors. If the rules used for canonical variables apply then there is no need for special treatment. If positive pivot entry for a pivot row cannot be found VSM must search for a suitable negative pivot entry. The Conductor processor writes ComputeNegativerrr=9 into ECache.MethodID and triggers the ERows.

```
        9: begin // ComputeNegativerrr
           if (ppp<0) and (ID>0) then rrr:=-Row[-1]/ppp
              else rrr:=-1;
           ECache.RColumn[ID]:=rrr;
        end;
```

The ERows compute negative ratios that are used to determine the pivot row.

The other difference is caused by the fact that a free variable can be negative. The Conductor processor writes PutPositiveERow=12 into ECache,MethodID and triggers the ERows.

```
        12: begin // PutPositiveERow
           with ECache do
              if ID = ECache.RowID then
                 begin
                    if Row[-1] < 0 then
                       for i := -1 to MaxRow do
                          Row[i] := -Row[i];
                    ERow := Row;
                 end;
           end;
```

If the b entry is negative the ERow will change the signs in the Row before writing it into the ECache.

10. Reporting an Answer

During a run the Conductor processor does not see any of the entries in the ERows, including the b column. It does not need to know these numbers to make its decisions. All it needs are the reported ratios and the selectors. This also means that the Conductor processor does not know the numbers in a potential offered answer. The bUpdate operation updates the entries in the b column and writes the b column into ECache.EColumn There, it is available for reporting the result using bUpdate.

11. Self Indexing and Autonomy

The ID field of each ERow allows the ERow to identify itself. It is self-indexed. It does not have to be addressed. When an ERow is triggered to action it looks at its environment, the ECache, to determine what actions it is to take. This allows the ERows, embodied as processors, to run simultaneously, in parallel. Each decides for itself what it is to do.

12. Synchronization

In accordance with one embodiment, when it is necessary for all threads in parallel code to complete a task before they can continue, standard practice is to insert a barrier at that point in each thread. When a thread reaches its barrier it halts. When all have reached their barriers all are restarted. The times between required synchronizations in VSM are so short that the use of barriers would impose a severe burden on computer resources. VSM runs a single procedure once at each trigger that is always synchronized so it can maintain synchronization without using barriers. VSM provides a redundant Erow, called the pacing Erow, that responds to the trigger as all ERows do. Its procedure is similar to the common procedure shared by all other ERows. Each of the Redundant eRow methods takes as many clock cycles as the largest number of clock cycles required by the other eRows. When this ERow completes its method all the ERows will also have completed their ERows. When this pacing ERow reports that it has completed its procedure the Conductor processor can issue another trigger. The ERows will maintain synchrony without barriers.

IV. Examples

Figure 1B:
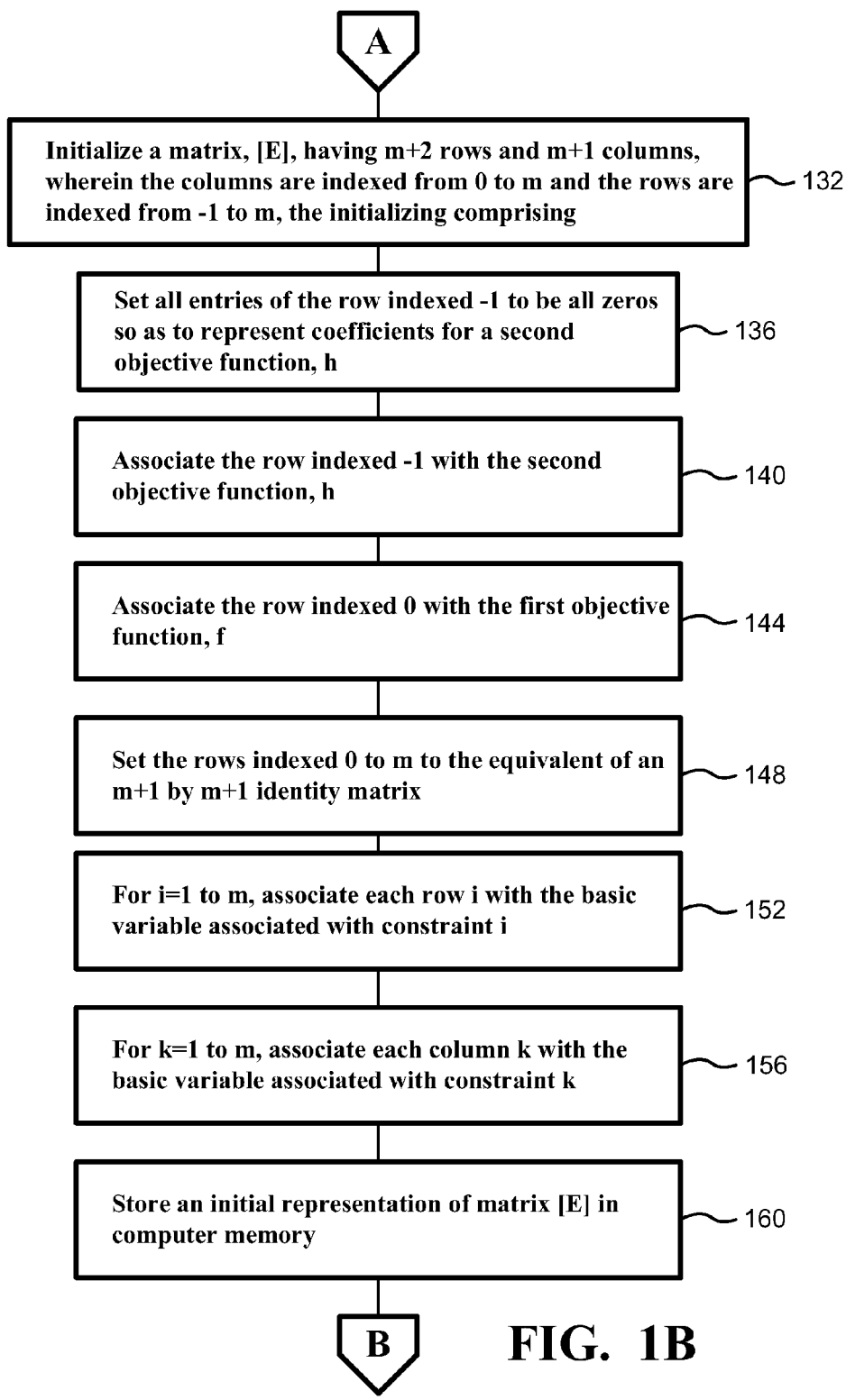
Figure 1C:
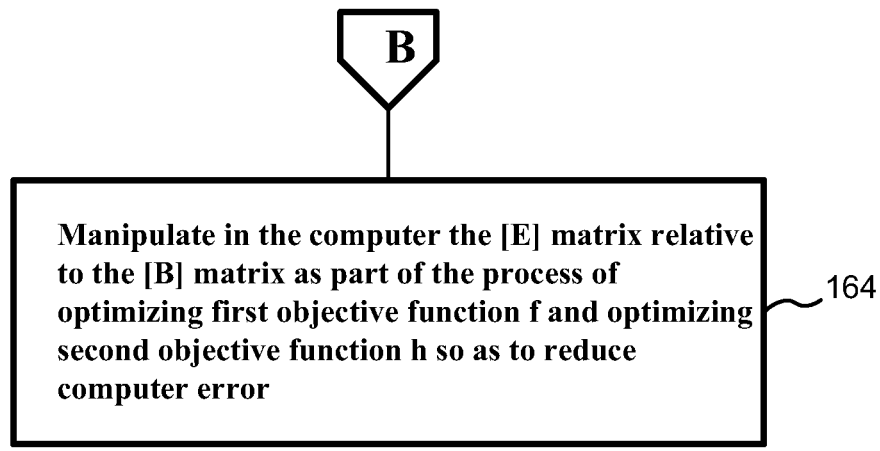

Referring now to the figures, some examples implementing embodiments of the invention described above can be seen. FIGS. 1A, 1B, and 1C illustrate a flowchart 100 demonstrating a method of setting up a linear programming problem for processing by a computer in a manner that will reduce the possibility of computer error. In block 104, a first objective function, f, is provided for optimization. The problem can be input by a user, for example. Furthermore, "m" constraints can be provided for the objective function, as shown in block 108. Each constraint that is originally provided as an equality can be associated with a basic artificial variable and the association can be stored in memory, as shown by block 112. Each constraint in the form of an inequality can be converted to the form of an equality. This can be done, for example, by adding a slack variable $Y_i$ wherein $Y_i$ is greater than or equal to zero and wherein $Y_i$ is considered to be a basic variable, as shown by block 116. Furthermore, the linear programming problem can be arranged in the format [A][X]+[I][Y]=[B]. Matrix [A] represents the coefficients for the variables in matrix [X]. Matrix [Y] represents the variables $Y_i$ for i=1 to m. Matrix [I] represents the identity matrix. And, matrix [B] represents a matrix of numbers. This is shown by block 120. In block 124, the coefficients for matrix [A] are stored in computer memory. Also, the values of matrix [B] are stored in computer memory, as shown by block 128.

A matrix [E] can be created and initialized. The [E] matrix can have m+2 rows and m+1 columns. The columns can be indexed from 0 to m and the rows can be indexed from −1 to m, as shown in block 132. All entries of the row indexed −1 of the [E] matrix can be set to zeros. These entries represent coefficients for a second objective function referred to in this example as "h" or the "h-function." This is shown in block 136. And, block 140 shows that this row of the [E] matrix indexed as −1 is associated with that second objective function h. The row of the [E] matrix indexed as 0 can be associated with the first objective function, which is referred to in this example as "f." This is shown by block 144. In block 148, the rows of the [E] matrix indexed from 0 to "m" are set to the equivalent of an m+1 by m+1 identity matrix. Also, for i=1 to m, each row "i" of the [E] matrix is associated with the basic variable that corresponds to the respective constraint "i" in the set of m constraints noted in block 108. This is shown in block 152. Similarly, for k=1 to m, each column k of the [E] matrix can be associated with the basic variable that corresponds to the respective constraint "k" in the set of m constraints noted in block 108, as shown in block 156.

Block 160 illustrates that an initial representation of matrix [E] can be stored in computer memory. Once established, the [E] matrix is useful in reducing computer error during the processing of the linear programming problem. Due to errors caused by the physical limitations of any computer, such errors can be introduced. As explained throughout this specification, the [E] matrix permits errors to be reduced during the processing. Thus, block 164 illustrates that the [E] matrix is manipulated as part of the process of optimizing the first objective function f and optimizing the second objective function h so as to reduce computer error. For example, the [E] matrix can be manipulated relative to the [B] matrix.

Figure 2A:
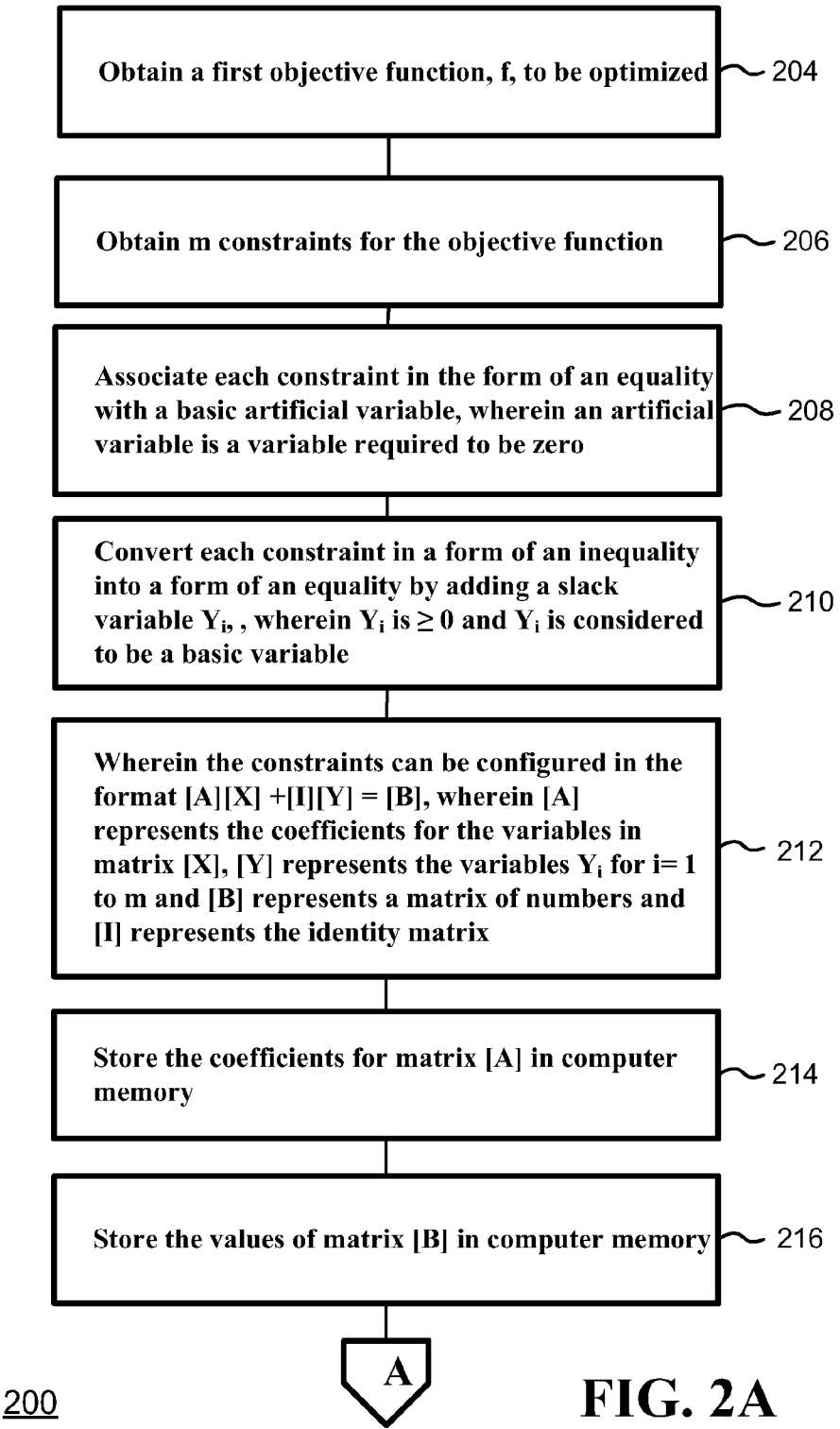
FIGS. 2A, 2B, 2C, 2D, 2E, and 2F are another example of a flowchart illustrating a method of solving a linear programming problem on a computer in a manner that reduces error introduced by the computer processing, in accordance with one embodiment of the invention.
Figure 2B:
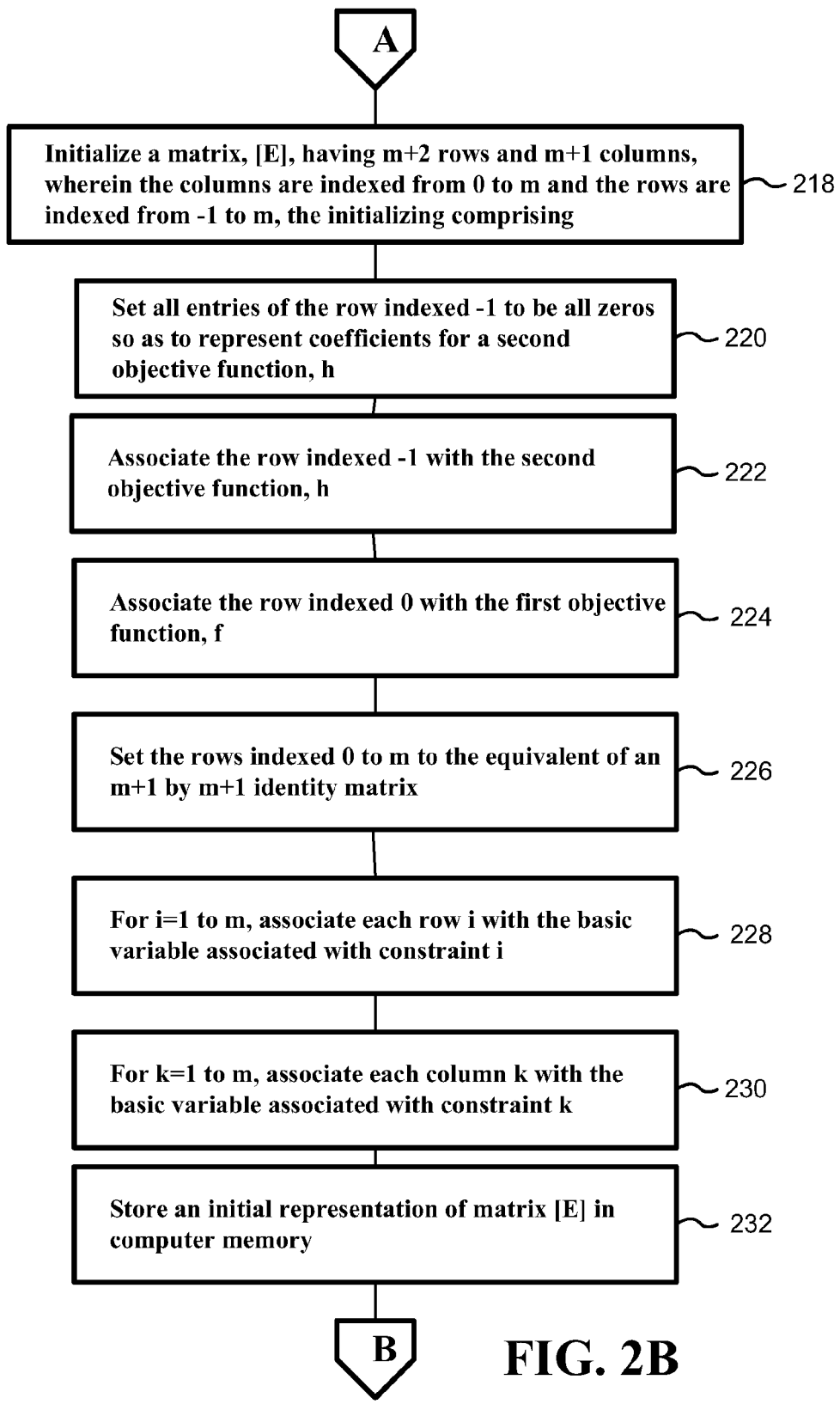
Figure 2C:
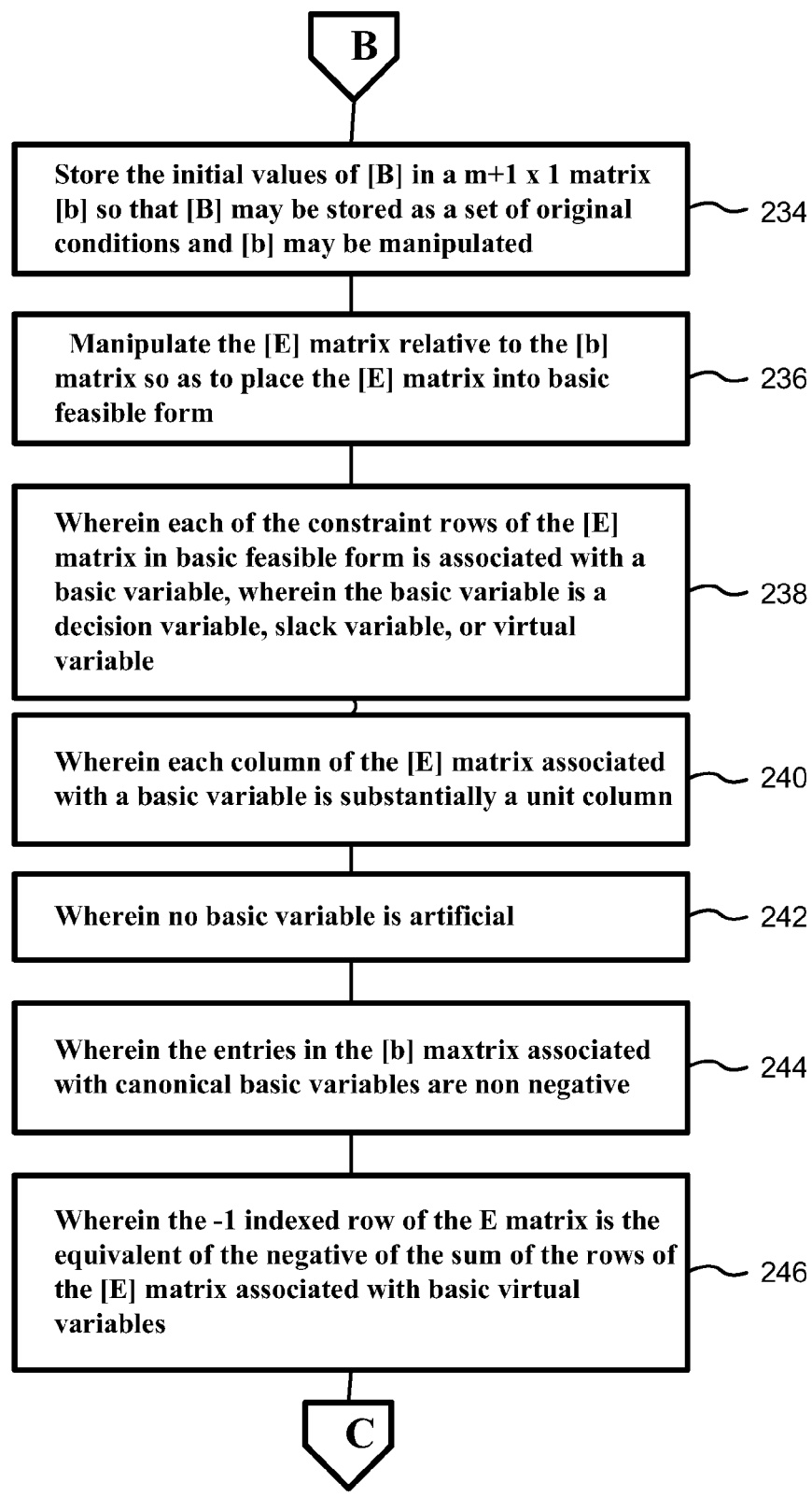
Figure 2D:
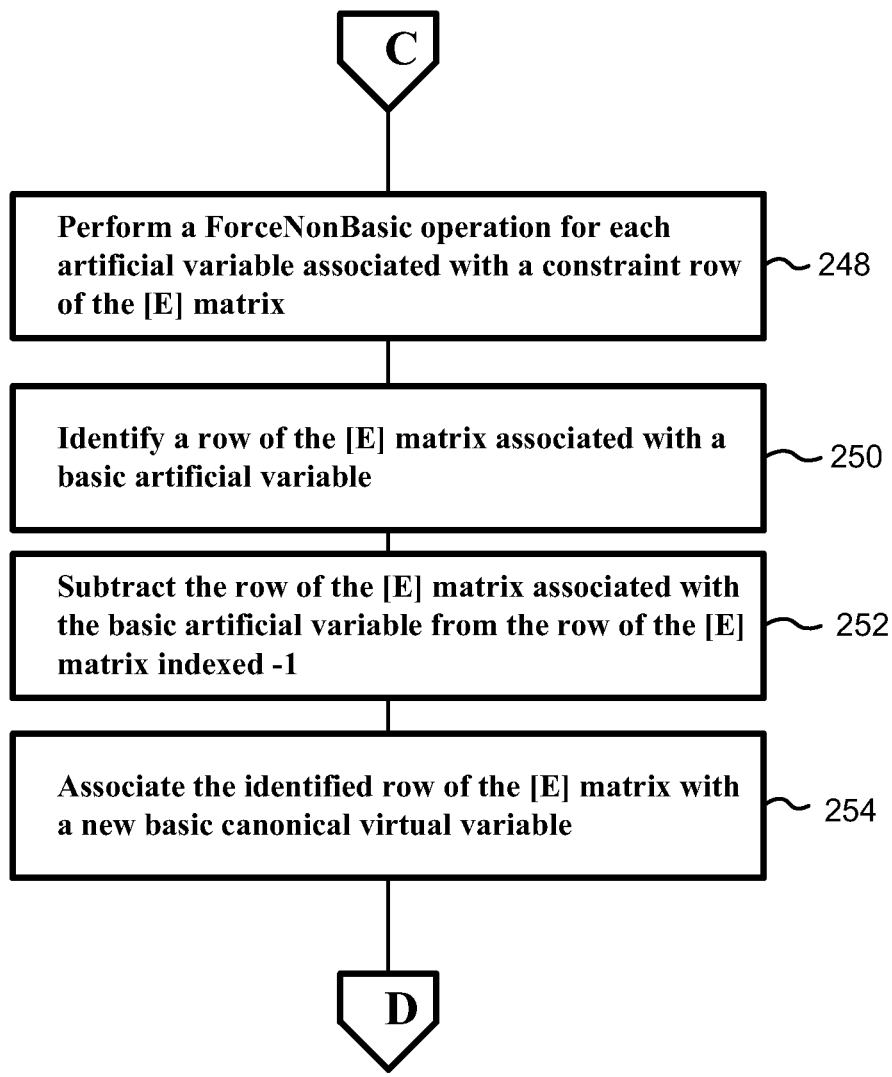
Figure 2E:
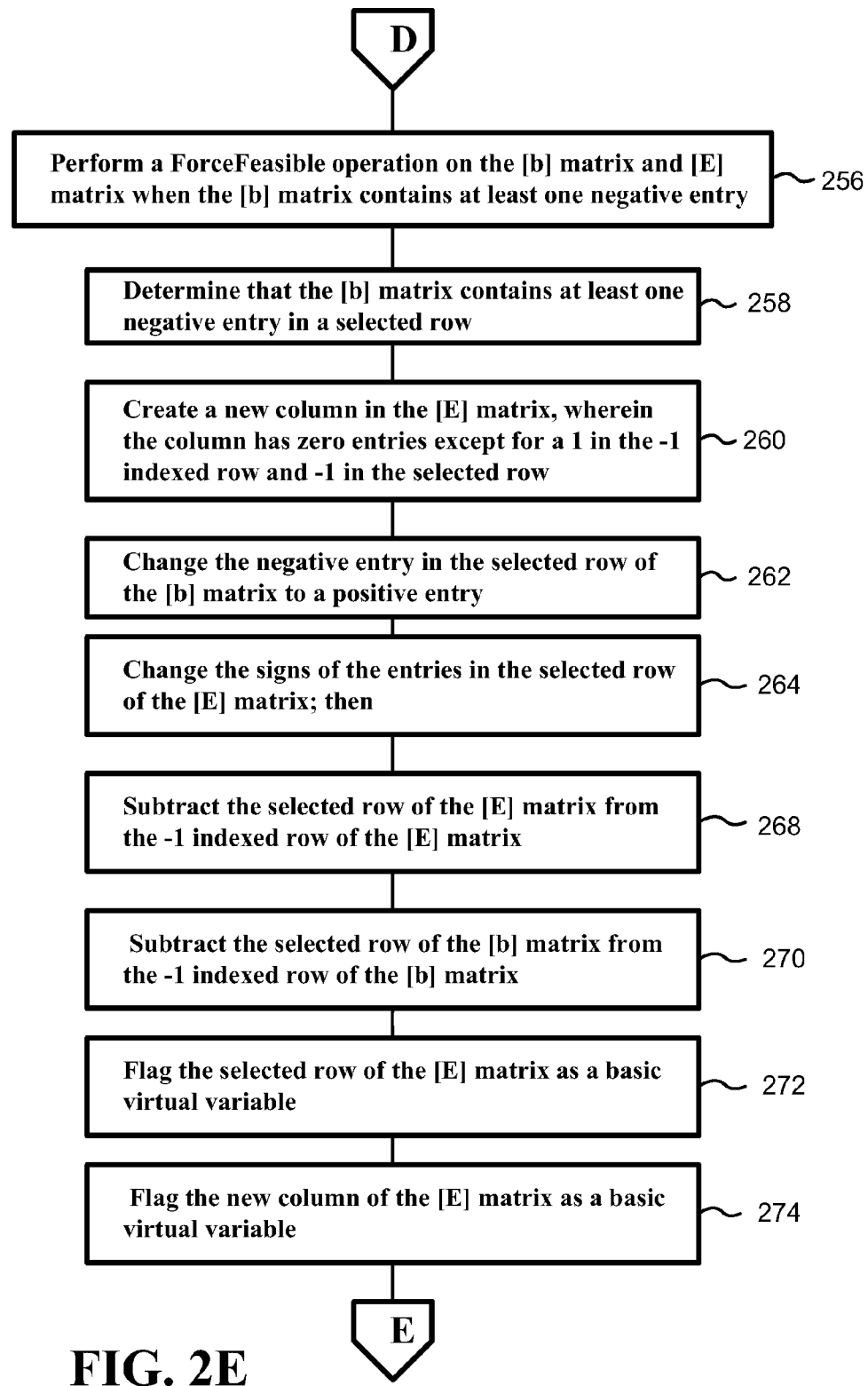
Figure 2F:
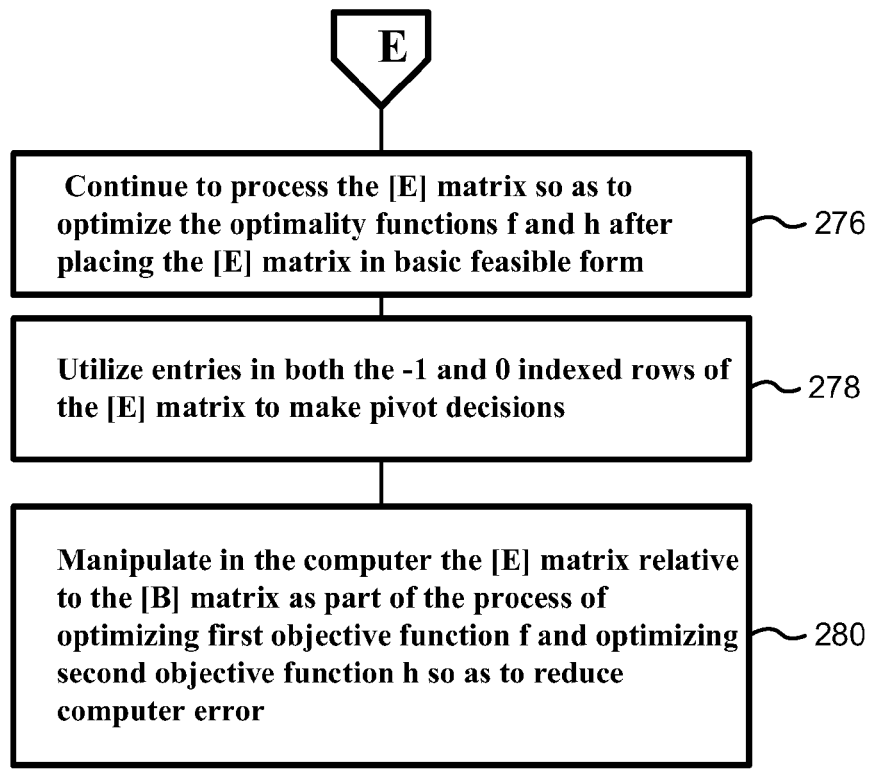

Referring now to flow chart 200 in FIGS. 2A, 2B, 2C, 2D, 2E, and 2F, another example can be seen. FIGS. 2A and 2B repeat the material shown in FIGS. 1A and 1B; so, a description of that material is not repeated again here. In block 234, an m+1×1 matrix [b] is created. The [b] matrix is initially configured to store the values of the [B] matrix. This allows the [B] matrix to store the original set of conditions for [B] and it further allows [b] to be modified during processing.

In block 236, the matrix [E] is manipulated with respect to [b] so as to place the [E] matrix into basic feasible form. When in basic feasible form, each of the constraint rows of the [E] matrix is associated with a basic variable. The basic variable can be a decision variable, a slack variable, or a virtual variable, as shown in block 238. Also, each column of the [E] matrix associated with a basic variable is substantially a unit column, as shown by block 240. Furthermore, no basic variable is artificial, as shown by block 242. And, the entries in the [b] matrix that are associated with canonical basic variables are non-negative, as shown by block 244. The −1 indexed row of the E matrix is the equivalent of the negative sum of the rows of the [E] matrix that are associated with basic virtual variables, as shown by block 246.

A ForceNonBasic operation can be performed on each artificial variable associated with a constraint row of the [E] matrix, as shown in block 248. This can be implemented by identifying a row of the [E] matrix that is associated with a basic artificial variable, as shown by block 250. And, the row of the [E] matrix that is associated with the basic artificial variable can be subtracted from the row of the [E] matrix having an index of −1, as shown in block 252. Also, the identified row of the [E] matrix can be associated with a new basic canonical virtual variable that is introduced, as shown by block 254. As noted above, this can be repeated for each artificial variable that is associated with a constraint row of the [E] matrix.

When a negative entry in the [b] matrix is present, a ForceFeasible operation can be performed, as noted by block 256. The ForceFeasible operation can be performed, for example, by determining that the [b] matrix contains at least one negative entry in a selected row, as shown by block 258. A new column in the [E] matrix can be created wherein the column is assigned values of zero in each row, except that the row indexed −1 and the row corresponding to the selected row of the [b] matrix are assigned a value of −1. This is shown in block 260. The negative entry in the selected row of the [b] matrix is made positive (e.g., multiplied by −1), as shown by block 262. And, the signs of the entries in the row of the [E] matrix corresponding to the selected row of the [b] matrix are reversed (e.g., multiplied by −1), as shown in block 264. In block 268, the selected row of the [E] matrix (i.e., the row that corresponds to the selected row of the [b] matrix) is subtracted from the −1 indexed row of the [E] matrix. And, in block 270, the selected row of the [b] matrix is subtracted from the −1 indexed row of the [b] matrix. In block 272, the selected row of the [E] matrix is flagged as a basic virtual variable. Thus, the selected row is associated with the identity of basic virtual variable and this association is stored in computer memory. Similarly, in block 274, the new column of the [E] matrix is flagged as a basic virtual variable. If additional negative values are present in the [b] matrix, the process can be repeated. If conditions change and a negative value occurs in the [b] matrix, the process can also be repeated.

Block 276 shows that the [E] matrix can continue to be processed by the computer so as to optimize the optimality functions "f" and "h" once the [E] matrix is placed in basic feasible form. This can be formed as part of a single phase process without the need to discard the initialized problem once basic feasible form is established.

Pivot operations can be performed on the [E] matrix in order to optimize the "f" and "h" functions. Entries in the −1 and 0 indexed rows of the [E] matrix can be used to decide which column of the [E] matrix to pivot, as shown by block 278. Block 280 illustrates that the [E] matrix can be further manipulated to optimize the first objective function "f" and the second objective function "h" so as to reduce computer error.

Figure 3A:
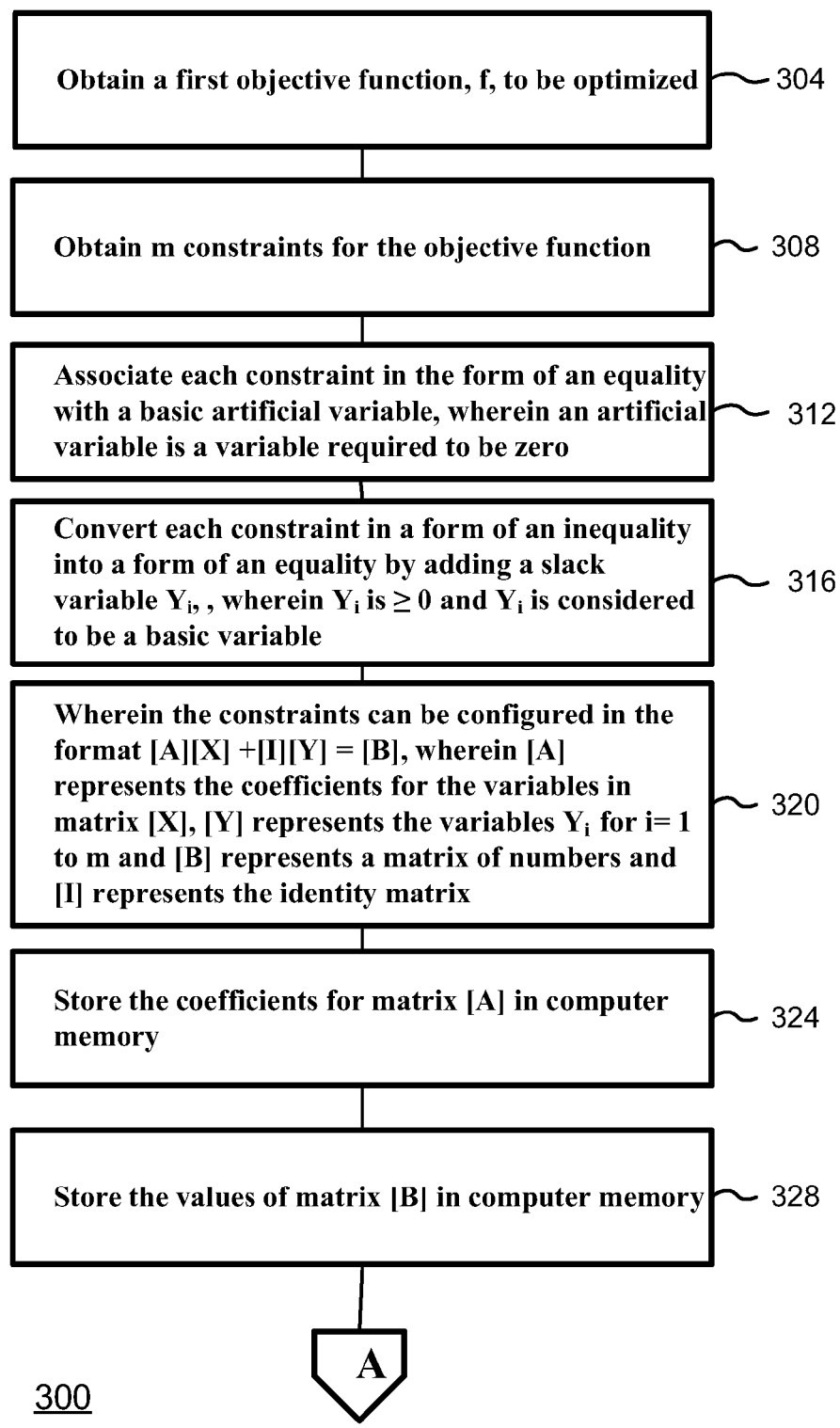
FIGS. 3A, 3B, and 3C are a flowchart illustrating a method of processing a linear programming problem in basic feasible form so as to reduce error introduced by computer processing, in accordance with one embodiment of the invention.
Figure 3B:
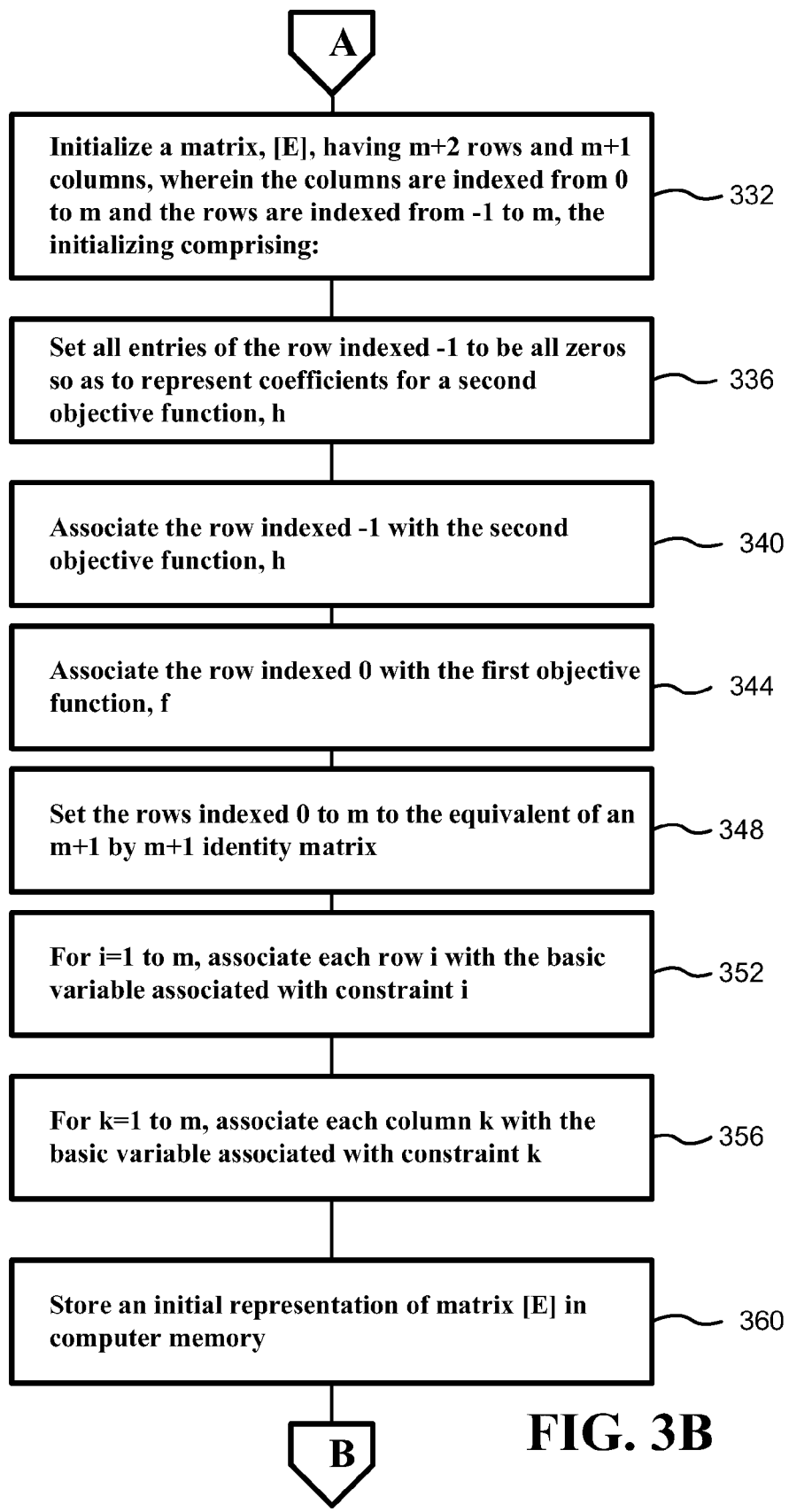
Figure 3C:
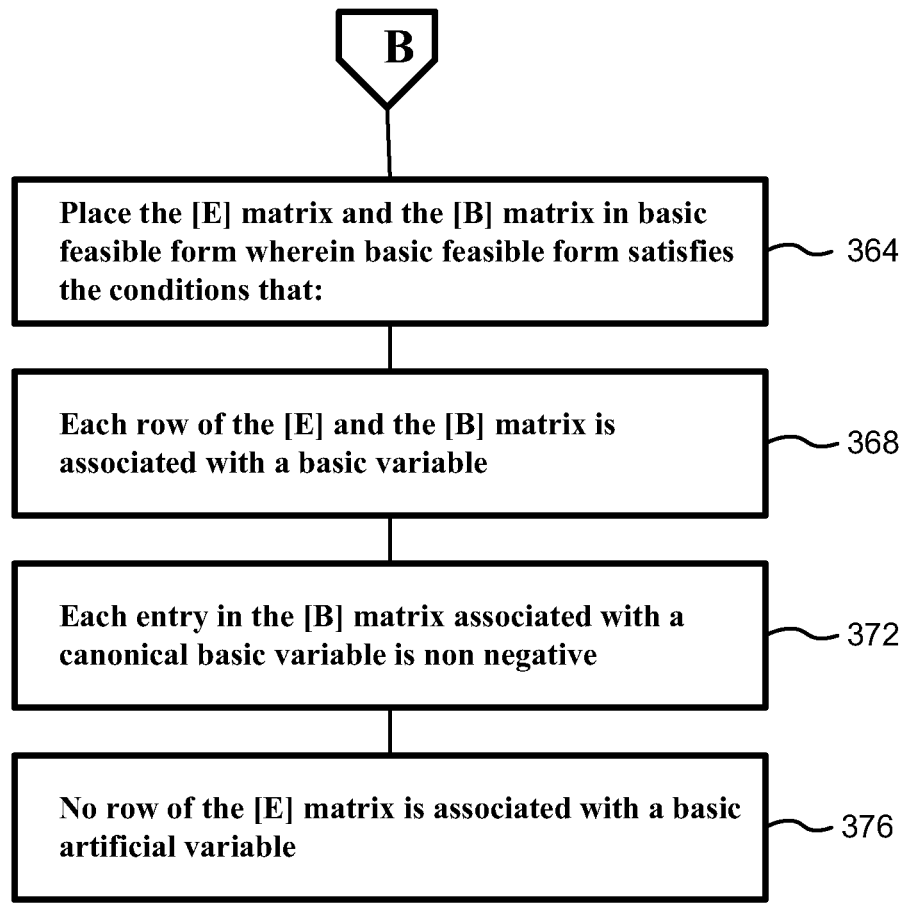

FIGS. 3A, 3B, and 3C show a flow chart 300 that illustrates an example of placing a linear programming problem in basic feasible form for processing by a computer in accordance with one embodiment. FIGS. 3A and 3B repeat the material shown in FIGS. 1A and 1B; so, a description of that material is not repeated again here. In block 364, the [E] matrix can be placed in basic feasible form. As shown in block 368, each row of the [E] and [B] matrices is associated with a basic variable. And, block 372 shows that each entry in the [B] matrix that is associated with a canonical basic variable is non-negative. Also, block 376 shows that no row of the [E] matrix is associated with a basic artificial variable.

Figure 4A:
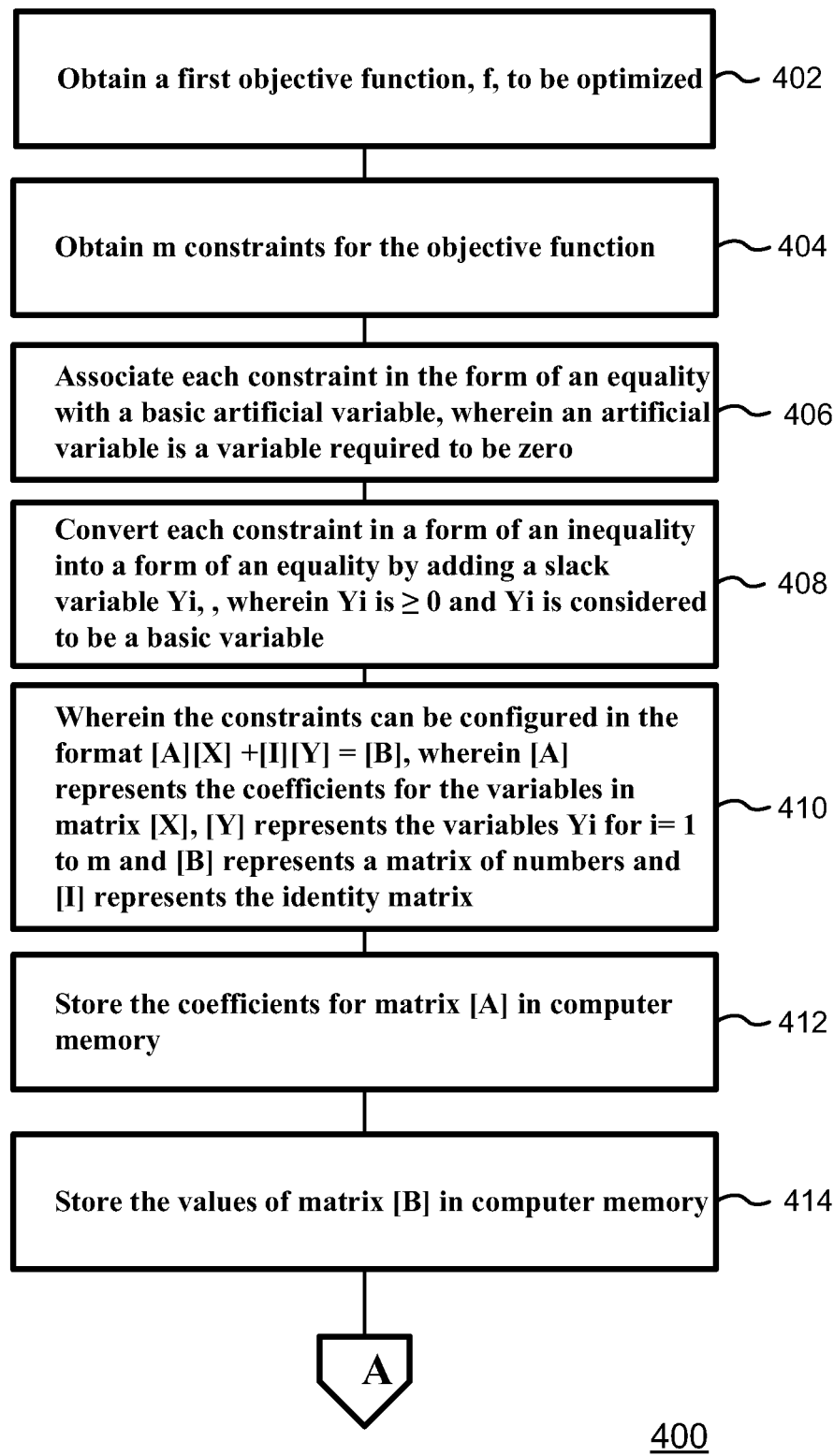
FIGS. 4A, 4B, 4C, 4D, 4E, 4F, and 4G are a flowchart illustrating a method of performing a pivot-in-place operation in accordance with one embodiment of the invention.
Figure 4B:
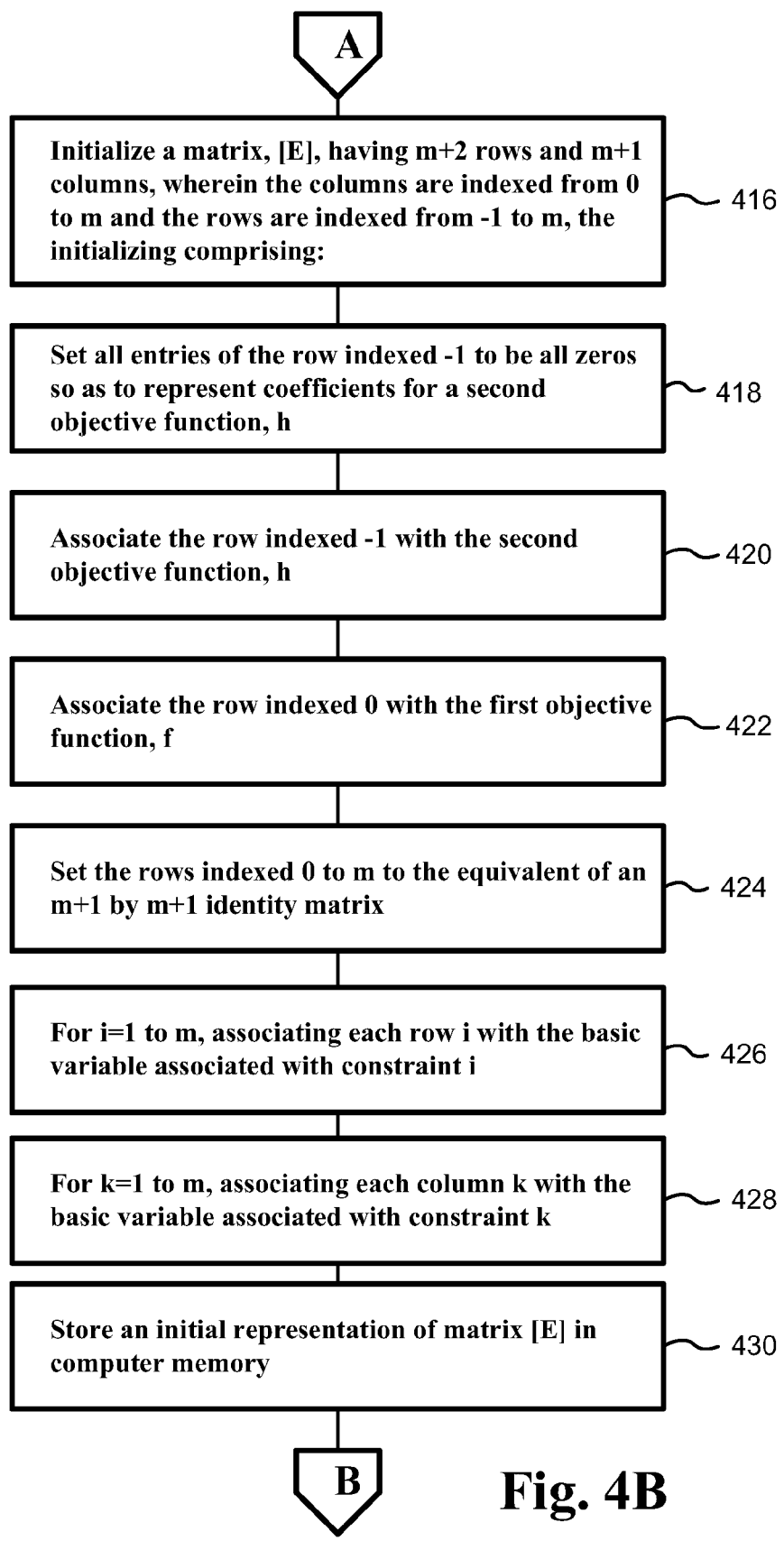
Figure 4C:
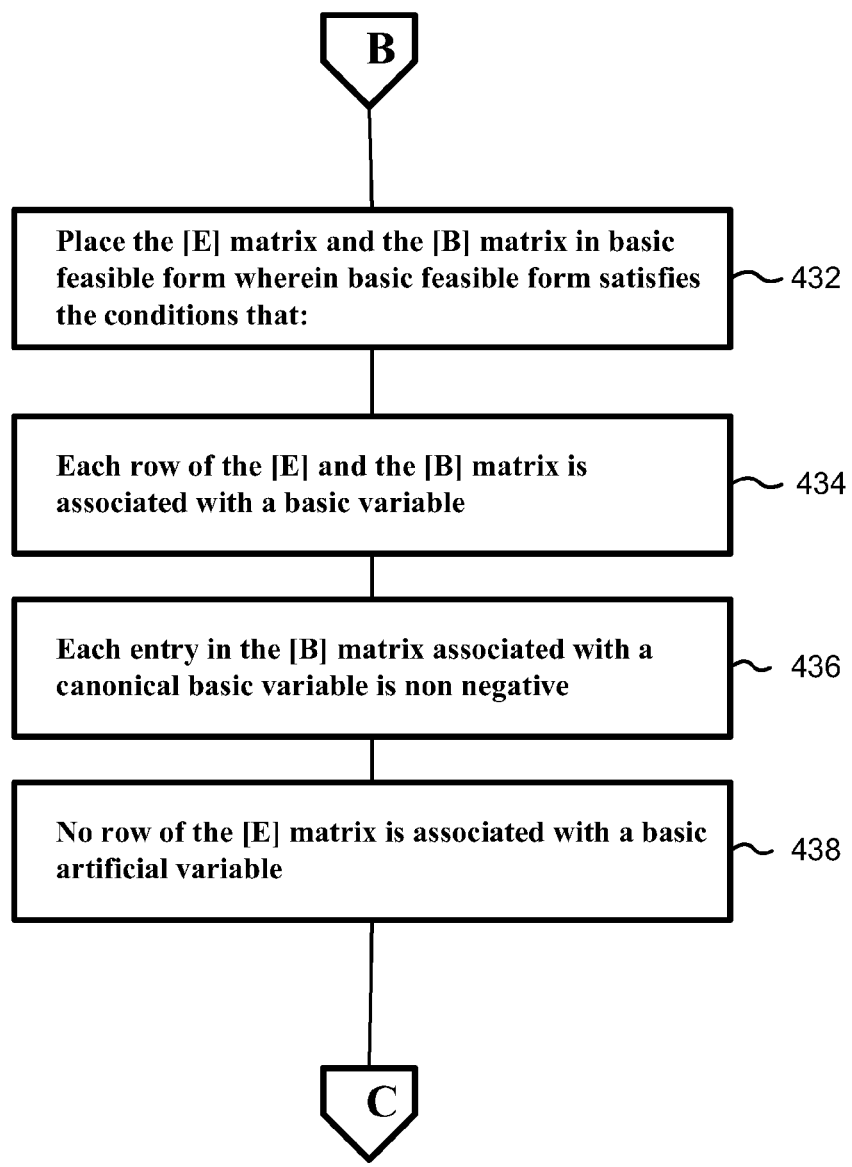
Figure 4D:
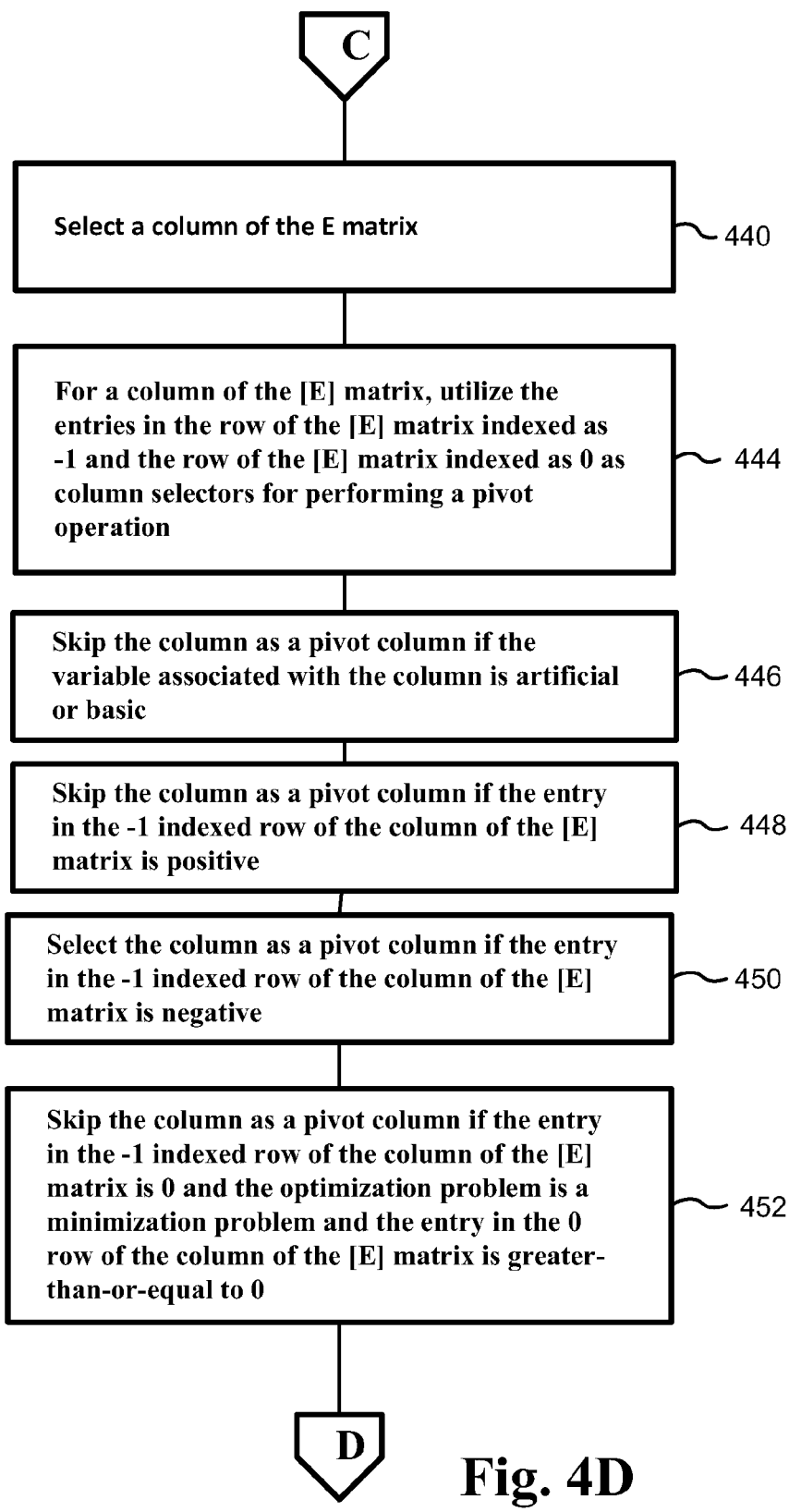
Figure 4E:
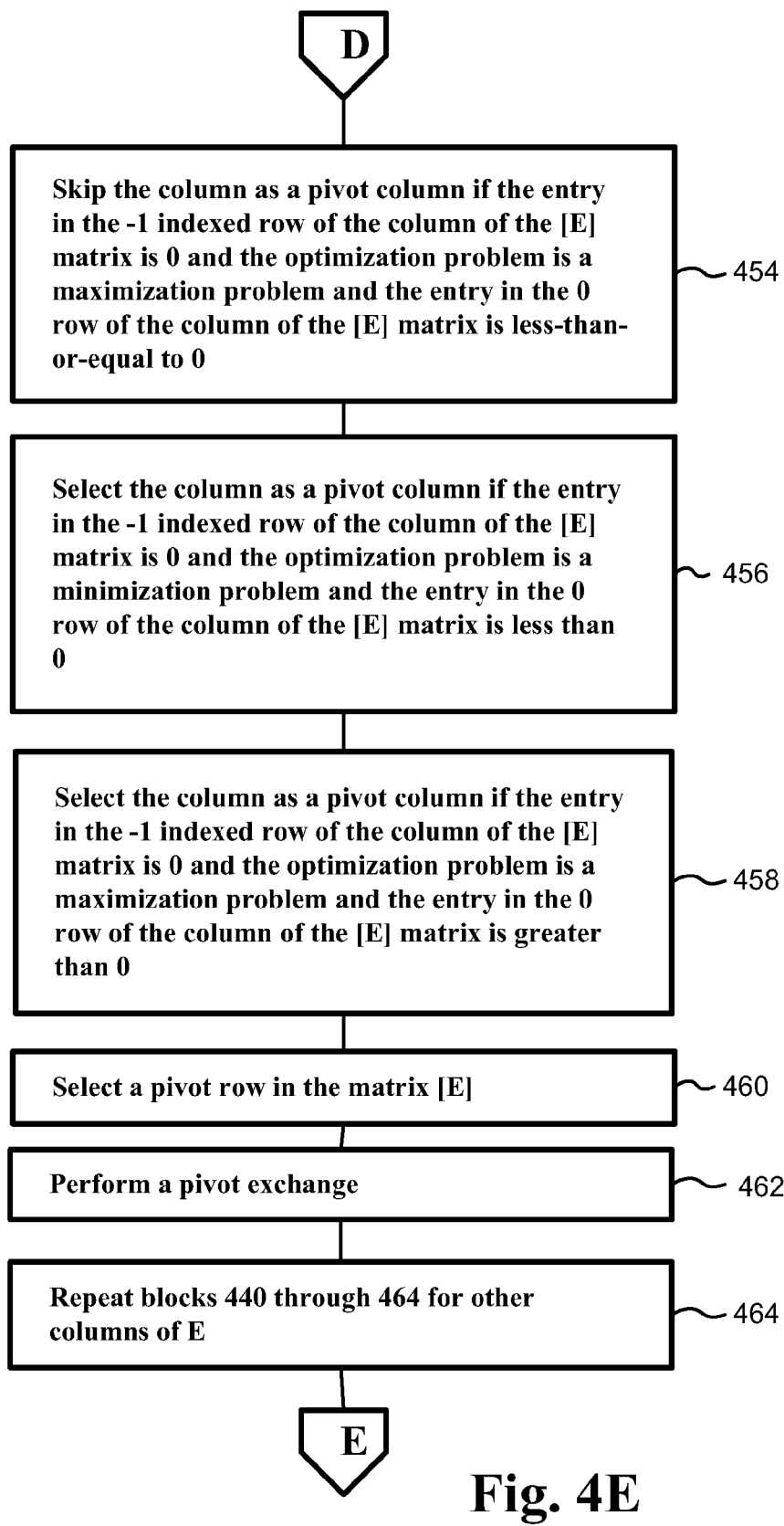
Figure 4F:
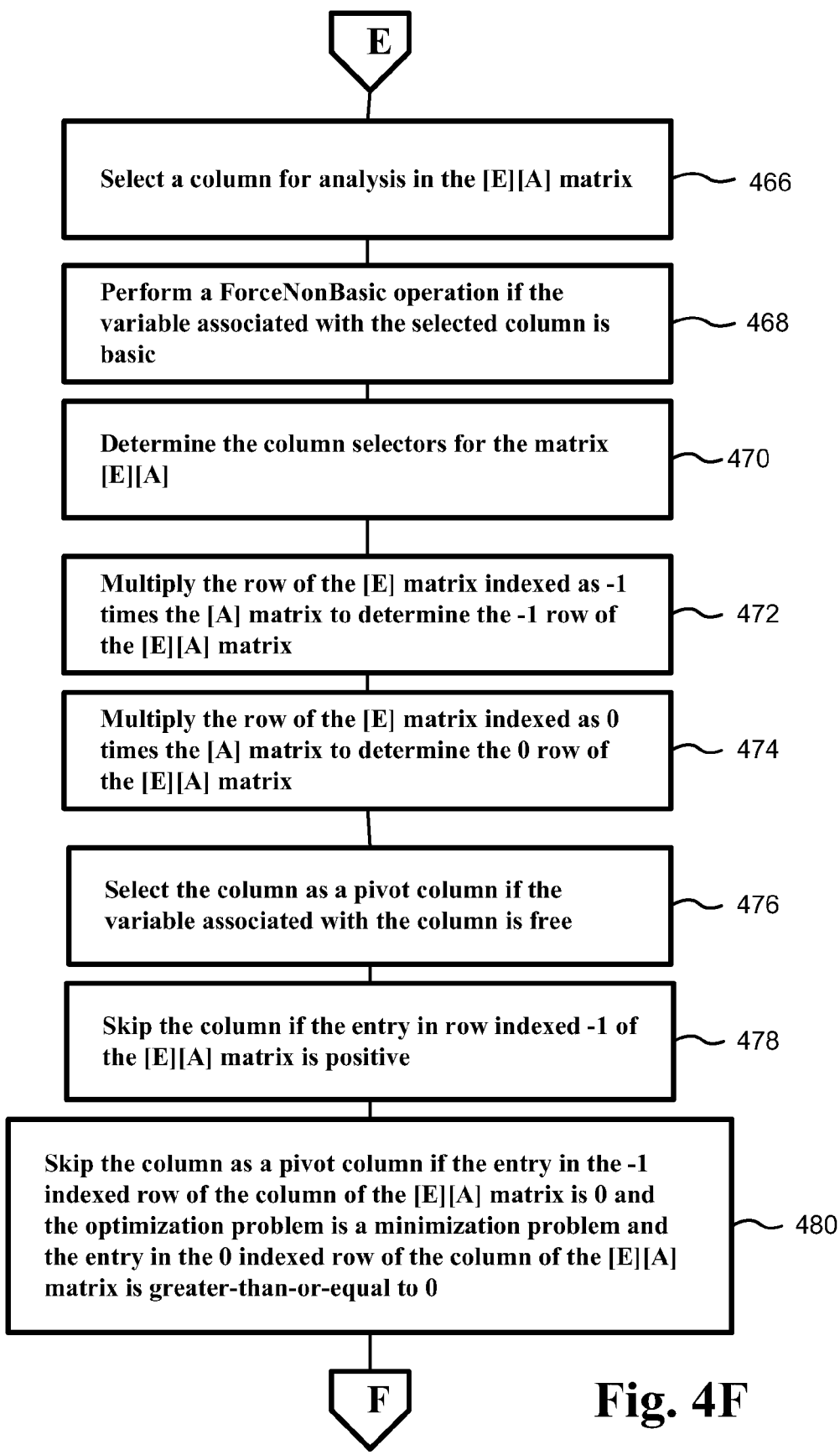
Figure 4G:
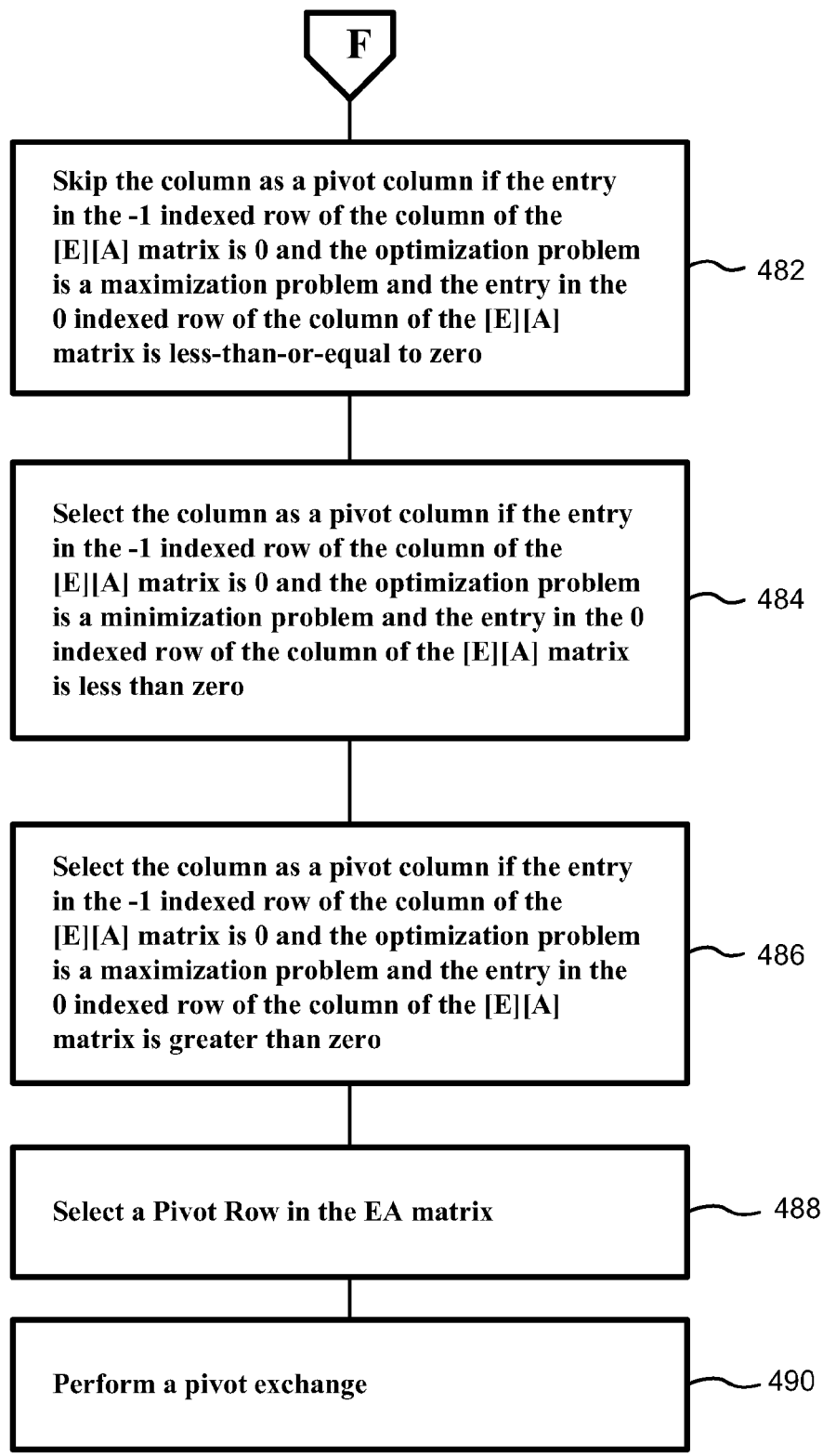

FIGS. 4A, 4B, 4C, 4D, 4E, 4F, and 4G show a flow chart 400 that illustrates an example of performing a Pivot-in-Place operation in accordance with one embodiment of the invention. FIGS. 4A, 4B, and 4C repeat the material shown in FIGS. 3A, 3B, and 3C; so, a description of that material is not repeated again here.

Once the [E] matrix is established in basic feasible form, the columns of the [E] matrix can each be checked. In block 440, a column of the [E] matrix is selected The values stored in the −1 indexed row of the selected column of the [E] matrix and the 0 indexed row of the selected column of the [E] matrix can serve as selectors for determining whether a pivot operation should be performed on the selected column, as illustrated in block 444. The selected column of the [E] matrix can be skipped as a pivot column if the variable associated with the column's index reflects the variable to be an artificial variable or a basic variable. Such information can be determined from a list stored in computer memory. The selected column of the [E] matrix can also be skipped as a pivot column if the entry in the −1 indexed row of the [E] matrix is positive, as shown in block 448. In block 450, the selected column of the [E] matrix can be selected as a pivot column if the entry in the −1 indexed row of the selected column of the [E] matrix is negative.

In block 452, the selected column of the [E] matrix can be skipped as a pivot column if the entry in the −1 indexed row of the column of the [E] matrix is 0 and the optimization problem is a minimization problem and the entry in the 0 indexed row of the selected column of the [E] matrix is greater-than-or-equal to 0.

In block 454, the selected column of the [E] matrix is skipped as a pivot column if the entry in the −1 indexed row of the selected column in [E] is 0 and the optimization problem, f, is a maximization problem and the entry in the 0 indexed row of the selected column of the [E] matrix is less-than-or-equal to 0.

In block 456, the selected column of the [E] matrix is selected as a pivot column if the entry in the −1 indexed row of the column of the [E] matrix is 0 and the optimization problem, f, is a minimization problem and the entry in the 0 indexed row of the selected column of the [E] matrix is less than 0.

In block 458, the selected column of the [E] matrix is selected as a pivot column if the entry in the −1 indexed row of the selected column of the [E] matrix is 0 and the optimization problem is a maximization problem and the entry in the 0 row of the column of the [E] matrix is greater than 0.

If the column under consideration for performing a pivot operation is not selected for a pivot operation, a new column of the [E] matrix can be assessed for whether it should be pivoted. However, if the column under consideration is selected for performing a pivot operation, then a pivot row can be selected. Thus, block 460 shows that a pivot row is selected in matrix [E]. Having established a pivot column and a pivot row in matrix [E], a pivot operation can be performed. This is noted in block 462. Once the pivot operation is completed, the process can be repeated for additional columns of the [E] matrix. Thus, block 464 reflects that the process can be repeated for additional columns of [E].

The EA matrix can be scanned to see if there are any Pivot-in-Place operations that should be performed. In block 466, a column in the [E][A] matrix is selected for analysis. If the variable associated with the selected column is a basic variable, a ForceNonBasic operation is performed, as shown by block 468. A column of [A] and a column of [E][A] are associated with the same variable. Following the ForceNonBasic operation, the column is no longer a basic column.

The computer may then determine the column selectors for the column of the [E][A] matrix in order to see if a pivot operation should be performed on the column. This is shown in block 470. The column selectors may be determined by determining the values of the [E][A] column that have row indices of −1 and 0. One selector value can be determined by multiplying the row of the [E] matrix indexed as −1 by the selected column of the [A] matrix to determine the −1 row entry of the selected column of the [E][A] matrix, as shown in block 472. And, the other selector value can be determined by multiplying the row of the [E] matrix indexed as 0 by the selected column of the [A] matrix to determine the 0 row of the selected column of the [E] [A] matrix, as shown by block 474.

Once the selector values for a column have been determined, the computer can assess whether a pivot operation should be performed. First, it should be noted that block 476 shows that a pivot operation should be performed on the column of the [E][A] matrix if the variable associated with the column is free. This is true regardless of the selector values. Block 478 shows that the column is not pivoted if the entry in the row indexed −1 of the [E][A] matrix is positive. So, the column is skipped in that instance.

In block 480, the column is skipped as a pivot column if the entry in the −1 indexed row of the column of the [E][A] matrix is 0 and the optimization problem is a minimization problem and the entry in the 0 indexed row of the column of the [E][A] matrix is greater-than-or-equal to 0.

In block 482, the column is skipped as a pivot column if the entry in the −1 indexed row of the column of the [E][A] matrix is 0 and the optimization problem, f, is a maximization problem and the entry in the 0 indexed row of the column of the [E][A] matrix is less-than-or-equal to zero.

In block 484, the column is selected as a pivot column if the entry in the −1 indexed row of the column of the [E][A] matrix is 0 and the optimization problem is a minimization problem and the entry in the 0 indexed row of the column of the [E][A] matrix is less than zero.

In block 486, the column is selected as a pivot column if the entry in the −1 indexed row of the column of the [E][A] matrix is 0 and the optimization problem is a maximization problem and the entry in the 0 indexed row of the column of the [E][A] matrix is greater than zero.

Once the pivot column is selected, a pivot row in the [E][A] matrix can be selected as shown in block 488. Finally, a pivot exchange can be performed using the pivot row and pivot column, as shown in block 490. The processing can then continue to assess whether another column of the [E][A] matrix should have a pivot-in-place operation performed.

Figure 5:
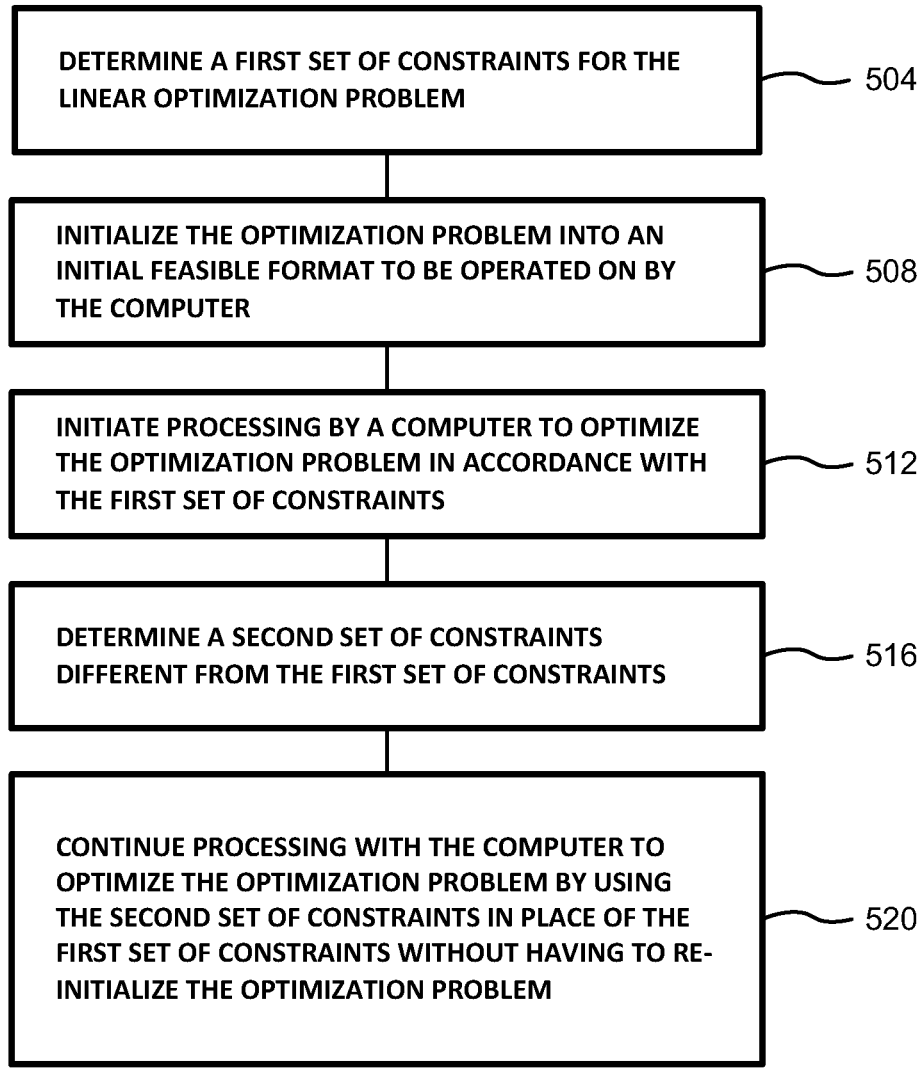
FIG. 5 is a flowchart illustrating a method of processing a linear programming problem and continuing to process the problem after a change in problem constraints without having to reinitialize the problem, in accordance with one embodiment of the invention.

Referring now to FIG. 5, a flow chart 500 illustrates an example of how one disclosed embodiment of the invention allows for dynamic processing of a linear programming problem. In block 504, one determines a first set of constraints for a linear optimization problem. In block 508, the optimization problem is initialized into a feasible form. Block 512 shows that the processing can be initiated by the computer to optimize the optimization problem in accordance with a first set of constraints.

When conditions related to the problem change, the constraints will necessarily change. For example, a linear programming problem for an industrial process now may require 550 tons of steel as opposed to an original amount of only 500 tons of steel. With other methods of solving linear programs, a change in conditions requires a re-initialization of the problem. However, as noted herein, the VSM allows one to continue processing the problem without having to start over from the beginning. In this way, the VSM allows for dynamic changes and continuous processing of the linear programming problem.

Thus, in block 516, a second set of constraints is determined from the change in conditions. The second set of constraints is different from the first set of constraints. Once the second set of constraints is determined, the processing of the linear programming problem by the computer can continue by using the second set of constraints in place of the first set of constraints and without having to re-initialize the optimization problem, as shown by block 520.

Figure 6A:
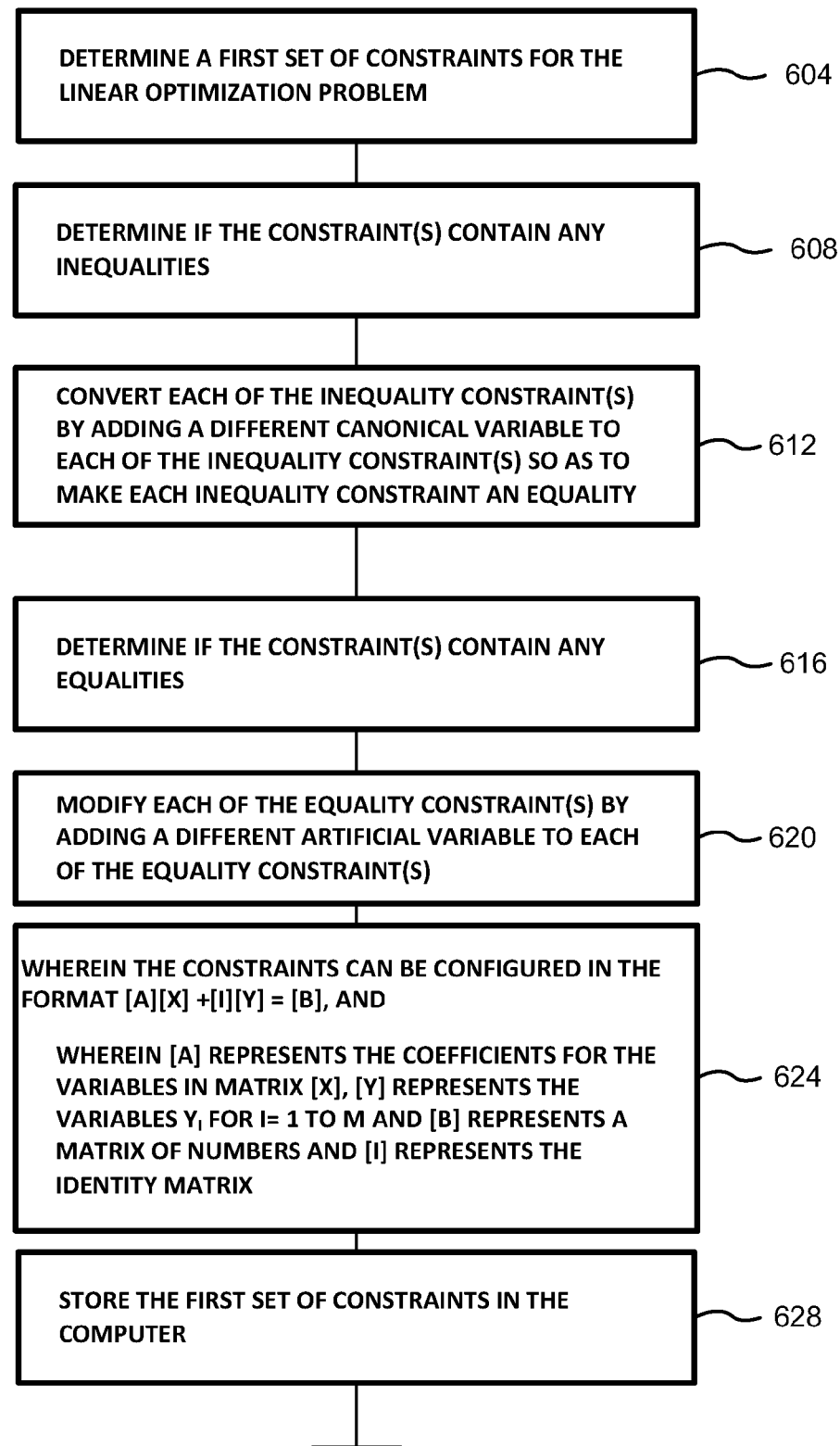
FIGS. 6A, 6B, and 6C are another example of a flowchart illustrating a method of processing a linear programming problem and continuing to process the problem after a change in problem constraints without having to reinitialize the problem, in accordance with one embodiment of the invention.
Figure 6A:
Figure 6B:
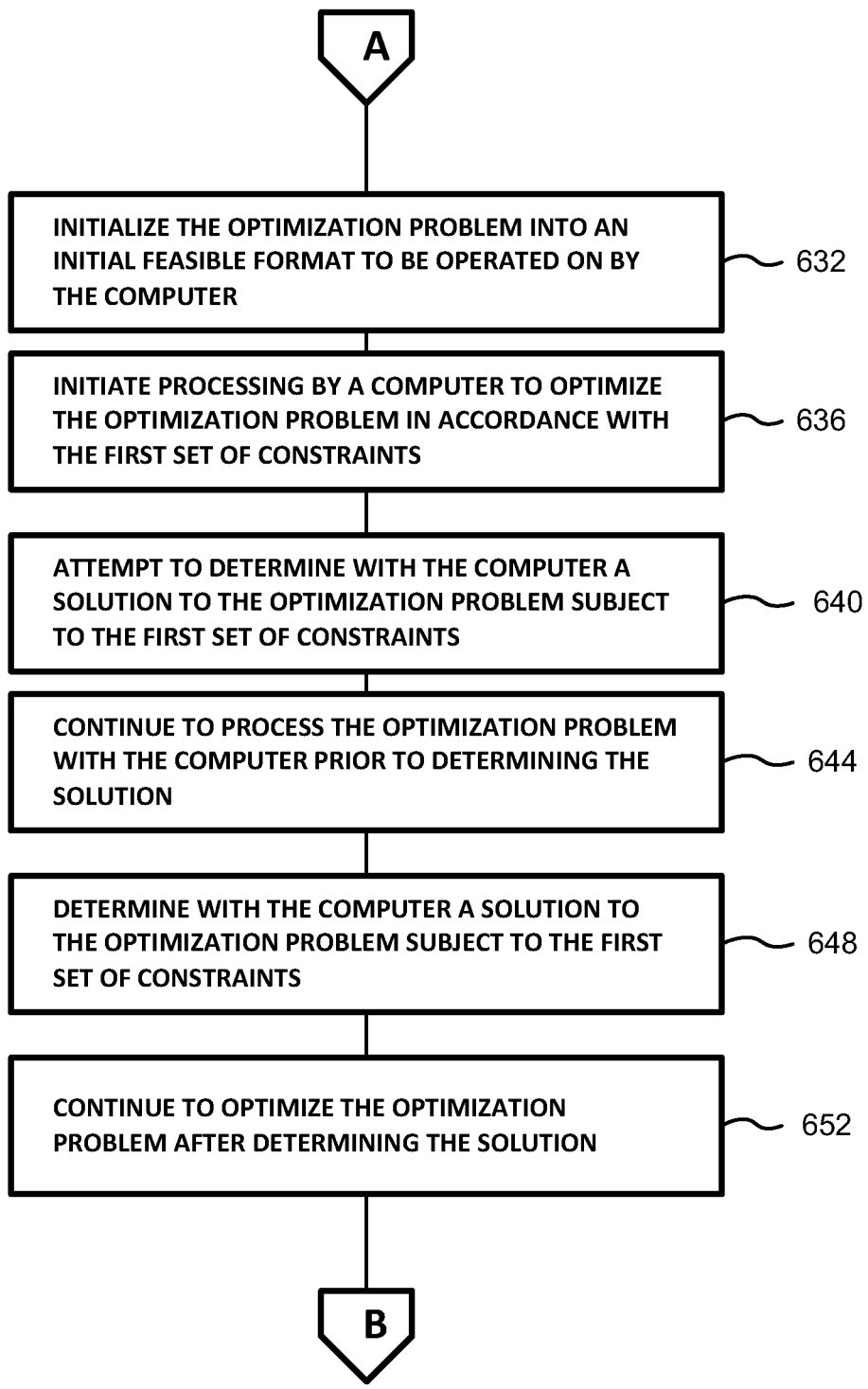
Figure 6C:
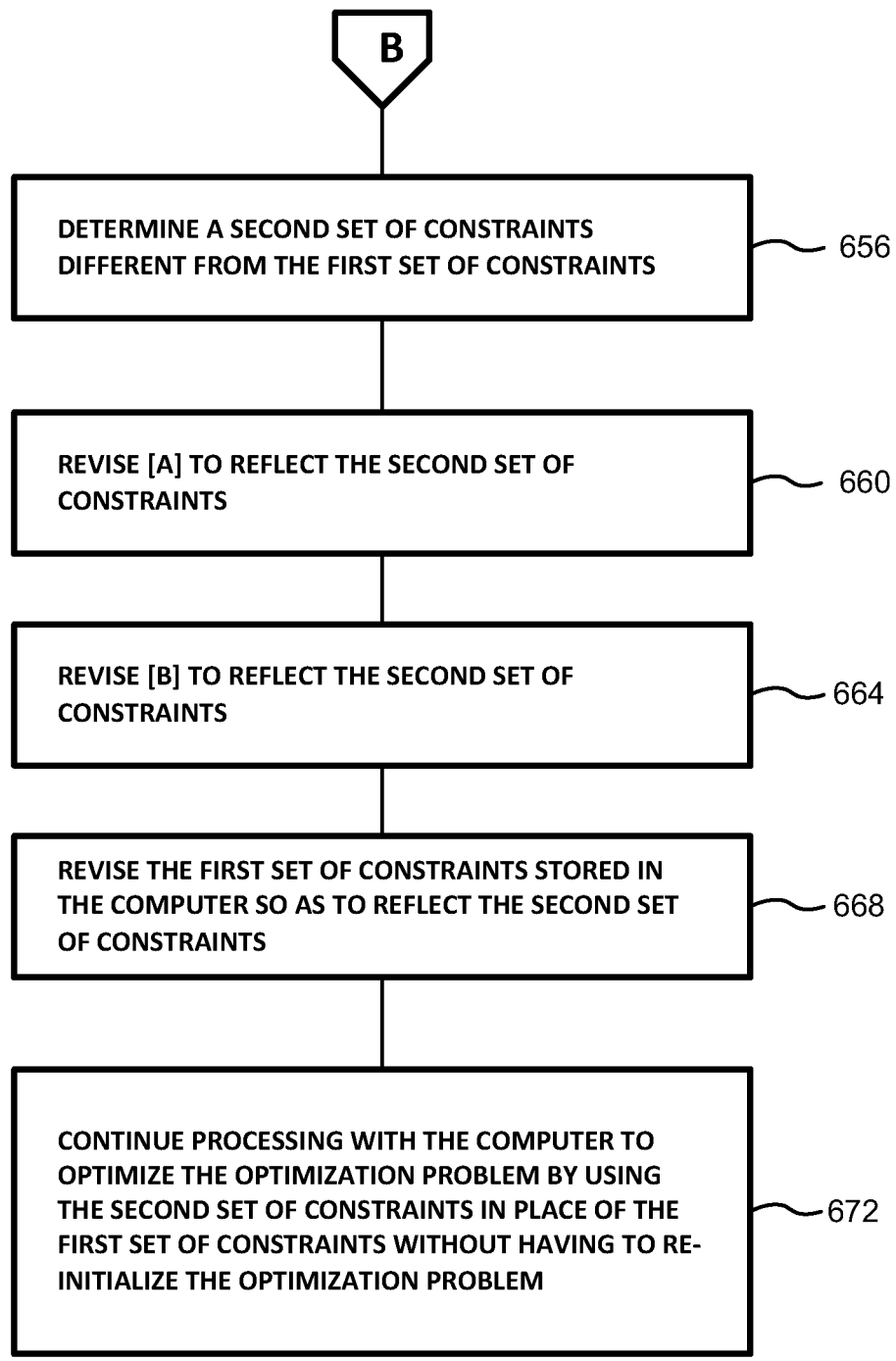

FIGS. 6A, 6B, and 6C illustrate another example of dynamic processing. In block 604, a first set of constraints for an optimization problem is provided. If the constraints contain any inequalities, as shown in block 608, each of the inequality constraints can be converted to an equality constraint by adding a different canonical variable to each of the inequality constraints, as shown by block 612. In block 616, a determination can be made as to whether the constraints contain any equalities. In that instance, an artificial variable can be added to such constraints, as shown by block 620.

Block 624 shows that the linear programming problem can be arranged in the format [A][X]+[I][Y]=[B]. Matrix [A] represents the coefficients for the variables in matrix [X]. Matrix [Y] represents the variables $Y_i$ for i=1 to m. Matrix [I] represents the identity matrix. And, matrix [B] represents a matrix of numbers.

Block 628 notes that the first set of constraints for the linear programming problem can be stored in the computer memory. In block 632, the optimization problem is initialized into an initial feasible format to be operated on by the computer. This is sometimes referred to as placing the problem into basic feasible form. Once the linear programming problem is established in basic feasible form, the computer can process the problem as defined by the first set of constraints, as shown by block 636. Thus, the computer can attempt to determine a solution to the optimization problem subject to the first set of constraints in accordance with block 640. Block 644 illustrates that a solution is not necessarily immediate and requires extended processing in many instances during which the constraints have sufficient time to change. Thus, the constraints could actually change before a first solution is achieved by the computer that is processing the linear programming problem.

Block 648 illustrates that the computer determines a solution (or comes to a resolution of whether the problem is solvable) while the problem is subject to the first set of constraints. The computer can continue to process the problem even after the solution is reached in case the constraints change and further processing is required, as shown in block 652.

When the conditions change and a new set of constraints applies to the problem, those new constraints can be stored on the computer, as shown in block 656. For example in block 660, the matrix [A] can be revised to reflect the new set of constraints. And, the matrix [B] can be revised to reflect the new set of constraints as shown in block 664. Block 668 again notes that the first set of constraints can be replaced in the computer memory by the second set of constraints.

Once the new set of constraints has been established in the computer memory, the computer can continue processing the optimization problem by using the second set of constraints in place of the original set of constraints. Moreover, this processing can continue without having to reinitialize the optimization, i.e., without having to start the process over from the beginning. This is illustrated by block 672.

Figure 8:
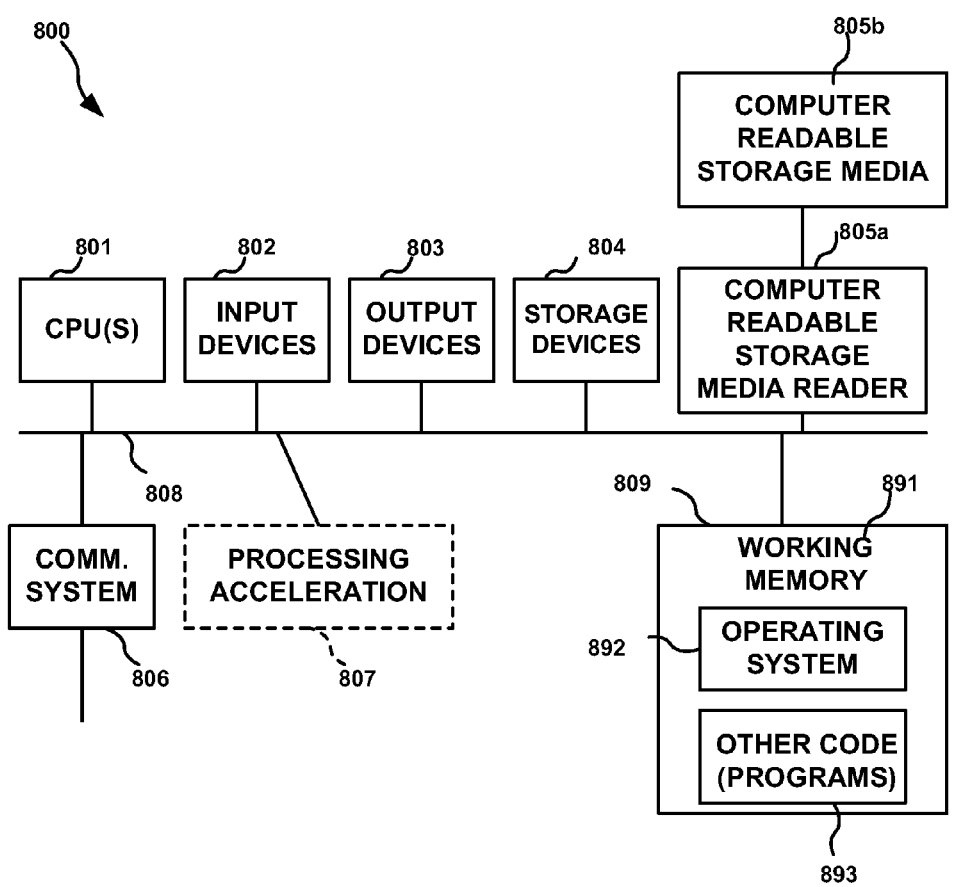
FIG. 8 illustrates a block diagram of a computer for software processing of a linear programming problem, in accordance with one embodiment of the invention.

As noted above, one embodiment can be implemented on a computer system such as computer system 700 in FIGS. 7A, 7B, and 7C. In addition, a computer such as that shown in FIG. 8 can be utilized to process a linear programming problem. FIG. 8 broadly illustrates how individual system elements can be implemented. System 800 is shown comprised of hardware elements that are electrically coupled via bus 808, including a processor 801, input device 802, output device 803, storage device 804, computer-readable storage media reader 805*a*, communications system 806 processing acceleration (e.g., DSP or special-purpose processors) 807 and memory 809. Computer-readable storage media reader 805a is further coupled to computer-readable storage media 805b, the combination comprehensively representing remote, local, fixed and/or removable storage devices plus storage media, memory, etc. for temporarily and/or more permanently containing computer-readable information, which can include storage device 804, memory 809 and/or any other such accessible system 800 resource. System 800 also comprises software elements (shown as being currently located within working memory 891) including an operating system 892 and other code 893, such as programs, applets, data and the like. As used herein, the term 'processor' includes any of one or more circuits, controllers, field-programmable gate arrays (FPGAs), microprocessors, application-specific integrated circuits (ASICs), other types of computational devices, or combinations thereof that are capable of performing functions ascribed to or associated with the processor.

System 800 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 800 component (e.g., within communications system 806). Customized hardware might also be utilized and/or particular elements might be implemented in hardware, software (including so-called "portable software," such as applets) or both. Further, while connection to other computing devices such as network input/output devices (not shown) may be employed, it is to be understood that wired, wireless, modem and/or other connection or connections to other computing devices might also be utilized. Distributed processing, multiple site viewing, information forwarding, collaboration, remote information retrieval and merging, and related capabilities are each contemplated. Operating system utilization will also vary depending on the particular host devices and/or process types (e.g., computer, appliance, portable device, etc.) Not all system 800 components will necessarily be required in all cases.

V. Applications

The techniques described herein have already been noted to have specific application to the reduction of computer error. Thus, when the Virtual Simplex Method is utilized on a computer, it can reduce error due to the particular properties of the computer relative to the implementation of other simplex-like methods used on the same computer.

Implementation of a simplex like method, including the present Virtual Simplex Method, is not limited to implementation on a computer Implementations of these methods can be done by hand, as well. However, when the Virtual Simplex Method is utilized on a computer, it is believed to provide the benefit of reducing computer error that other simplex like methods cannot reduce as effectively via their own implementations on the computer. Thus, reduction of computer error is considered an important application of the Virtual Simplex Method.

The Virtual Simplex Method also has particular application to problems arising in various industries. For example, the Virtual Simplex Method can be applied to problems arising in manufacturing, transportation, fanning, network planning, trading of financial instruments, and weather prediction. Perhaps the most fundamental application of the Virtual Simplex Method is the use to maximize profit in manufacturing a product.

Other applications of the Virtual Simplex Method can be seen for example in the book "In Pursuit of the Traveling Salesman" by William J. Cook, Princeton University Press, 2012, which is hereby incorporated by reference in its entirety and for all purposes.

The Virtual Simplex Method differs from all simplex-like methods in several important respects.

The VSM is a single phase method. Two phase methods cannot handle changed data without restarting. VSM can run continuously. In VSM the virtual problem will remain feasible throughout. Even if the data changes cause the optimization problem to go infeasible the virtual problem will remain feasible. The infeasibility of the optimization problem will be indicated by the presence of basic virtual variables in the optimal basic set. Further changes might make the optimization problem feasible again. When that happens the basic virtual variables will simply disappear from the optimal basic set.

After an initialization step VSM can run continuously as a virtual problem. It can continue to run after an optimal solution has been obtained. This allows VSM to monitor a dynamic problem such as a smart electric power grid, or a financial portfolio. It can also be used to recover from failures of systems caused by a failure of a component. An airline schedule where equipment might become unavailable unexpectedly is an example.

VSM is numerically robust. Simplex-like methods may have to be restarted because of computer error. They might require a reinversion of the stored inverse in a version of the revised simplex method. VSM can use Pivot-in-Place to maintain accuracy without reinversion. PIP can be enabled or disabled at any time for any reason seamlessly. It might be disabled to gain speed or disabled to maintain or restore accuracy.

VSM can use bUpdate to restore equivalence of the current representation of the constrains with the original constraints. This method prevents "going infeasible" from causing a run to fail.

VSM can use different column selection rules. They allow VSM to work on the optimization problem and the virtual problem at the same time. This allows VSM to be a single phase method.

The design of the EMatrix allows VSM to take advantage of massive parallelism.

While various embodiments have been described as methods or apparatuses, it should be understood that embodiments can be implemented through code coupled with a computer, e.g., code resident on a computer or accessible by the computer. For example, software and databases could be utilized to implement some of the methods discussed above. Thus, in addition to embodiments accomplished by hardware, it is also noted that these embodiments can be accomplished through the use of an article of manufacture comprised of a computer usable medium (such as a non-transitory computer usable medium) having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory, such as RAM, ROM, magnetic media, optical media, or magneto-optical media. Even more generally, the embodiments could be implemented in software, or in hardware, or any combination thereof including, but not limited to, software running on a general purpose processor, microcode, PLAs, or ASICs.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including any matter incorporated by reference.

It is thought that the apparatuses and methods of embodiments described herein will be understood from this specification. While the above description is a complete description of specific embodiments, the above description should not be taken as limiting.

It will be understood that while embodiments have been described in conjunction with specific examples, the foregoing description and examples are intended to illustrate, but not limit the claimed embodiments of the invention.

What is claimed is:

1. A special purpose computer for processing a linear optimization problem capable of being represented in the form [A][X]+[I][Y]=[B] and wherein the linear optimization problem can also be represented in the form [E][A][X]+[E][I][Y]=[E][B], the computer comprising:
   a first processor;
   a plurality of self-indexed row processors each configured to store a row of the matrix [E] and each of the row processors configured to store a set of self-contained instructions for autonomous operation;
   a computer memory in communication with the first processor and in communication with each row processor so that each row processor can read from the computer memory and write to the computer memory;
   wherein the first processor is configured to signal all of the row processors to process data related to the linear optimization problem.

2. The special purpose computer as claimed in claim 1 wherein each row processor comprises a register for storing an index associating that row processor with a row of the matrix [E].

3. The special purpose computer as claimed in claim 1 wherein each row processor comprises a register for storing an array of entries for the row of the matrix [E] associated with that row processor.

4. The special purpose computer as claimed in claim 1 wherein each row processor comprises a storage area for storing a value "b" which represents the right-hand-side of a constraint.

5. The special purpose computer as claimed in claim 1 wherein each row processor comprises a storage area for storing [B].

6. The special purpose computer as claimed in claim 1 wherein each row processor comprises a register for storing a value of a pivot column.

7. The special purpose computer as claimed in claim 1 wherein each row processor comprises a register for storing a ratio for the row of the matrix [E] associated with that row processor.

8. The special purpose computer as claimed in claim 1 wherein the first processor is configured to store data in the computer memory for access by every row processor.

9. The special purpose computer as claimed in claim 8 wherein the data represents a procedure for all of the row processors to perform.

10. The special purpose computer as claimed in claim 9 wherein the data represents a particular row processor.

11. The special purpose computer as claimed in claim 1 and further comprising a computer memory for storing matrix [A].

12. The special purpose computer as claimed in claim 1 and further comprising a computer memory for storing matrix [B].

13. The special purpose computer as claimed in claim 1 wherein the first processor is configured to cause a column from the matrix [A] to be stored in the computer memory in communication with the first processor and in communication with each row processor.

14. The special purpose computer as claimed in claim 1 wherein the first processor is configured to cause each row processor to perform an equivalent action on each processor's respective data.

15. The special purpose computer as claimed in claim 1 wherein each row processor is programmed with the same processing routines.

16. The special purpose computer as claimed in claim 1 wherein each of the row processors is configured so as not to be in direct communication with any of the remaining row processors.

17. The special purpose computer as claimed in claim 1 wherein the row processors are configured on a single integrated circuit.

18. The special purpose computer as claimed in claim 1 wherein the first processor, the computer memory, and the row processors are configured on a single integrated circuit.

19. The special purpose computer as claimed in claim 1 wherein each row processor is configured to perform an action in parallel with the remaining row processors upon receipt of a signal from the first processor.

20. The special purpose computer as claimed in claim 1 wherein the first processor is configured to signal all of the row processors via a command stored by the first processor into the computer memory and accessible by the row processors.

21. A special purpose computer for processing a linear optimization problem capable of being represented in the form [A][X]+[I][Y]=[B] and wherein the linear optimization problem can also be represented in the form [E][A][X]+[E][I][Y]=[E][B], the computer comprising:
    a first processor;
    a plurality of row processors each configured to store a row of the matrix [E];
    a computer memory in communication with the first processor and in communication with each row processor so that each row processor can read from the computer memory and write to the computer memory;
    wherein the first processor is configured to signal all of the row processors to process data related to the linear optimization problem;
    wherein the first processor is configured to cause one designated row processor to take action and configured to cause the remaining row processors to not take action.

22. A special purpose computer for processing a linear optimization problem capable of being represented in the form [A][X]+[I][Y]=[B] and wherein the linear optimization problem can also be represented in the form [E][A][X]+[E][I][Y]=[E][B], the computer comprising:
    a first processor;
    a plurality of row processors each configured to store a row of the matrix [E];
    a computer memory in communication with the first processor and in communication with each row processor so that each row processor can read from the computer memory and write to the computer memory;
    wherein the first processor is configured to signal all of the row processors to process data related to the linear optimization problem;

wherein the first processor is configured to cause one designated row processor to take no action and configured to cause the remaining row processors to perform an equivalent action on each processor's respective data.

* * * * *